US011581059B2

(12) United States Patent
Ferrara et al.

(10) Patent No.: US 11,581,059 B2
(45) Date of Patent: Feb. 14, 2023

(54) METHOD OF PREDICTING GRAFT VERSUS HOST DISEASE

(71) Applicant: Icahn School of Medicine at Mount Sinai, New York, NY (US)

(72) Inventors: James Ferrara, New York, NY (US); John E. Levine, New York, NY (US); Umut Özbek, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 263 days.

(21) Appl. No.: 16/343,382

(22) PCT Filed: Oct. 20, 2017

(86) PCT No.: PCT/US2017/057551
§ 371 (c)(1),
(2) Date: Apr. 18, 2019

(87) PCT Pub. No.: WO2018/075869
PCT Pub. Date: Apr. 26, 2018

(65) Prior Publication Data
US 2019/0259467 A1   Aug. 22, 2019

Related U.S. Application Data

(60) Provisional application No. 62/411,230, filed on Oct. 21, 2016.

(51) Int. Cl.
| | |
|---|---|
| *G16B 5/20* | (2019.01) |
| *G01N 33/564* | (2006.01) |
| *G01N 33/74* | (2006.01) |
| *G01N 33/68* | (2006.01) |
| *C12Q 1/6883* | (2018.01) |
| *A61K 31/436* | (2006.01) |
| *A61K 31/573* | (2006.01) |
| *A61K 38/00* | (2006.01) |
| *C12Q 1/68* | (2018.01) |

(52) U.S. Cl.
CPC ............. *G16B 5/20* (2019.02); *A61K 31/436* (2013.01); *A61K 31/573* (2013.01); *C12Q 1/68* (2013.01); *C12Q 1/6883* (2013.01); *G01N 33/564* (2013.01); *G01N 33/6893* (2013.01); *G01N 33/74* (2013.01); *A61K 38/00* (2013.01); *C12Q 2600/158* (2013.01); *G01N 2800/245* (2013.01); *G01N 2800/50* (2013.01); *G01N 2800/52* (2013.01)

(58) Field of Classification Search
CPC ......... G01N 2800/245; G01N 33/6893; G01N 2333/4724; G01N 2800/50; G01N 2800/52; G01N 33/564; G01N 33/74; A61K 31/436; A61K 31/573; A61K 38/00; A61P 29/00; C12N 2502/1157; C12N 2523/00; C12N 5/0663; C12Q 1/68; C12Q 1/6883; C12Q 2600/158; G16B 5/20
See application file for complete search history.

(56) References Cited

U.S. PATENT DOCUMENTS

| | | | |
|---|---|---|---|
| 2004/0071666 A1* | 4/2004 | Ferrara | A61K 35/28 424/93.7 |
| 2010/0184732 A1 | 7/2010 | McDonald | |
| 2013/0115232 A1 | 5/2013 | Ferrara et al. | |

FOREIGN PATENT DOCUMENTS

| | | |
|---|---|---|
| WO | 2016085866 A1 | 6/2016 |
| WO | 2016086161 A1 | 6/2016 |

OTHER PUBLICATIONS

International Search Report and Written Opinion dated Jan. 18, 2018, issued in corresponding PCT International Application No. PCT/US2017/057551.
Hartwell et al: "An early-biomarker algorithm predicts lethal graft-versus-host disease and survival", JCI Insight, vol. 2, No. 3, Feb. 9, 2017.
McDonald et al: "Plasma biomarkers of acute GVHD and nonrelapse mortality: predictive value of measurements before GVHD onset and treatment", Blood, vol. 126, No. 1, Jul. 2, 2015, pp. 113-120.
Hartwell et al: "An Early Biomarker Algorithm Predicts Lethal Graft-Vs-Host Disease and Survival after Allogeneic Hematopoietic Cell Transplantation", Biology of Blood and Marrow Transplantation, vol. 23, No. 3, Mar. 1, 2017.
Levine et al: "A prognostic score for acute graft-versus-host disease based on biomarkers: a multicenter study", Lancet Haematology, vol. 2, No. 1, Jan. 31, 2015 (Jan. 31, 2015), pp. E21-E29.
European Search Report Issued in European Patent Application No. 17861545.6 dated Apr. 14, 2020.
Renteria et al., "Development of a biomarker scoring system for use in graft-versus-host disease", Biomarkers in Medicine, 2016, vol. 10, No. 8, pp. 793-795.
Akahoshi et al., "Impact of graft-vesus-host disease and graft-verus-leukemia effect based on minimal residual disease in Philadelphia chromosome-positive acute lymphoblastic leukemia", British Journal of Haematology, 2020, vol. 190, pp. 84-92.
Kato et al., "Impact of graft-versus-host disease on relapse and survival after allogeneic stem cell transplantation for pediatric leukemia", Bone Marrow Transplantation, 2019, vol. 54, pp. 68-75.

(Continued)

*Primary Examiner* — Renee Claytor
*Assistant Examiner* — Sharon M. Papciak
(74) *Attorney, Agent, or Firm* — Troutman Pepper Hamilton Sanders LLP

(57) ABSTRACT

Embodiments of the invention describe to methods of diagnosing, classifying, and/or identifying a patient's risk of developing graft versus host disease, including severe or lethal graft versus host disease, after receiving hematopoietic cellular transplantation, a transfusion or a transplantation, but before the onset of clinical symptoms.

14 Claims, 18 Drawing Sheets

(56) References Cited

OTHER PUBLICATIONS

Storb et al., "Graft-Versus-Host Disease and Graft-Versus-Tumor Effects After Allogeneic Hematopoietic Cell Transplantation", Journal of Clinical Oncology, 2013, vol. 31, No. 12, pp. 1530-1538.
Yeshurun et al., "The impact of the graft-versus-ieukemia effect on survival in acute lymphoblastic leukemia", Blood Advances, 2019, vol. 3, No. 4, pp. 670-680.

* cited by examiner

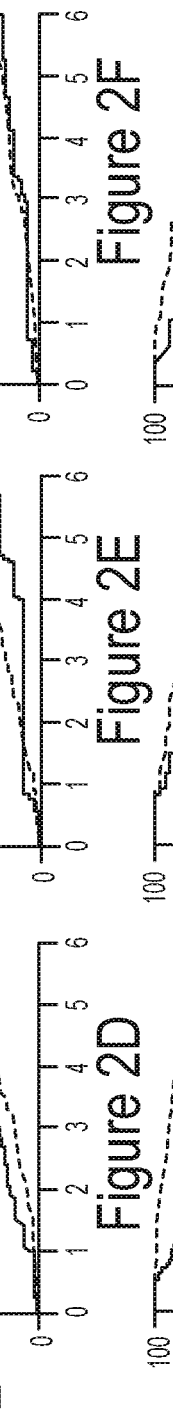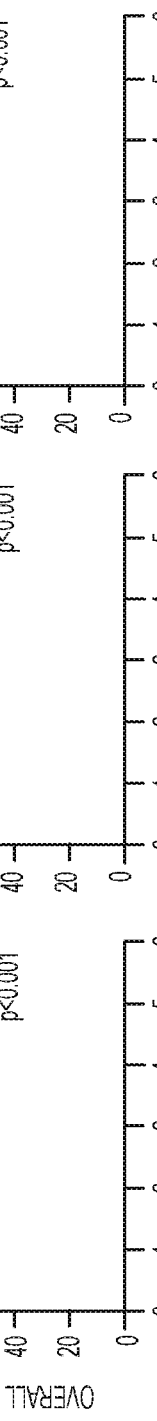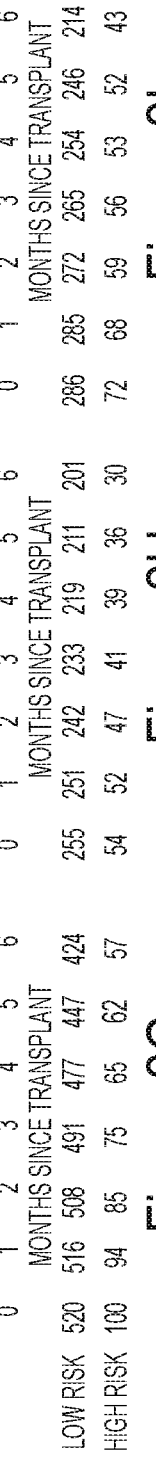

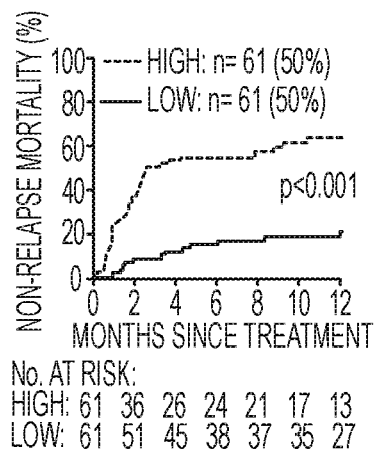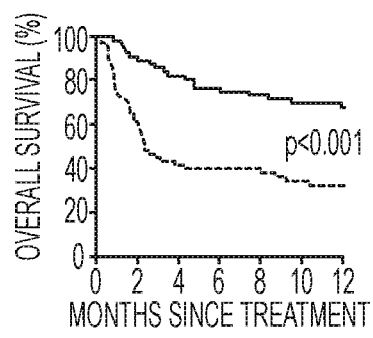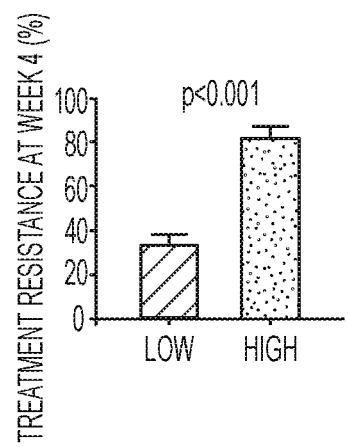
Figure 14A
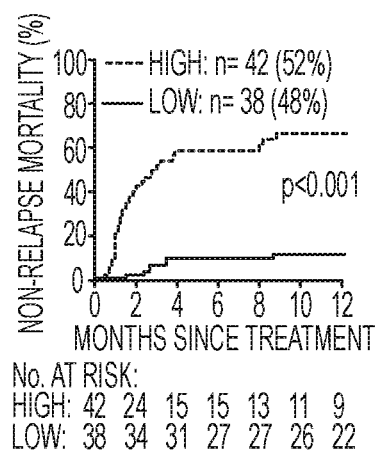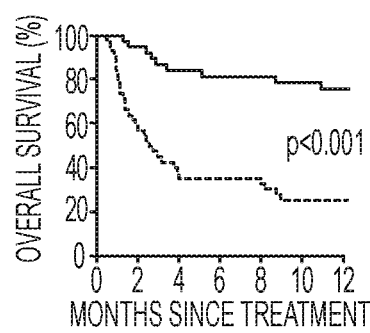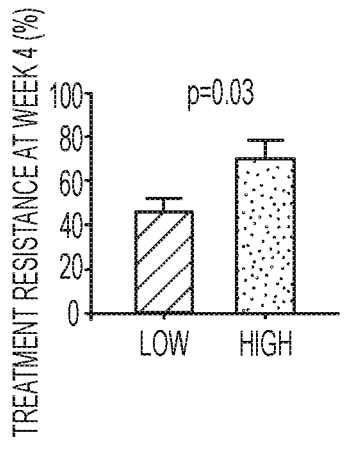
Figure 14B
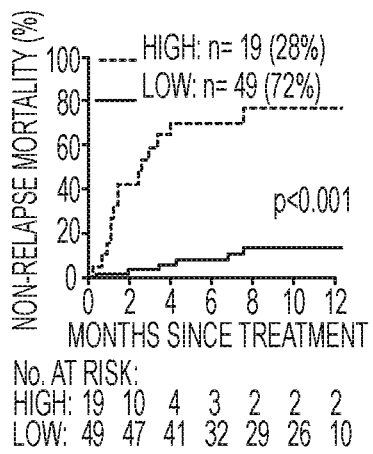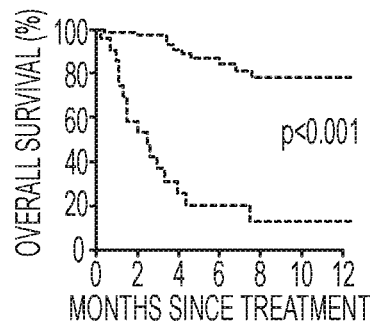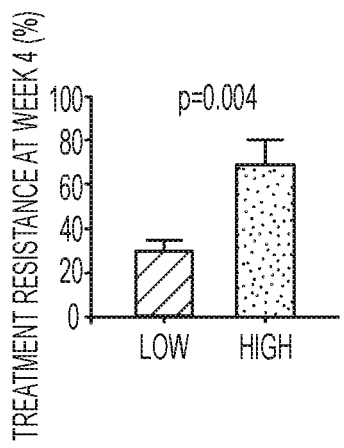
Figure 14C

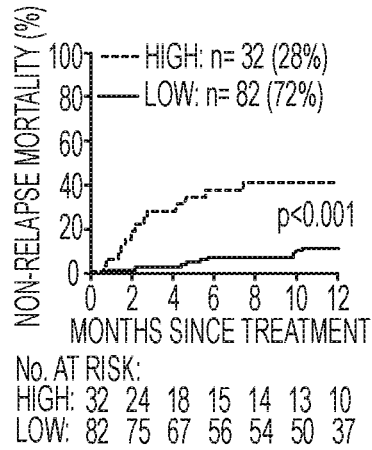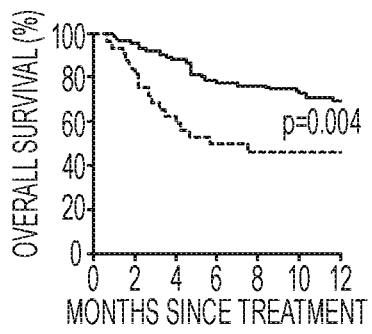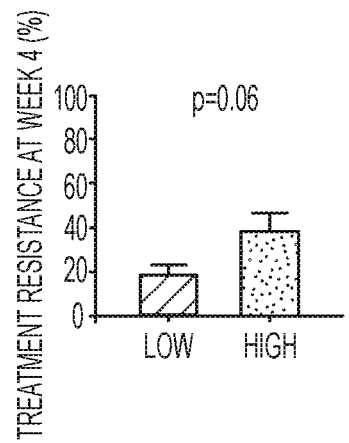
Figure 15A
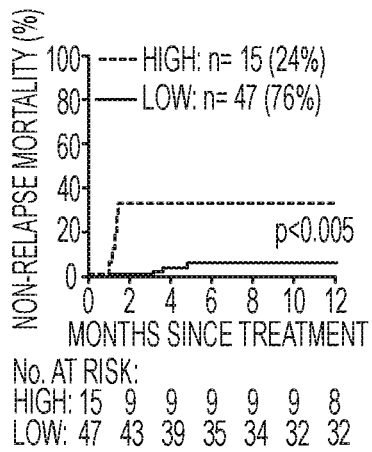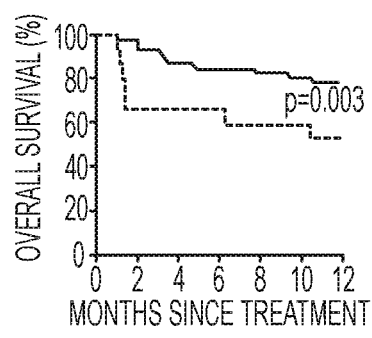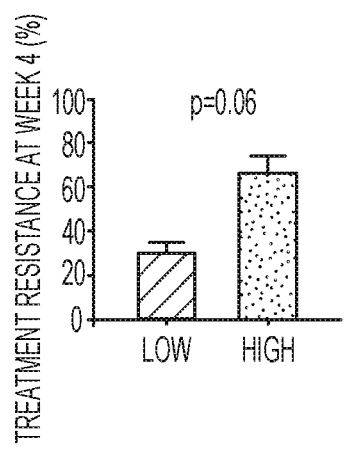
Figure 15B
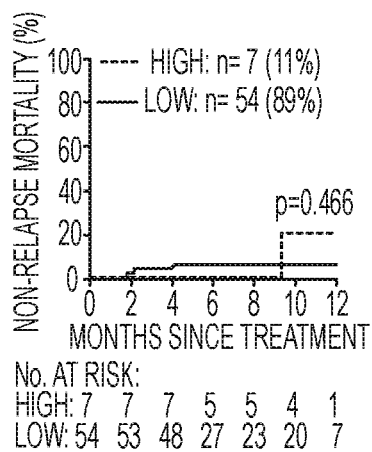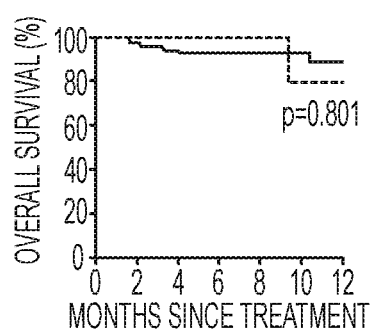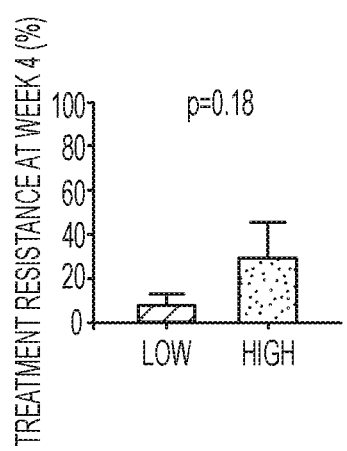
Figure 15C

METHOD OF PREDICTING GRAFT VERSUS HOST DISEASE

CROSS-REFERENCE TO RELATED APPLICATIONS

This application is a U.S. National Phase of International Patent Application No. PCT/US2017/057551, filed Oct. 20, 2017, which claims priority to U.S. Provisional Application No. 62/411,230, filed Oct. 21, 2016, both of which applications are herein incorporated by reference in their entireties.

GOVERNMENT SPONSORSHIP

This invention was made with government support under Grant Nos. R21CA173459, P01CA03942 and P30CA196521, each awarded by the National Cancer Institute of the National Institutes of Health. The government has certain rights in the invention.

BACKGROUND

Embodiments of the invention relate generally to methods of diagnosing, classifying, and/or identifying a patient's risk of developing graft versus host disease, such as severe or lethal graft versus host disease, after receiving hematopoietic cellular transplantation or transfusion or transplantation including lymphocytes, but before the onset of clinical symptoms. In some embodiments, the patient's GVHD is resistant to steroids. In some embodiments, the patient can be tested at multiple time points after receiving HCT to monitor development of GVHD or TA GVHD, such as for example and not limitation, patients who are determined to be at low risk for developing GVHD or TA GVHD at an early time point.

Hematopoietic cellular transplantation (HCT) is an important treatment for high risk hematologic malignancies (e.g., leukemia, lymphoma, multiple myeloma, acute leukemia, acute myeloid leukemia, dysplastic condition, acute lymphocytic leukemia (ALL)) whose curative potential depends on the graft-versus-leukemia (GVL) effect. Graft-versus-host disease (GVHD), the major cause of non-relapse mortality (NRM) post-HCT, is closely associated with GVL.[1-4] Pre-transplant clinical risk factors for GVHD include the degree of human leukocyte antigen (HLA) match between donor and recipient, recipient age, donor type, and conditioning regimen intensity.[5,6,37] Some centers use one or more of these risk factors to guide GVHD prophylaxis, such as the use of anti-thymocyte globulin when the donor is not an HLA-identical sibling,[7] but such approaches are globally immunosuppressive and carry their own risks, in particular of opportunistic infections.[8-9]

HCT is also used to treat non-malignant genetic disorders of the blood or immune system (e.g., severe combined immunodeficiency, hemophagocytic lymphohistiocytosis (HLH), hemoglobin disorders such as thalassemia, sickle cell anemia) in which a less severe GVHD effect is beneficial.

Acute GVHD affects 40-60% of patients and targets the skin, liver, and gastrointestinal (GI) tract.[6,10] The median onset of acute GVHD is approximately one month after transplant.[11,12] Recently, a signature of three plasma biomarkers (TNFR1, ST2, and REG3α) at the onset of clinical symptoms has been shown to predict non-relapse mortality and response to treatment.11 However, it would be beneficial for treatment options to identify a biomarker signature early after HCT could predict non-relapse mortality and GVHD before the development of overt clinical disease.

Acute GVHD is measured by dysfunction in the three organ systems: the skin, liver and gastrointestinal (GI) tract (Cutler et al., Manifestation and Treatment of Acute Graft-Versus-Host-Disease, Appelbaum et al., eds., Thomas' Hematopoietic Cell Transplantation, 4th edn. Oxford: Blackwell Publishing Ltd; 2009. p. 1287-303; Mowat et al., Intestinal Graft-vs.-Host Disease, Ferrara et al., eds., Graft-vs-Host Disease, 3rd edn. New York: Marcel Dekker; 2004. p. 279-327; Ferrara et al., Lancet 373: 1550-61, 2009). Acute GVHD of the GI tract affects up to 60% of patients receiving allogeneic HCT (Martin et al., Biol. Blood Marrow Transpl. 10: 320-7, 2004; MacMillan et al., Biol. Blood Marrow Transpl. 8: 387-94, 2002). This dysfunction manifests with nausea, vomiting, anorexia, secretory diarrhea and, in more severe cases, abdominal pain and/or hemorrhage. Thus, the etiology of diarrhea following HCT presents a common diagnostic dilemma.

Acute GVHD typically occurs between two and eight weeks after transplant, but may occur later, and is often clinically indistinguishable from other causes of GI dysfunction such as conditioning regimen toxicity, infection or medication. Endoscopic biopsy is often used to confirm, the diagnosis, but histologic severity on biopsy has not consistently correlated with clinical outcome. Clinical stage two or greater (more than one liter of diarrhea per day) is associated with reduced survival, but daily stool volume can vary considerably. Lower GI GVHD responds poorly to treatment compared to other target organs, and treatment with high-dose systemic steroid therapy carries significant risks, especially infectious complications in profoundly immunosuppressed patients. Thus, determining risk of developing GVHD and monitoring GVHD throughout treatment is important in patients with GVHD that is resistant to steroid therapies.

Transfusion-associated GVHD (TA GVHD) can occur in immunocompromised recipients (e.g., patients with inborn immunodeficiency, acquired immunodeficiency, or other malignancy), as well as non-immunocompromised recipients, when the recipient's (host's) immune system is unable to or does not recognize the donor lymphocytes (graft) as foreign, but the donor lymphocytes recognize the recipient's cells as foreign and mount an immunological attack against the recipient. TA GVHD can result from transfer of lymphocytes from the donor to the recipient, including directed blood transfusion, small bowel transplantation, and liver transplantation. The clinical symptoms of TA GVHD are the same as GVHD.

Responses to primary therapy, high dose systemic corticosteroids, have not improved and survival for patients with treatment resistant GVHD remains particularly poor.[38] The clinical response after four weeks of treatment is a validated surrogate for long term survival[39], but physicians usually cannot wait one month before deciding whether to modify therapy, particularly for patients who do not achieve or maintain a convincing clinical response. In clinical practice, the period of one week of treatment is commonly used to determine escalation or de-escalation of immunosuppressive therapy but this early response correlates poorly with long-term outcomes[40]. Patient who do not respond early to systemic steroids have a generally poor prognosis but results are inconsistent among transplant centers and biomarkers that accurately predict long term outcomes in this highly immunosuppressed population are urgently needed.

What is needed, therefore, is a method of identifying, classifying or diagnosing a patient's risk for developing (i)

GVHD soon after receiving HCT or (ii) TA GHVD after a transfusion or transplantation, but before clinical symptoms of GVHD or TA GVHD develop, as well as determining the patient's risk level for developing GVHD or TA GVHD, including severe or lethal GVHD or TA GHVD, and subsequently treating the patient appropriately. In some embodiments, the patient's GVHD is resistant to steroid therapies. In some embodiments, the patient is tested at multiple time points after receiving HCT to monitor development of GVHD or TA GVHD, such as for example and not limitation, patients who are determined to be at low risk for developing GVHD or TA GVHD at an early time point. It is to such a method that embodiments of the present invention are directed.

BRIEF SUMMARY OF THE INVENTION

As specified in the Background Section, there is a great need in the art to identify technologies for reliable, consistent and simple diagnosis and classification of a patient's risk of developing GVHD, including severe or lethal GVHD, soon after receiving HCT but before clinical onset of symptoms, and use this understanding to develop novel diagnostic methods. There is also a great need in the art to identify technologies for reliable, consistent and simple diagnosis and classification of a patient's risk of developing TA GVHD, including severe or lethal TA GVHD, soon after receiving transfusion or transplantation but before clinical onset of symptoms, and use this understanding to develop novel diagnostic methods, including in patients who are resistant to steroid therapies. The present invention satisfies this and other needs. Embodiments of the present invention relate generally to methods for diagnosis, classification and monitoring of GVHD and TA GVHD, including but not limited to severe or lethal GVHD and TA GVHD, well before the symptoms of GVHD or TA GVHD begin to appear. In some embodiments, the patient is tested at multiple time points after receiving HCT to monitor development of GVHD or TA GVHD, such as for example and not limitation, patients who are determined to be at low risk for developing GVHD or TA GVHD at an early time point.

In one aspect, the invention provides a method for determining the risk of developing severe or lethal GVHD in a subject who has recently undergone HCT, comprising the steps of:
  a) measuring level(s) of at least one of ST2 and Reg3α in a first blood sample collected from the subject;
  b) analyzing the level(s) according to the algorithm log $[-\log(1-\hat{p})]=-11.263+1.844(\log ST2)+0.577(\log REG3\alpha)$;
  c) determining a first $\hat{p}$ value for the subject;
  d) comparing the first $\hat{p}$ value obtained from the measurement analysis to an optimal classification threshold; and
  e) identifying the subject as (i) being at risk for developing severe or lethal GVHD when the first $\hat{p}$ value is greater than or equal to the optimal classification threshold or (ii) not being at risk for developing severe or lethal GVHD when the first $\hat{p}$ value is less than the optimal classification threshold.

In another aspect, the invention provides a method for predicting the risk of developing severe or lethal GVHD and/or NRM in a subject who has recently undergone HCT, comprising the steps of:
  a) measuring level(s) of at least one of ST2 and Reg3α in a first blood sample collected from the subject;
  b) analyzing the level(s) according to the algorithm log $[-\log(1-\hat{p})]=-11.263+1.844(\log ST2)+0.577(\log REG3\alpha)$;
  c) determining a first $\hat{p}$ value for the subject;
  d) comparing the first $\hat{p}$ value obtained from the measurement analysis to an optimal classification threshold; and
  e) identifying the subject as (i) being at risk for developing severe or lethal severe or lethal GVHD when the first $\hat{p}$ value is greater than or equal to the optimal classification threshold or (ii) not being at risk for developing severe or lethal severe or lethal GVHD when the first $\hat{p}$ value is less than the optimal classification threshold.

In yet another aspect, the invention provides a method for predicting severe or lethal GVHD in a subject who has recently undergone HCT, comprising the steps of:
  a) measuring level(s) of at least one of ST2 and Reg3α in a first blood sample collected from the subject;
  b) analyzing the level(s) according to the algorithm log $[-\log(1-\hat{p})]=-11.263+1.844(\log ST2)+0.577(\log REG3\alpha)$;
  c) determining a first $\hat{p}$ value for the subject;
  d) comparing the first $\hat{p}$ value obtained from the measurement analysis to an optimal classification threshold; and
  e) identifying the subject as (i) being at risk for developing severe or lethal GVHD when the first $\hat{p}$ value is greater than or equal to the optimal classification threshold or (ii) not being at risk for developing severe or lethal GVHD when the first $\hat{p}$ value is less than the optimal classification threshold.

In one aspect, the invention provides a method for predicting a subject's response to a treatment for severe or lethal GVHD in a subject who has recently undergone HCT, comprising the steps of:
  a) measuring level(s) of at least one of ST2 and Reg3α in a first blood sample collected from the subject;
  b) analyzing the level(s) according to the algorithm log $[-\log(1-\hat{p})]=-11.263+1.844(\log ST2)+0.577(\log REG3\alpha)$;
  c) determining a first $\hat{p}$ value for the subject;
  d) comparing the first $\hat{p}$ value obtained from the measurement analysis to an optimal classification threshold; and
  e) identifying the subject as (i) being at risk for developing severe or lethal GVHD when the first $\hat{p}$ value is greater than or equal to the optimal classification threshold or (ii) not being at risk for developing severe or lethal GVHD when the first $\hat{p}$ value is less than the optimal classification threshold; and
  (f) predicting the subject's response to the treatment for severe or lethal GVHD based on the identification step.

In another aspect, the invention provides a method for diagnosing severe or lethal GVHD in a subject who has recently undergone HCT, comprising the steps of:
  a) measuring level(s) of at least one of ST2 and Reg3α in a first blood sample collected from the subject;
  b) analyzing the level(s) according to the algorithm log $[-\log(1-\hat{p})]=-11.263+1.844(\log ST2)+0.577(\log REG3\alpha)$;
  c) determining a first $\hat{p}$ value for the subject;
  d) comparing the first $\hat{p}$ value obtained from the measurement analysis to an optimal classification threshold; and
  e) identifying the subject as (i) having severe or lethal GVHD when the first $\hat{p}$ value is greater than or equal to the optimal classification threshold or (ii) not having severe or lethal GVHD when the first $\hat{p}$ value is less than the optimal classification threshold.

In yet another aspect, the invention provides a method for determining susceptibility of developing severe or lethal GVHD and/or NRM in a subject who has recently undergone HCT, comprising the steps of:
  a) measuring level(s) of at least one of ST2 and Reg3α in a first blood sample collected from the subject;
  b) analyzing the level(s) according to the algorithm log $[-\log(1-\hat{p})]=-11.263+1.844(\log ST2)+0.577(\log REG3\alpha)$;
  c) determining a first $\hat{p}$ value for the subject;

d) comparing the first $\hat{p}$ value obtained from the measurement analysis to an optimal classification threshold; and e) identifying the subject as (i) being susceptible to developing severe or lethal GVHD when the first $\hat{p}$ value is greater than or equal to the optimal classification threshold or (ii) not being susceptible to developing severe or lethal GVHD when the first $\hat{p}$ value is less than the optimal classification threshold.

In one aspect, the invention provides a method for detection of severe or lethal GVHD in a subject who has recently undergone HCT, comprising the steps of:

a) measuring level(s) of at least one of ST2 and Reg3α in a first blood sample collected from the subject;

b) analyzing the level(s) according to the algorithm $\log[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) having or being at risk for severe or lethal GVHD when the first $\hat{p}$ value is greater than or equal to the optimal classification threshold or (ii) not having or being at risk for severe or lethal GVHD when the first $\hat{p}$ value is less than the optimal classification threshold.

In another aspect, the invention provides a method for differentially diagnosing severe or lethal GVHD from mild to moderate GVHDin a subject who has recently undergone HCT, comprising the steps of:

a) measuring level(s) of at least one of ST2 and Reg3α in a first blood sample collected from the subject;

b) analyzing the level(s) according to the algorithm $\log[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) having or being at risk for severe or lethal GVHD when the first $\hat{p}$ value is greater than or equal to the optimal classification threshold or (ii) having or being at risk for mild to moderate GVHD when the first $\hat{p}$ value is less than the optimal classification threshold.

In still another aspect, the invention provides a method for classifying a subject who has recently undergone HCT as having or being at risk for severe or lethal GVHD, comprising the steps of:

a) measuring level(s) of at least one of ST2 and Reg3α in a first blood sample collected from the subject;

b) analyzing the level(s) according to the algorithm $\log[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) having or being at risk for severe or lethal GVHD when the first $\hat{p}$ value is greater than or equal to the optimal classification threshold or (ii) not having or being at risk for severe or lethal GVHD when the first $\hat{p}$ value is less than the optimal classification threshold.

In one aspect, the invention provides a method for monitoring the potential to develop severe or lethal GVHD in a subject who has recently undergone HCT, comprising the steps of:

a) measuring level(s) of at least one of ST2 and Reg3α in a first blood sample collected from the subject;

b) analyzing the level(s) according to the algorithm $\log[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) having or being at risk for severe or lethal GVHD when the first $\hat{p}$ value is greater than or equal to the optimal classification threshold or (ii) not having or being at risk for severe or lethal GVHD when the first $\hat{p}$ value is less than the optimal classification threshold;

f) measuring the level(s) of at least one of ST2 and Reg3α in a second blood sample collected from the subject more than eleven days after undergoing HCT;

g) analyzing the level(s) in the second blood sample according to the algorithm $\log[-\log(1-\hat{p})]=-11.263+1.844(\log ST2)+0.577(\log REG3\alpha)$;

h) determining a second $\hat{p}$ value for the subject;

i) comparing the second $\hat{p}$ value obtained from the measurement analysis to the optimal classification threshold and to the first $\hat{p}$ value;

j) identifying the subject as (i) continuing to have or be at risk for severe or lethal GVHD when the second $\hat{p}$ value is greater than or equal to the optimal classification threshold and/or when the second $\hat{p}$ value is the same as or greater than the first $\hat{p}$ value or (ii) not continuing to have or not continuing to be at risk of having severe or lethal GVHD when the first $\hat{p}$ value is less than the optimal classification threshold;

k) optionally modifying the patient's therapeutic or prophylactic regimen based on the identification in step j; and l) repeating steps f-j on subsequent days after HCT as determined by a physician.

In another aspect, the invention provides a method for monitoring the success and/or efficacy of treatment and/or prophylaxis of a subject who has recently undergone HCT and has or has been identified as likely to have severe or lethal GVHD, comprising the steps of:

a) measuring level(s) of at least one of ST2 and Reg3α in a first blood sample collected from the subject within four to ten days after undergoing HCT;

b) analyzing the level(s) according to the algorithm $\log[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold;

e) identifying the treatment and/or prophylaxis as (i) being successful when the first $\hat{p}$ value is greater than or equal to the optimal classification threshold or (ii) not being successful when the first $\hat{p}$ value is less than the optimal classification threshold; and optionally modifying the patient's therapeutic and/or prophylactic regimen based on the identification in step e; and further optionally:

f) measuring the level(s) of at least one of ST2 and Reg3α in a second blood sample collected from the subject more than eleven days after undergoing HCT;

g) analyzing the level(s) in the second blood sample according to the algorithm $\log[-\log(1-\hat{p})]=-11.263+1.844(\log ST2)+0.577(\log REG3\alpha)$;

h) determining a second $\hat{p}$ value for the subject;

i) comparing the second $\hat{p}$ value obtained from the measurement analysis to the optimal classification threshold and to the first $\hat{p}$ value;

j) identifying the treatment and/or prophylaxis as (i) successful when the second $\hat{p}$ value is less than or equal to the optimal classification threshold and/or when the second $\hat{p}$ value is less than the first $\hat{p}$ value or (ii) not successful when the second $\hat{p}$ value is greater than or equal to the optimal classification threshold and/or when the second $\hat{p}$ value is greater than the first $\hat{p}$ value;

k) optionally modifying the patient's therapeutic or prophylactic regimen based on the identification in step j; and l) repeating steps f-j on subsequent days after HCT as determined by a physician.

In one aspect, the invention provides a method for selecting a subject for a treatment and/or prophylaxis of severe or lethal for GVHD, comprising the steps of:

a) measuring level(s) of at least one of ST2 and Reg3α in a first blood sample collected from the subject;

b) analyzing the level(s) according to the algorithm log $[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) being suitable for the treatment and/or prophylaxis when the first $\hat{p}$ value is greater than or equal to the optimal classification threshold or (ii) not being suitable for the treatment and/or prophylaxis when the first $\hat{p}$ value is less than the optimal classification threshold.

In another aspect, the invention provides a method for selecting a subject for a clinical trial for severe or lethal GVHD therapeutic compositions and/or methods, comprising the steps of:

a) measuring level(s) of at least one of ST2 and Reg3α in a first blood sample collected from the subject;

b) analyzing the level(s) according to the algorithm log $[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) being suitable for the clinical trial when the first $\hat{p}$ value is greater than or equal to the optimal classification threshold or (ii) not being suitable for the clinical trial when the first $\hat{p}$ value is less than the optimal classification threshold.

In yet another aspect, the invention provides a method for treating and/or preventing severe or lethal GVHD in a subject who has recently undergone HCT, comprising the steps of:

a) measuring level(s) of at least one of ST2 and Reg3α in a first blood sample collected from the subject;

b) analyzing the level(s) according to the algorithm log $[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold;

e) identifying the subject as (i) being suitable for treatment or successfully treated when the first $\hat{p}$ value is greater than or equal to the optimal classification threshold or (ii) not being suitable for treatment or successfully treated when the first $\hat{p}$ value is less than the optimal classification threshold; and f) utilizing appropriate therapeutic and/or prophylactic compositions and/or methods if the subject has severe or lethal GVHD and/or NRM.

In a related aspect, the invention provides a method of prognosis of severe or lethal GVHD in a subject who has recently undergone HCT, comprising the steps of:

a) measuring level(s) of at least one of ST2 and Reg3α in a first blood sample collected from the subject;

b) analyzing the level(s) according to the algorithm log $[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) likely to develop severe or lethal GVHD when the first $\hat{p}$ value is greater than or equal to the optimal classification threshold or (ii) not likely to develop severe or lethal GVHD when the first $\hat{p}$ value is less than the optimal classification threshold.

In one aspect, the invention provides a method for differentiating between severe or lethal GVHD and mild to moderate GVHD in a subject who has recently undergone HCT, comprising the steps of:

a) measuring level(s) of at least one of ST2 and Reg3α in a first blood sample collected from the subject;

b) analyzing the level(s) according to the algorithm log $[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) having severe or lethal GVHD when the first $\hat{p}$ value is greater than or equal to the optimal classification threshold or (ii) having mild to moderate GVHD when the first $\hat{p}$ value is less than the optimal classification threshold.

In any of the foregoing methods, the patient is suffering from a high risk hematologic malignancy. In one embodiment, the patient is suffering from leukemia, lymphoma, multiple myeloma, acute leukemia, acute myeloid leukemia, dysplastic condition, and/or acute lymphocytic leukemia (ALL).

In any of the foregoing methods, the optimal classification threshold is a $\hat{p}$ value of greater than or equal to 0.12.

In any of the foregoing methods, the optimal classification threshold is a $\hat{p}$ value of greater than or equal to 0.16.

In any of the foregoing methods, the patient has received HCT at least four days before the blood sample is collected.

In any of the foregoing methods, the patient has received HCT at most ten days before the blood sample is collected.

In any of the foregoing methods, the patient has received HCT between four to ten days before the blood sample is collected.

In any of the foregoing methods, the patient has received HCT seven days before the blood sample is collected.

In any of the foregoing methods, step (a) further comprises obtaining a blood sample from the patient and subsequently isolating at least one of ST2 and Reg3α.

In any of the foregoing methods, step (a) further comprises determining the levels of at least one of ST2 and Reg3α.

In any of the foregoing methods, determination of the levels of at least one of ST2 and Reg3α further comprise isolating nucleic acid and/or protein from the sample.

In any of the foregoing methods, the method further comprises treatment of patients determined to have, or be at risk for, severe GHVD.

In any of the foregoing methods, the patient's GVHD is treatment resistant, such as for example and not limitation, GVHD that is resistant to steroid therapies, such as for example and not limitation, high dose systemic corticosteroid therapies.

In any of the foregoing methods, the patient can be tested at multiple time points after receiving HCT to monitor development of GVHD or TA GVHD, such as for example and not limitation, patients who are determined to be at low risk for developing GVHD or TA GVHD at an early time point. In some embodiments, a first blood sample is taken from the patient about 7 days after receiving HCT, and a second blood sample is taken from the patient about 14 days after receiving HCT.

In one embodiment of any of the foregoing methods, the treatment is prophylactic and comprises administration of appropriate prophylactically effective pharmaceutical compositions and/or use of appropriate prophylactically effective methods. In one embodiment, the prophylactic treatment comprises immunosuppressive drugs, calcineurin inhibitors, high doses of steroids (e.g., corticosteroids such as for example and not limitation, prednisone, methylprednisolone, and the like), selective depletion of alloreactive T lymphocytes from the donor graft, the use of umbilical cord blood as a source of donor cells, and choosing more closely HLA-matched donors.

In one embodiment of any of the foregoing methods, the treatment comprises administration of appropriate therapeutically effective pharmaceutical compositions and/or use of appropriate therapeutically effective methods. In one embodiment, the therapeutically effective compositions comprise corticosteroids (e.g., prednisone, prednisolone, methylprednisolone, and the like) and/or immunosuppressive therapies (e.g., for example and not limitation, cyclosporine, tacrolimus (also known as FK-506 or Fujimycin), methotrexate, mycophenolate mofetil, antithymocyte globulin (ATG), monoclonal antibodies (e.g., anti-CD3, -CD5, and -IL-2 antibodies, anti-CD20 (rituximab), and alemtuzumab (Campath)), anti-TNF drugs (e.g., etanercept (Enbrel®), infliximab, adlimumab), lymphocyte immune globulin (Atgam®), sirolimus, ustekinumab, extracorporeal photophoresis (ECP), anti-CD3 drugs (e.g.,Visilizumab and OKT3), anti-CD5 drug and anti-IL-2 (CD25) drugs (inolimomab, basiliximab, daclizumab, and denileukin diftitox), anti-CD147 drugs (e.g., Alefacept), anti-IL1 R drugs, (e.g., Anakinra), anti-integrin drugs (e.g., $\alpha 4\beta 7$ antagonist vedolizumab (Entyvio®), $\alpha 4$ antagonist natalizumab (Tysabri®), and $\beta 7$ antagonist etrolizumab), mesenchymal stem cells, and regulatory T cells). In another embodiment, the therapeutically effective methods comprise use of high doses of steroids (e.g., corticosteroids) and/or use of immunosuppressive therapies.

In any of the foregoing methods, steps (b) and/or (c) and/or (d) and/or (e) are performed by a computer.

In a related aspect, the invention provides a kit for diagnosing and/or detecting severe GVHD in a subject, optionally a subject with treatment-resistant GVHD, said kit comprising probes directed towards one or more of ST2 and Reg3α, wherein the probes can be used to determine the expression levels of ST2 and Reg3α.

In one embodiment, the kit further comprises: a detection means; an amplification means; and control probes.

These and other objects, features and advantages of the present invention will become more apparent upon reading the following specification in conjunction with the accompanying description, claims and drawings.

BRIEF DESCRIPTION OF THE DRAWINGS

The accompanying Figures, which are incorporated in and constitute a part of this specification, illustrate several aspects described below. The patent or application file contains at least one drawing executed in color. Copies of this patent or patent application publication with color drawing(s) will be provided by the Office upon request and payment of the necessary fee.

FIG. 2A-2I. Outcomes According to MAGIC Risk Stratification. 6-month cumulative incidences of non-relapse mortality in high risk (HR, pink) and low risk (LR, blue) were defined by the MAGIC algorithm. Training set (FIG. 2A): HR 28% (95% confidence interval [CI], 20 to 37); LR 7% (95% CI, 5 to 10); Test set (FIG. 2B): HR 33% (95% CI, 21 to 46); LR 7% (95% CI, 5 to 11); Validation set (FIG. 2C): HR 26% (95% CI, 17 to 37); LR 10% (95% CI, 7 to 14). 6-month relapse rates were as follows: Training set (FIG. 2D): HR 20% (95% CI, 13 to 29); LR 20% (95% CI, 17 to 24); Test set (FIG. 2E): HR 17% (95% CI, 8 to 28); LR 19% (95% CI, 15 to 24); Validation set (FIG. 2F): HR 14% (95% CI, 7 to 23); LR 15% (95% CI, 11 to 19). 6-month overall survival rates were as follows: Training set (FIG. 2G): HR 60% (95% CI, 51 to 70); LR 84% (95% CI, 80 to 87); Test set (FIG. 2H): HR 57% (95% CI, 45 to 72); LR 81% (95% CI, 77 to 86); Validation set (FIG. 2I): HR 68% (95% CI, 58 to 80); LR 85% (95% CI, 81 to 89).

(FIG. 3B) HLA-Matched: HR 26% (95% CI, 20 to 33); LR 7% (95% CI, 5 to 9); HLA-Mismatched: HR 39% (95% CI, 26 to 53); LR 13% (95% CI, 9 to 18); and (FIG. 3C) Reduced-intensity conditioning: HR 37% (95% CI, 26 to 48); LR 8% (95% CI, 6 to 11); Full-intensity conditioning: HR 25% (95% CI, 19 to 32); LR 8% (95% CI, 6 to 10); (FIG. 3D) Age<21: HR 27% (95% CI, 11 to 47); LR 6% (95% CI, 3 to 11); Age>21:HR 29% (95% CI, 23 to 36); LR 8% (95% CI, 7 to 10).

(FIG. 4A) Training set: HR 18% vs LR 5%, p<0.001. (FIG. 4B) Test set: HR 24% vs LR 4%, p<0.001. (FIG. 4C) Validation set: HR 14% vs LR 5%, p<0.001. The chi-squared test was used to compare proportions between groups.

(FIG. 13A) Test cohort (n=236). 12-month cumulative incidence of non-relapse mortality (ETS 20% vs ETR 42%, p<0.001), overall survival (ETS 63% vs ETR 51%, p=0.02) and proportion of patients resistant to treatment at week 4 (ETS 24% vs ETR 57%, p<0.001). (FIG. 13B) Validation cohort 1 (n=142). 12-month cumulative incidence of non-relapse mortality (ETS 13% vs ETR 41%, p<0.001), overall survival (ETS 72% vs ETR 50%, p=0.004) and proportion of patients resistant to treatment at Week 4 (ETS 39% vs ETR 59%, p=0.03). (FIG. 13C) Validation cohort 2 (n=129). 12-month cumulative incidence of non-relapse mortality (ETS 08% vs ETR 31%, p=0.001), overall survival (ETS 87% vs ETR 60%, p<0.001) and proportion of patients resistant to treatment at Week 4 (ETS 11% vs ETR 41%, p<0.001).

FIG. 14A-14C. Long-term outcomes by biomarker probabilities in early treatment resistant patients. Early treatment resistant patients were subdivided based on biomarker probabilities into low and high groups. (FIG. 14A) Test cohort of patients (n=122). 12-month cumulative incidence of non-relapse mortality (low 22% vs high 63%, p<0.001), overall survival (low 68% vs high 34%, p<0.001) and proportion of patients resistant to treatment at week 4 (low 33% vs high 82%, p<0.001). (B) Validation cohort 1 (n=80). 12-month cumulative incidence of non-relapse mortality (low 13% vs high 67%, p<0.001), overall survival (low 76% vs high 26%, p<0.001) and proportion of patients resistant to treatment at week 4 (low 45% vs high 71%, p=0.03). (C) Validation cohort 2 (n=68). 12-month cumulative incidence of non-relapse mortality (low 14% vs high 75%, p<0.001), overall survival (low 78% vs high 14%, p<0.001) and proportion of patients resistant to treatment at week 4 (low 29% vs high 68%, p=0.004).

FIG. 15A-15C. Long-term outcomes by biomarker probabilities in early treatment sensitive patients. Early treatment sensitive patients were subdivided based on biomarker probabilities into low and high groups. (FIG. 15A) Test cohort of patients (n=114). 12-month cumulative incidence of non-relapse mortality (low 11% vs high 41%, p<0.001), overall survival (low 70% vs high 47%, p=0.004) and proportion of patients resistant to treatment at week 4 (low 18% vs high 38%, p=0.06). (FIG. 15B) Validation cohort 1 (n=62). 12-month cumulative incidence of non-relapse mortality (low 6% vs high 33%, p=0.005), overall survival (low 79% vs high 53%, p=0.03) and proportion of patients resistant to treatment at week 4 (low 30% vs high 67%, p=0.03). (FIG. 15C) Validation cohort 2 (n=61). 12-month cumulative incidence of non-relapse mortality (low 6% vs high 20%, p=0.46), overall survival (low 88% vs high 80%, p=0.80) and proportion of patients resistant to treatment at week 4 (low 8% vs high 28%, p=0.18).

(FIG. 16A) Forest plots. Left panel: Effect of early treatment resistance, Minnesota high risk and high biomarker probability status on odds of resistance to treatment at week 4. Right panel: Effect of early treatment resistance, Minnesota high risk and high biomarker probability status on hazard of non-relapse mortality at one year. Data are ratios and 95% confidence intervals. (FIG. 16B) Receiver operating characteristic curves were able to predict non-relapse mortality. Curves are shown for early treatment response, biomarker probabilities, and Minnesota risk. The diamond indicates the threshold that defined low versus high risk groups. Area under the curve (AUC) for early treatment response=0.67; for Minnesota risk=0.65; for biomarker probability=0.82; p-value for the comparison is 0.004. PPV=positive predictive value, NPV=negative predictive value.

FIG. 18A shows that unsupervised K-medoid clustering identified a threshold value of $\hat{p}$=0.291 that maximized the difference between groups while minimizing the differences in probabilities within each group. This clustering was performed without consideration of whether the patient did (o) or did not (x) experience NRM by 6 months following HCT. Patients with a $\hat{p} \leq 0.291$ were categorized as low probability, (n=143) and patients with a $\hat{p}$>0.291 were categorized as high probability (n=93) for subsequent analyses. FIG. 18B shows mean probability values in the low and high groups (low 0.18 vs high 0.45, p<0.001). Error bars are SEM.

DETAILED DESCRIPTION OF THE INVENTION

Figure 1:
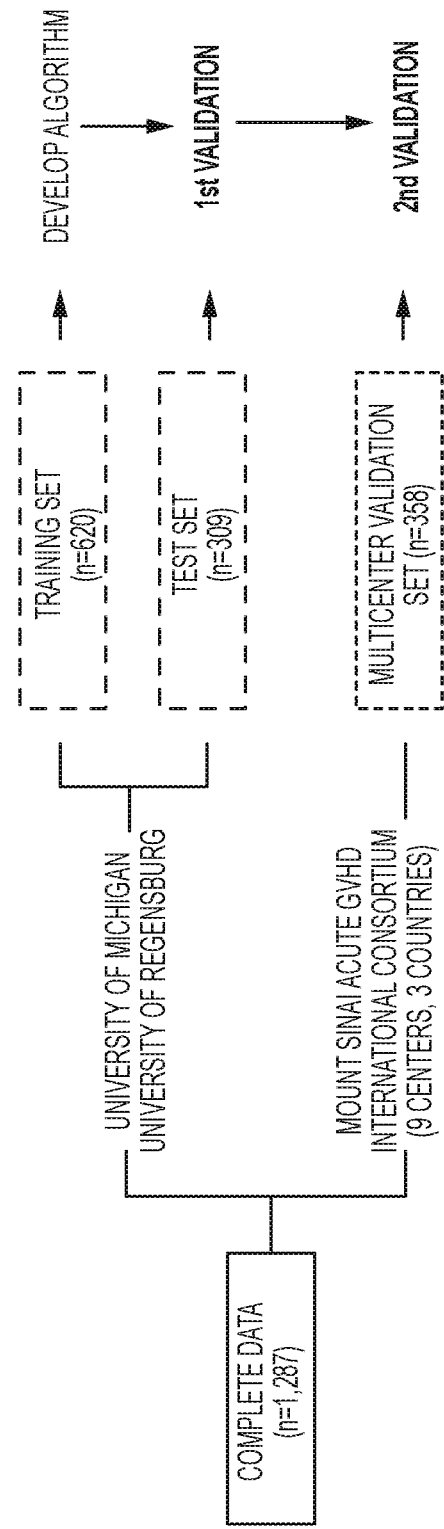
FIG. 1. Study Scheme of Algorithm Development and Validation. Clinical data and plasma samples from day 7±3 (e.g., day 5 to day 9) after HCT were available from 1,287 patients transplanted at 11 MAGIC centers. Patient samples from the two largest centers, the University of Michigan and the University of Regensburg, were randomly assigned to the training and test sets in a 2:1 proportion. The remaining 358 patients were assigned to the independent multicenter validation set. The training set alone (n=620) was used to develop the algorithm. All possible combinations of 1 to 4 biomarkers (ST2, Reg3α, TNFR1, and IL-2Rα) were used to model 6-month NRM by competing risks regression. Rigorous comparison of models through a Monte Carlo cross-validation of 75 different, randomly created training sets confirmed that the models using ST2 and REG3α was superior to all other biomarker combinations. This model was used to (i) predict the probability of 6-month NRM in the patients from the training set, (ii) rank order them from lowest to highest, and (iii) choose a threshold to separate risk groups for the final algorithm (see Examples below). The algorithm was then applied to the test set in a first validation and to the multicenter validation set in a second validation.
Figure 3A:
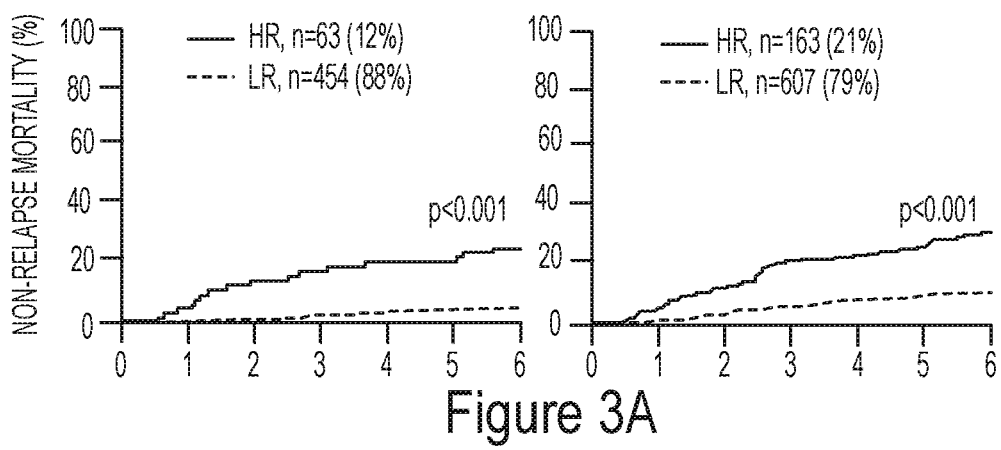
FIG. 3A-3D. MAGIC Risk Groups. 6-month cumulative incidence of non-relapse mortality of all patients (n=1287) by (FIG. 3A) Related donor: HR 26% (95% CI, 15 to 37); LR 5% (95% CI, 3 to 7); Unrelated donor: HR 30% (95% CI, 23 to 37); LR 10% (95% CI, 8 to 13)
Figure 3B:
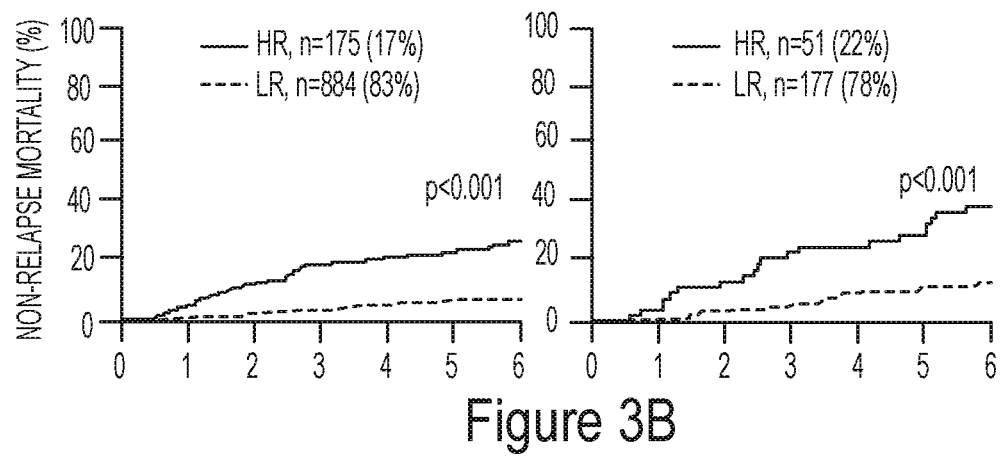
Figure 3C:
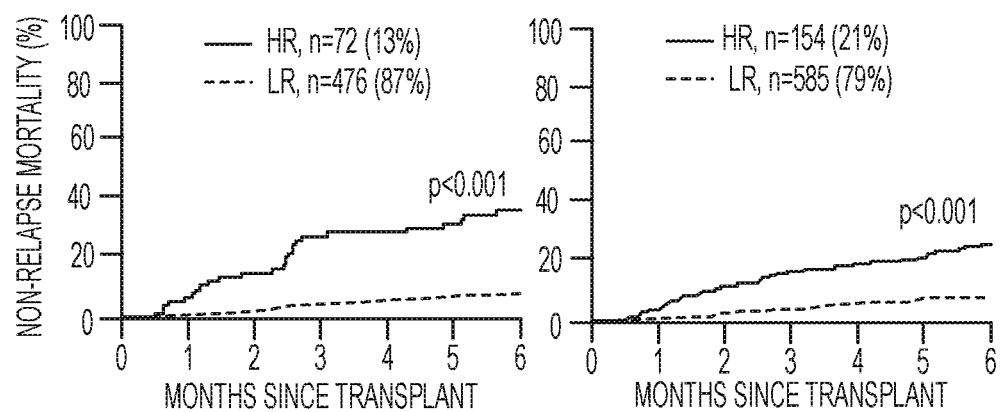
Figure 3D:
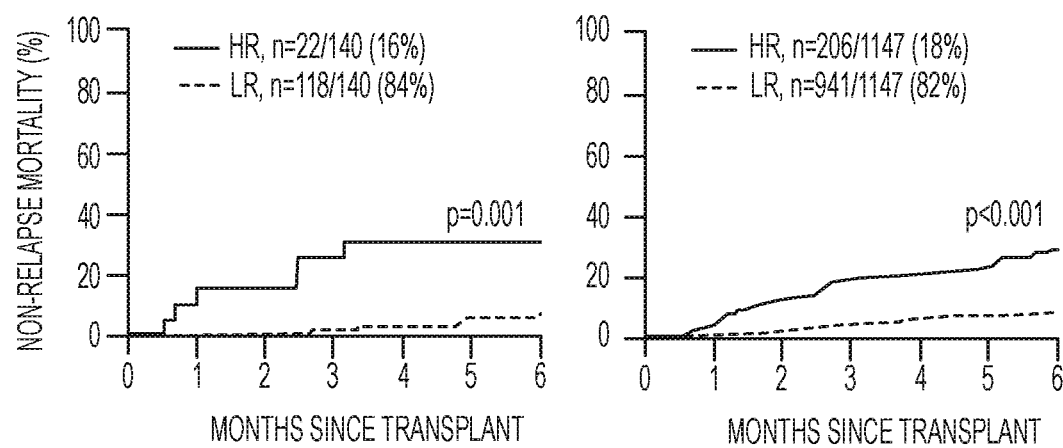

As specified in the Background Section, there is a great need in the art to identify technologies for reliable, consistent and simple diagnosis and classification of a patient's risk of developing GVHD, including severe or lethal GVHD, soon after receiving HCT but before clinical onset of symptoms, and use this understanding to develop novel diagnostic methods and kits. There is also a great need in the art to identify technologies for reliable, consistent and simple diagnosis and classification of a patient's risk of developing TA GVHD, including severe or lethal TA GVHD, soon after receiving transfusion or transplantation but before clinical onset of symptoms, and use this understanding to develop novel diagnostic methods and kits. The present invention satisfies this and other needs. Embodiments of the present invention relate generally to methods for diagnosis, classification and monitoring of GVHD and TA GVHD, including but not limited to severe or lethal GVHD and TA GVHD, well before the symptoms of GVHD or TA GVHD begin to appear. In some embodiments, the patient has treatment-resistant GVHD, such as for example and not limitation, GVHD that is resistant to high dose systemic corticosteroid therapies. In some embodiments, the patient can be tested at multiple time points after receiving HCT to monitor development of GVHD or TA GVHD, such as for example and not limitation, patients who are determined to be at low risk for developing GVHD or TA GVHD at an early time point. In some embodiments, a first blood sample is taken from the patient about 7 days after receiving HCT, and a second blood sample is taken from the patient about 14 days after receiving HCT.

Definitions

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or examples. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," and the like, "primary," "secondary," and the like, do not denote any order, quantity, or importance, but rather are used to distinguish one element from another.

As used herein, the term "and/or" may mean "and," it may mean "or," it may mean "exclusive-or," it may mean "one," it may mean "some, but not all," it may mean "neither," and/or it may mean "both." The term "or" is intended to mean an inclusive "or."

It is noted that terms like "specifically," "preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. Any dimensions listed in the various drawings are for illustrative purposes only and are not intended to be limiting. Other dimensions and proportions are contemplated and intended to be included within the scope of the invention.

As used herein, the term "subject" or "patient" refers to mammals and includes, without limitation, human and veterinary animals. In a preferred embodiment, the subject is human.

The terms "treat" or "treatment" of a state, disorder or condition include: (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985); *Transcription and Translation* (B. D. Hames & S. J. Higgins, eds. (1984); *Animal Cell Culture* (R. I. Freshney, ed. (1986); *Immobilized Cells and Enzymes* (IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994); among others.

After bone marrow transplantation, T cells present in the graft, either as contaminants or intentionally introduced into the host, attack the tissues of the transplant recipient after perceiving host tissues as antigenically foreign. The T cells produce an excess of cytokines, including TNF-a and interferon-gamma (IFNv). A wide range of host antigens can initiate GVHD, among them the human leukocyte antigens (HLAs). However, GVHD can occur even when HLA-identical siblings are the donors. HLA-identical siblings or HLA-identical unrelated donors often have genetically different proteins (called minor histocompatibility antigens) that can be presented by major histocompatibility complex (MHC) molecules to the donor's T-cells, which see these antigens as foreign and so mount an immune response.

GVHD may be classified as acute or chronic GVHD. In the classical sense, acute GVHD is characterized by selective damage to organs and tissues including, but not limited to, the liver, skin (rash), mucosa, and gastrointestinal (GI) tract. Chronic GVHD also attacks the above organs, but over its long-term course also is known to cause damage to the connective tissue and exocrine glands. GI GVHD can result in severe intestinal inflammation, sloughing of the mucosal membrane, severe or high-volume diarrhea, gastrointestinal bleeding, abdominal pain, nausea, anorexia and vomiting. GI GVHD has typically been diagnosed via intestinal biopsy.

Acute GVHD is staged as follows: overall grade (skin-liver-gut) with each organ staged individually from a low of 1 to a high of 4. A human subject with grade 4 GVHD usually has a poor prognosis. If the GVHD is severe and requires intense immunosuppression involving steroids and additional agents to get it under control, a subject may develop severe infections as a result of the immunosuppression and may die of infection.

Once it is known whether the patient is at risk for developing severe or fatal GVHD, such knowledge can guide the intensity and duration of treatment and minimize the toxicity associated with chronic steroid administration, as such steroid administration will be of more therapeutic benefit in less severe cases of GVHD. The ability to identify patients who will likely not respond to traditional steroid treatment and who are at particularly high risk for morbidity and mortality related to severe GVHD could permit tailored treatment plans, such as additional immunosuppressive treatments and/or prophylactic measures, which may be more effective if introduced early. If the patient is not identified as being at high risk for developing severe GVHD, such patient is more likely suitable for therapeutic regimens suited for less severe GVHD, and may tolerate a more rapid tapering of steroid regimens to reduce long-term toxicity, infections, and a loss of the graft versus leukemia effect. Follow-up biomarker monitoring in patients at risk of developing severe GVHD could also help decide whether to taper or alter the treatment/prophylaxis, and allow monitoring of the success of the treatment/prophylaxis throughout the therapy's duration.

Regenerating islet-derived 3-alpha (REG3α), a C-type lectin secreted by Paneth cells, was identified herein as a biomarker specific for lower GI GVHD through an unbiased, in-depth tandem MS-based discovery approach that can quantify proteins at low concentrations. REG proteins act downstream of IL-22 to protect the epithelial barrier function of the intestinal mucosa through the binding of bacterial peptidoglycans. Intestinal stem cells (ISCs) are principal cellular targets of GVHD in the GI tract, where intestinal flora are critical for amplification of GVHD damage. Without being bound by theory, a leading hypothesis is that ISCs are protected by anti-bacterial proteins, such as REG3α, secreted by neighboring Paneth cells into the crypt microenvironment. If death of an ISC eventually manifests itself as denudation of the mucosa, the patchy nature of GVHD histologic damage may be explained as the lack of mucosal regeneration following the dropout of individual ISCs. REG3α reduces the inflammation of human intestinal crypts in vitro, and its administration protects ISCs and prevents GI epithelial damage in vivo, raising interesting therapeutic possibilities for this molecule.

REG3α protein plasma concentrations correlate with disease activity in inflammatory bowel disease, and can distinguish infectious and autoimmune causes of diarrhea. Without being bound by theory, correlation of mucosal denudation (histologic grade 4) with high REG3α concentrations suggests that microscopic breaches in the mucosal epithelial barrier caused by severe GVHD permit REG3α to traverse into the systemic circulation. The tight proximity of Paneth cells with ISCs concentrates their secretory contents in that vicinity, so that mucosal barrier disruption caused by stem cell dropout may preferentially allow Paneth cell secretions, including REG3α, to traverse into the bloodstream. It is hypothesized that plasma levels of REG3α may therefore serve as a surrogate marker for the cumulative area of these breaches to GI mucosal barrier integrity, a parameter impossible to measure by individual tissue biopsies. Without being bound by theory, such an estimate of total damage to the mucosal barrier may also help explain the prognostic value of REG3α with respect to therapy responsiveness and NRM.

ST2 is the IL33 receptor, a member of the IL1/Toll-like receptor superfamily. ST2 promotes a Th2-type immune response in diseases, such as arthritis and asthma (Kakkar et al., Nature Reviews Drug Discovery 7: 827-40, 2008).

Improvements in survival following allogeneic hematopoietic cell transplantation (HCT) have led to its increasing use to cure hematologic malignancies and other disorders' but the leading cause of non-relapse mortality (NRM) after HCT remains graft-vs-host disease (GVHD).[2,41] Responses to primary therapy, high dose systemic corticosteroids, have not improved and survival for patients with treatment resistant GVHD remains particularly poor.[38] The clinical response after four weeks of treatment is a validated surrogate for long term survival[39], but physicians usually cannot wait one month before deciding whether to modify therapy, particularly for patients who do not achieve or maintain a convincing clinical response. In clinical practice, the period of one week of treatment is commonly used to determine escalation or de-escalation of immunosuppressive therapy but this early response correlates poorly with long-term outcomes[40]. Patient who do not respond early to systemic steroids have a generally poor prognosis but results are inconsistent among transplant centers and biomarkers that accurately predict long term outcomes in this highly immunosuppressed population are urgently needed.

Diagnostic Methods of the Invention

In one aspect, the present invention provides a method for determining the risk of developing severe or lethal GVHD in a subject who has recently undergone HCT, comprising the steps of:

a) measuring level(s) of at least one of ST2 and Reg3α in a first blood sample collected from the subject;

b) analyzing the level(s) according to the algorithm log$[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) being at risk for developing severe or lethal GVHD when the first $\hat{p}$ value is greater than or equal to the optimal classification threshold or (ii) not being at risk for developing severe or lethal GVHD when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In one aspect, the present invention provides a method for predicting the risk of developing severe or lethal GVHD in a subject who has recently undergone HCT, comprising the steps of:

a) measuring level(s) of at least one of ST2 and Reg3α in a first blood sample collected from the subject;

b) analyzing the level(s) according to the algorithm log$[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) being at risk for developing severe or lethal severe or lethal GVHD when the first $\hat{p}$ value is greater than or equal to the optimal classification threshold or (ii) not being at risk for developing severe or lethal severe or lethal GVHD when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In one aspect, the present invention provides a method for predicting severe or lethal GVHD in a subject who has recently undergone HCT, comprising the steps of:

a) measuring level(s) of at least one of ST2 and Reg3α in a first blood sample collected from the subject;

b) analyzing the level(s) according to the algorithm log$[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) being at risk for developing severe or lethal GVHD when the first $\hat{p}$ value is greater than or equal to the optimal classification threshold or (ii) not being at risk for developing severe or lethal GVHD when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In one aspect, the present invention provides a method for predicting a subject's response to a treatment for severe or lethal GVHD in a subject who has recently undergone HCT, comprising the steps of:

a) measuring level(s) of at least one of ST2 and Reg3α in a first blood sample collected from the subject;

b) analyzing the level(s) according to the algorithm log$[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold;

e) identifying the subject as (i) being at risk for developing severe or lethal GVHD when the first $\hat{p}$ value is greater than or equal to the optimal classification threshold or (ii)

not being at risk for developing severe or lethal GVHD when the first $\hat{p}$ value is less than the optimal classification threshold; and (f) predicting the subject's response to the treatment for severe or lethal GVHD based on the identification step.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In one aspect, the present invention provides a method for diagnosing severe or lethal GVHD in a subject who has recently undergone HCT, comprising the steps of:

a) measuring level(s) of at least one of ST2 and Reg3α in a first blood sample collected from the subject;

b) analyzing the level(s) according to the algorithm log $[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) having severe or lethal GVHD when the first $\hat{p}$ value is greater than or equal to the optimal classification threshold or (ii) not having severe or lethal GVHD when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In another aspect, the present invention provides a method for determining susceptibility of developing severe or lethal GVHD in a subject who has recently undergone HCT, comprising the steps of:

a) measuring level(s) of at least one of ST2 and Reg3α in a first blood sample collected from the subject;

b) analyzing the level(s) according to the algorithm log $[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold;

e) identifying the subject as (i) susceptible to developing severe or lethal GVHD when the first $\hat{p}$ value is greater than or equal to the optimal classification threshold or (ii) not susceptible to developing severe or lethal GVHD when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In another aspect, the present invention provides a method for detection of severe or lethal GVHD or the potential to develop severe or lethal GVHD in a subject who has recently undergone HCT, comprising the steps of:

a) measuring level(s) of at least one of ST2 and Reg3α in a first blood sample collected from the subject;

b) analyzing the level(s) according to the algorithm log $[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to the optimal classification threshold; and e) identifying the subject as (i) having or being at risk for severe or lethal GVHD when the first $\hat{p}$ value is greater than or equal to the optimal classification threshold or (ii) not having or not being at risk for severe or lethal GVHD when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In one aspect, the present invention provides a method for differentially diagnosing severe or lethal GVHD from mild to moderate GVHD in a subject who has recently undergone HCT, comprising the steps of:

a) measuring level(s) of at least one of ST2 and Reg3α in a first blood sample collected from the subject;

b) analyzing the level(s) according to the algorithm log $[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) having or being at risk for severe or lethal GVHD when the first $\hat{p}$ value is greater than or equal to the optimal classification threshold or (ii) having or being at risk for mild to moderate GVHD when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In one aspect, the present invention provides a method for classifying a subject who has recently undergone HCT as having or being at risk for severe or lethal GVHD, comprising the steps of:

a) measuring level(s) of at least one of ST2 and Reg3α in a first blood sample collected from the subject;

b) analyzing the level(s) according to the algorithm log $[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) having or being at risk for severe or lethal GVHD when the first $\hat{p}$ value is greater than or equal to the optimal classification threshold or (ii) not having or not being at risk for severe or lethal GVHD when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In another aspect, the present invention provides a method for monitoring the potential to develop severe or lethal GVHD in a subject who has recently undergone HCT, comprising the steps of:

a) measuring level(s) of at least one of ST2 and Reg3α in a first blood sample collected from the subject within four to ten days after undergoing HCT;

b) analyzing the level(s) in the first blood sample according to the algorithm $\log[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold;

e) identifying the subject as (i) having or being at risk for severe or lethal GVHD when the first $\hat{p}$ value is greater than or equal to the optimal classification threshold or (ii) not having or not being at risk for have severe or lethal GVHD when the first $\hat{p}$ value is less than the optimal classification threshold;

f) measuring the level(s) of at least one of ST2 and Reg3α in a second blood sample collected from the subject more than eleven days after undergoing HCT;

g) analyzing the level(s) in the second blood sample according to the algorithm $\log[-\log(1-\hat{p})]=-11.263+1.844(\log ST2)+0.577(\log REG3\alpha)$;

h) determining a second $\hat{p}$ value for the subject;

i) comparing the second $\hat{p}$ value obtained from the measurement analysis to the optimal classification threshold and to the first $\hat{p}$ value;

j) identifying the subject as (i) continuing to have or be at risk for severe or lethal GVHD when the second $\hat{p}$ value is greater than or equal to the optimal classification threshold and/or when the second $\hat{p}$ value is the same as or greater than the first $\hat{p}$ value or (ii) not continuing to have or not continuing to be at risk of having severe or lethal GVHD when the first $\hat{p}$ value is less than the optimal classification threshold;

k) optionally modifying the patient's therapeutic or prophylactic regimen based on the identification in step j; and l) repeating steps f-j on subsequent days after HCT as determined by a physician.

In an embodiment of the foregoing method, the patient may have GVHD that is resistant to treatment, such as for example and not limitation, steroid therapies, such as for example and not limitation, high dose systemic corticosteroid therapies. In another embodiment, the patient can be tested at multiple time points after receiving HCT to monitor development of GVHD or TA GVHD, such as for example and not limitation, patients who are determined to be at low risk for developing GVHD or TA GVHD at an early time point. In another embodiment of the foregoing method, the first blood sample is collected about 7 days after the patient underwent HCT, and the second blood sample is collected about 14 days after the patient underwent HCT.

In another aspect, the present invention provides a method for monitoring severe or lethal GVHD in a subject who has recently undergone HCT, comprising the steps of:

a) measuring level(s) of at least one of ST2 and Reg3α in a first blood sample collected from the subject within four to ten days after undergoing HCT;

b) analyzing the level(s) in the first blood sample according to the algorithm $\log[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold;

e) identifying the subject as (i) having or being at risk for severe or lethal GVHD when the first $\hat{p}$ value is greater than or equal to the optimal classification threshold or (ii) not having or not being at risk for have severe or lethal GVHD when the first $\hat{p}$ value is less than the optimal classification threshold;

f) measuring the level(s) of at least one of ST2 and Reg3α in a second blood sample collected from the subject more than eleven days after undergoing HCT;

g) analyzing the level(s) in the second blood sample according to the algorithm $\log[-\log(1-\hat{p})]=-11.263+1.844(\log ST2)+0.577(\log REG3\alpha)$;

h) determining a second $\hat{p}$ value for the subject;

i) comparing the second $\hat{p}$ value obtained from the measurement analysis to the optimal classification threshold and to the first $\hat{p}$ value;

j) identifying the subject as (i) continuing to have or be at risk for severe or lethal GVHD when the second $\hat{p}$ value is greater than or equal to the optimal classification threshold and/or when the second $\hat{p}$ value is the same as or greater than the first $\hat{p}$ value or (ii) not continuing to have or not continuing to be at risk of having severe or lethal GVHD when the first $\hat{p}$ value is less than the optimal classification threshold;

k) optionally modifying the patient's therapeutic or prophylactic regimen based on the identification in step j; and l) repeating steps f-j on subsequent days after HCT as determined by a physician.

In an embodiment of the foregoing method, the patient may have GVHD that is resistant to treatment, such as for example and not limitation, steroid therapies, such as for example and not limitation, high dose systemic corticosteroid therapies. In another embodiment, the patient can be tested at multiple time points after receiving HCT to monitor development of GVHD or TA GVHD, such as for example and not limitation, patients who are determined to be at low risk for developing GVHD or TA GVHD at an early time point. In another embodiment of the foregoing method, the first blood sample is collected about 7 days after the patient underwent HCT, and the second blood sample is collected about 14 days after the patient underwent HCT.

In one aspect, the present invention provides a method for monitoring the success and/or efficacy of treatment and/or prophylaxis of a subject who has recently undergone HCT and has or has been identified as likely to have severe or lethal GVHD, comprising the steps of:

a) measuring level(s) of at least one of ST2 and Reg3α in a first blood sample collected from the subject within four to ten days after undergoing HCT;

b) analyzing the level(s) in the first blood sample according to the algorithm $\log[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to the optimal classification threshold;

e) identifying the treatment and/or prophylaxis as (i) being successful when the first $\hat{p}$ value is less than or equal to the optimal classification threshold or (ii) not successful when the first $\hat{p}$ value is greater than the optimal classification threshold; and optionally modifying the patient's therapeutic and/or prophylactic regimen based on the identification in step e; and further optionally:

f) measuring the level(s) of at least one of ST2 and Reg3α in a second blood sample collected from the subject more than eleven days after undergoing HCT;

g) analyzing the level(s) in the second blood sample according to the algorithm $\log[-\log(1-\hat{p})]=-11.263+1.844(\log ST2)+0.577(\log REG3\alpha)$;

h) determining a second $\hat{p}$ value for the subject;

i) comparing the second $\hat{p}$ value obtained from the measurement analysis to the optimal classification threshold and to the first $\hat{p}$ value;

j) identifying the treatment and/or prophylaxis as (i) successful when the second $\hat{p}$ value is less than or equal to the optimal classification threshold and/or when the second $\hat{p}$ value is less than the first $\hat{p}$ value or (ii) not successful when the second $\hat{p}$ value is greater than or equal to the optimal classification threshold and/or when the second $\hat{p}$ value is greater than the first $\hat{p}$ value;

k) optionally modifying the patient's therapeutic or prophylactic regimen based on the identification in step j; and l) repeating steps f-j on subsequent days after HCT as determined by a physician.

In an embodiment of the foregoing method, the patient may have GVHD that is resistant to treatment, such as for example and not limitation, steroid therapies, such as for example and not limitation, high dose systemic corticosteroid therapies. In another embodiment, the patient can be tested at multiple time points after receiving HCT to monitor development of GVHD or TA GVHD, such as for example and not limitation, patients who are determined to be at low risk for developing GVHD or TA GVHD at an early time point. In another embodiment of the foregoing method, the first blood sample is collected about 7 days after the patient underwent HCT, and the second blood sample is collected about 14 days after the patient underwent HCT.

In another aspect, the present invention provides a method for selecting a subject for a treatment and/or prophylaxis of severe or lethal GVHD, comprising the steps of:

a) measuring level(s) of at least one of ST2 and Reg3α in a first blood sample collected from the subject;

b) analyzing the level(s) according to the algorithm log $[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) being suitable for the treatment and/or prophylaxis when the first $\hat{p}$ value is greater than or equal to the optimal classification threshold or (ii) not suitable for the treatment and/or prophylaxis when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In another aspect, the present invention provides a method for selecting a subject for a clinical trial for severe or lethal GVHD therapeutic and/or prophylactic compositions and/or methods, comprising the steps of:

a) measuring level(s) of at least one of ST2 and Reg3α in a first blood sample collected from the subject;

b) analyzing the level(s) according to the algorithm log $[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) being suitable for the clinical trial when the first $\hat{p}$ value is greater than or equal to the optimal classification threshold or (ii) not suitable for the clinical trial when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In another aspect, the present invention provides a method for treating and/or preventing severe or lethal GVHD in a subject who has recently undergone HCT, comprising the steps of:

a) measuring level(s) of at least one of ST2 and Reg3α in a first blood sample collected from the subject;

b) analyzing the level(s) according to the algorithm log $[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) being suitable for treatment or prophylaxis when the first $\hat{p}$ value is greater than or equal to the optimal classification threshold or (ii) not being suitable for treatment or prophylaxis when the first $\hat{p}$ value is less than the optimal classification threshold;

f) utilizing appropriate therapeutic and/or prophylactic compositions and/or methods if the subject has severe or lethal GVHD as identified in step e).

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In another method, the present invention provides for a method of prognosis of severe or lethal GVHD in a subject who has recently undergone HCT, comprising the steps of:

a) measuring level(s) of at least one of ST2 and Reg3α in a first blood sample collected from the subject;

b) analyzing the level(s) according to the algorithm log $[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) likely to develop severe or lethal GVHD when the first $\hat{p}$ value is greater than or equal to the optimal classification threshold or (ii) not likely to develop severe or lethal GVHD when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In another method, the present invention provides for a method for differentiating between severe or lethal GVHD and mild to moderate GVHD in a subject who has recently undergone HCT, comprising the steps of:

a) measuring level(s) of at least one of ST2 and Reg3α in a first blood sample collected from the subject;

b) analyzing the level(s) according to the algorithm log $[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to the optimal classification threshold; and e) identifying the subject as (i) having severe or lethal GVHD when the first $\hat{p}$ value is greater than or equal to the optimal classification threshold or (ii) having or likely to have mild to moderate GVHD when the p̂ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In any of the above methods, the patient is suffering from a high risk hematologic malignancy. In a preferred embodiment, the patient is suffering from leukemia, lymphoma, multiple myeloma, acute leukemia, acute myeloid leukemia, dysplastic condition, and/or acute lymphocytic leukemia (ALL). In another embodiment, the patient is suffering from a non-malignant genetic disorder of the blood or immune system (e.g., severe combined immunodeficiency, hemophagocytic lymphohistiocytosis (HLH), and hemoglobin disorders such as thalassemia, sickle cell anemia).

In any of the above methods, the optimal classification threshold is a p̂ value of greater than or equal to 0.12. In one embodiment, the optimal classification threshold is a p̂ value of greater than or equal to 0.13. In a preferred embodiment, the optimal classification threshold is a p̂ value of greater than or equal to 0.14. In a more preferred embodiment, the optimal classification threshold is a p̂ value of greater than or equal to 0.15. In a most preferred embodiment, the optimal classification threshold is a p̂ value of greater than or equal to 0.16.

In any of the above methods, the patient has received HCT at least four days before the first blood sample is collected. In any of the above methods, the patient has received HCT at most ten days before the first blood sample is collected. In any of the above methods, the patient has received HCT between four to ten days before the first blood sample is collected, including four days, five days, six days, seven days, eight days, nine days, and ten days. In a preferred embodiment of any of the above methods, the patient has received HCT seven days before the first blood sample is collected.

In any of the above methods comprising obtaining a subsequent blood sample(s) from the patient on day 11 or later after HCT, the subsequent blood sample(s) may be obtained from the patient on day 11 through the resolution of GVHD symptoms, including the onset of clinical symptoms of GVHD. Preferably, the subsequent blood sample(s) is obtained between days 14 to 21 after HCT.

In any of the above methods, particularly those comprising monitoring of treatment and/or prophylaxis of severe or lethal GVHD, at least one of the subsequent blood sample(s) may be obtained from the patient after the onset of clinical symptoms of GVHD. The subsequent p̂ value(s) obtained from the subsequent blood sample(s) may be compared to the patient's previous p̂ value(s) and/or the optimal classification threshold to determine efficacy of the treatment and/or prophylaxis. The treatment and/or prophylaxis may be modified accordingly.

In an embodiment of any of the foregoing methods, the patient may have GVHD that is resistant to treatment, such as for example and not limitation, steroid therapies, such as for example and not limitation, high dose systemic corticosteroid therapies. In another embodiment, the patient can be tested at multiple time points after receiving HCT to monitor development of GVHD or TA GVHD, such as for example and not limitation, patients who are determined to be at low risk for developing GVHD or TA GVHD at an early time point. In another embodiment of any of the foregoing methods, the first blood sample is collected about 7 days after the patient underwent HCT, and the second blood sample is collected about 14 days after the patient underwent HCT.

In one aspect, the present invention provides a method for determining the risk of developing severe or lethal TA GVHD in a subject who has recently undergone a transfusion or transplantation, comprising the steps of:

a) measuring level(s) of at least one of ST2 and Reg3α in a first blood sample collected from the subject;

b) analyzing the level(s) according to the algorithm log [−log(1−p̂)]=−11.263+1.844(log ST2)+0.577(log REG3α);

c) determining a first p̂ value for the subject;

d) comparing the first p̂ value obtained from the measurement analysis to an optimal classification threshold; and e) identifying the subject as (i) being at risk for developing severe or lethal TA GVHD when the first p̂ value is greater than or equal to the optimal classification threshold or (ii) not being at risk for developing severe or lethal TA GVHD when the first p̂ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In one aspect, the present invention provides a method for predicting the risk of developing severe or lethal TA GVHD in a subject who has recently undergone a transfusion or transplantation, comprising the steps of:

a) measuring level(s) of at least one of ST2 and Reg3α in a first blood sample collected from the subject;

b) analyzing the level(s) according to the algorithm log [−log(1−p̂)]=−11.263+1.844(log ST2)+0.577(log REG3α);

c) determining a first p̂ value for the subject;

d) comparing the first p̂ value obtained from the measurement analysis to an optimal classification threshold; and e) identifying the subject as (i) being at risk for developing severe or lethal severe or lethal TA GVHD when the first p̂ value is greater than or equal to the optimal classification threshold or (ii) not being at risk for developing severe or lethal severe or lethal TA GVHD when the first p̂ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In one aspect, the present invention provides a method for predicting severe or lethal TA GVHD in a subject who has recently undergone a transfusion or transplantation, comprising the steps of:

a) measuring level(s) of at least one of ST2 and Reg3α in a first blood sample collected from the subject;

b) analyzing the level(s) according to the algorithm log [−log(1−p̂)]=−11.263+1.844(log ST2)+0.577(log REG3α);

c) determining a first p̂ value for the subject;

d) comparing the first p̂ value obtained from the measurement analysis to an optimal classification threshold; and e) identifying the subject as (i) being at risk for developing severe or lethal TA GVHD when the first p̂ value is greater than or equal to the optimal classification threshold or (ii) not being at risk for developing severe or lethal TA GVHD when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In one aspect, the present invention provides a method for predicting a subject's response to a treatment for severe or lethal TA GVHD in a subject who has recently undergone a transfusion or transplantation, comprising the steps of:

a) measuring level(s) of at least one of ST2 and Reg3α in a first blood sample collected from the subject;
b) analyzing the level(s) according to the algorithm log $[-\log(1-\hat{p})]=-11.263+1.844(\log ST2)+0.577(\log REG3\alpha)$;
c) determining a first $\hat{p}$ value for the subject;
d) comparing the first $\hat{p}$ value obtained from the measurement analysis to an optimal classification threshold;
e) identifying the subject as (i) being at risk for developing severe or lethal TA GVHD when the first $\hat{p}$ value is greater than or equal to the optimal classification threshold or (ii) not being at risk for developing severe or lethal TA GVHD when the first $\hat{p}$ value is less than the optimal classification threshold; and
(f) predicting the subject's response to the treatment for severe or lethal TA GVHD based on the identification step.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In one aspect, the present invention provides a method for diagnosing severe or lethal TA GVHD in a subject who has recently undergone a transfusion or transplantation, comprising the steps of:

a) measuring level(s) of at least one of ST2 and Reg3α in a first blood sample collected from the subject;
b) analyzing the level(s) according to the algorithm log $[-\log(1-\hat{p})]=-11.263+1.844(\log ST2)+0.577(\log REG3\alpha)$;
c) determining a first $\hat{p}$ value for the subject;
d) comparing the first $\hat{p}$ value obtained from the measurement analysis to an optimal classification threshold; and
e) identifying the subject as (i) having severe or lethal TA GVHD when the first $\hat{p}$ value is greater than or equal to the optimal classification threshold or (ii) not having severe or lethal TA GVHD when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In another aspect, the present invention provides a method for determining susceptibility of developing severe or lethal TA GVHD in a subject who has recently undergone a transfusion or transplantation, comprising the steps of:

a) measuring level(s) of at least one of ST2 and Reg3α in a first blood sample collected from the subject;
b) analyzing the level(s) according to the algorithm log $[-\log(1-\hat{p})]=-11.263+1.844(\log ST2)+0.577(\log REG3\alpha)$;
c) determining a first $\hat{p}$ value for the subject;
d) comparing the first $\hat{p}$ value obtained from the measurement analysis to an optimal classification threshold;
e) identifying the subject as (i) susceptible to developing severe or lethal TA GVHD when the first $\hat{p}$ value is greater than or equal to the optimal classification threshold or (ii) not susceptible to developing severe or lethal TA GVHD when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In another aspect, the present invention provides a method for detection of severe or lethal TA GVHD in a subject who has recently undergone a transfusion or transplantation, comprising the steps of:

a) measuring level(s) of at least one of ST2 and Reg3α in a first blood sample collected from the subject;
b) analyzing the level(s) according to the algorithm log $[-\log(1-\hat{p})]=-11.263+1.844(\log ST2)+0.577(\log REG3\alpha)$;
c) determining a first $\hat{p}$ value for the subject;
d) comparing the first $\hat{p}$ value obtained from the measurement analysis to the optimal classification threshold; and
e) identifying the subject as (i) having or being at risk for severe or lethal TA GVHD when the first $\hat{p}$ value is greater than or equal to the optimal classification threshold or (ii) not having or not being at risk for severe or lethal TA GVHD when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In one aspect, the present invention provides a method for differentially diagnosing severe or lethal TA GVHD from mild to moderate TA GVHD in a subject who has recently undergone a transfusion or transplantation, comprising the steps of:

a) measuring level(s) of at least one of ST2 and Reg3α in a first blood sample collected from the subject;
b) analyzing the level(s) according to the algorithm log $[-\log(1-\hat{p})]=-11.263+1.844(\log ST2)+0.577(\log REG3\alpha)$;
c) determining a first $\hat{p}$ value for the subject;
d) comparing the first $\hat{p}$ value obtained from the measurement analysis to an optimal classification threshold; and
e) identifying the subject as (i) having or being at risk for severe or lethal TA GVHD when the first $\hat{p}$ value is greater than or equal to the optimal classification threshold or (ii) having or being at risk for mild to moderate TA GVHD when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In one aspect, the present invention provides a method for classifying a subject who has recently undergone a transfusion or transplantation as having or being at risk for severe or lethal TA GVHD, comprising the steps of:

a) measuring level(s) of at least one of ST2 and Reg3α in a first blood sample collected from the subject;

b) analyzing the level(s) according to the algorithm $\log[-\log(1-\hat{p})] = -11.263 + 1.844(\log ST2) + 0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) having or being at risk for severe or lethal TA GVHD when the first $\hat{p}$ value is greater than or equal to the optimal classification threshold or (ii) not having or not being at risk for severe or lethal TA GVHD when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In another aspect, the present invention provides a method for monitoring the potential to develop severe or lethal TA GVHD in a subject who has recently undergone a transfusion or transplantation, comprising the steps of:

a) measuring level(s) of at least one of ST2 and Reg3α in a first blood sample collected from the subject within four to ten days after undergoing the transfusion or transplantation;

b) analyzing the level(s) in the first blood sample according to the algorithm $\log[-\log(1-\hat{p})] = -11.263 + 1.844(\log ST2) + 0.577(\log REG3\alpha)$;

c) determining a first $\hat{p}$ value for the subject;

d) comparing the first $\hat{p}$ value obtained from the measurement analysis to an optimal classification threshold;

e) identifying the subject as (i) having or being at risk for severe or lethal TA GVHD when the first $\hat{p}$ value is greater than or equal to the optimal classification threshold or (ii) not having or not being at risk for have severe or lethal TA GVHD when the first $\hat{p}$ value is less than the optimal classification threshold;

f) measuring the level(s) of at least one of ST2 and Reg3α in a second blood sample collected from the subject more than eleven days after undergoing the transfusion or transplantation;

g) analyzing the level(s) in the second blood sample according to the algorithm $\log[-\log(1-\hat{p})] = -11.263 + 1.844(\log ST2) + 0.577(\log REG3\alpha)$;

h) determining a second $\hat{p}$ value for the subject;

i) comparing the second $\hat{p}$ value obtained from the measurement analysis to the optimal classification threshold and to the first $\hat{p}$ value;

j) identifying the subject as (i) continuing to have or be at risk for severe or lethal TA GVHD when the second $\hat{p}$ value is greater than or equal to the optimal classification threshold and/or when the second $\hat{p}$ value is the same as or greater than the first $\hat{p}$ value or (ii) not continuing to have or not continuing to be at risk of having severe or lethal TA GVHD when the first $\hat{p}$ value is less than the optimal classification threshold;

k) optionally modifying the patient's therapeutic or prophylactic regimen based on the identification in step j; and l) repeating steps f-j on subsequent days after the transfusion or transplantation as determined by a physician.

In an embodiment of the foregoing method, the patient may have GVHD that is resistant to treatment, such as for example and not limitation, steroid therapies, such as for example and not limitation, high dose systemic corticosteroid therapies. In another embodiment, the patient can be tested at multiple time points after receiving HCT to monitor development of GVHD or TA GVHD, such as for example and not limitation, patients who are determined to be at low risk for developing GVHD or TA GVHD at an early time point. In another embodiment of the foregoing method, the first blood sample is collected about 7 days after the patient underwent HCT, and the second blood sample is collected about 14 days after the patient underwent HCT.

In another aspect, the present invention provides a method for monitoring severe or lethal TA GVHD in a subject who has recently undergone a transfusion or transplantation, comprising the steps of:

a) measuring level(s) of at least one of ST2 and Reg3α in a first blood sample collected from the subject within four to ten days after undergoing the transfusion or transplantation;

b) analyzing the level(s) in the first blood sample according to the algorithm $\log[-\log(1-\hat{p})] = -11.263 + 1.844(\log ST2) + 0.577(\log REG3\alpha)$;

c) determining a first $\hat{p}$ value for the subject;

d) comparing the first $\hat{p}$ value obtained from the measurement analysis to an optimal classification threshold;

e) identifying the subject as (i) having or being at risk for severe or lethal TA GVHD when the first $\hat{p}$ value is greater than or equal to the optimal classification threshold or (ii) not having or not being at risk for have severe or lethal TA GVHD when the first $\hat{p}$ value is less than the optimal classification threshold;

f) measuring the level(s) of at least one of ST2 and Reg3α in a second blood sample collected from the subject more than eleven days after undergoing the transfusion or transplantation;

g) analyzing the level(s) in the second blood sample according to the algorithm $\log[-\log(1-\hat{p})] = -11.263 + 1.844(\log ST2) + 0.577(\log REG3\alpha)$;

h) determining a second $\hat{p}$ value for the subject;

i) comparing the second $\hat{p}$ value obtained from the measurement analysis to the optimal classification threshold and to the first $\hat{p}$ value;

j) identifying the subject as (i) continuing to have or be at risk for severe or lethal TA GVHD when the second $\hat{p}$ value is greater than or equal to the optimal classification threshold and/or when the second $\hat{p}$ value is the same as or greater than the first $\hat{p}$ value or (ii) not continuing to have or not continuing to be at risk of having severe or lethal TA GVHD when the first $\hat{p}$ value is less than the optimal classification threshold;

k) optionally modifying the patient's therapeutic or prophylactic regimen based on the identification in step j; and l) repeating steps f-j on subsequent days after the transfusion or transplantation as determined by a physician.

In an embodiment of the foregoing method, the patient may have GVHD that is resistant to treatment, such as for example and not limitation, steroid therapies, such as for example and not limitation, high dose systemic corticosteroid therapies. In another embodiment, the patient can be tested at multiple time points after receiving HCT to monitor development of GVHD or TA GVHD, such as for example and not limitation, patients who are determined to be at low risk for developing GVHD or TA GVHD at an early time point. In another embodiment of the foregoing method, the first blood sample is collected about 7 days after the patient underwent HCT, and the second blood sample is collected about 14 days after the patient underwent HCT.

In one aspect, the present invention provides a method for monitoring the success and/or efficacy of treatment and/or prophylaxis of a subject who has recently undergone a transfusion or transplantation and has or has been identified as likely to have severe or lethal TA GVHD, comprising the steps of:

a) measuring level(s) of at least one of ST2 and Reg3α in a first blood sample collected from the subject within four to ten days after undergoing the transfusion or transplantation;

b) analyzing the level(s) in the first blood sample according to the algorithm $\log[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to the optimal classification threshold;

e) identifying the treatment and/or prophylaxis as (i) being successful when the first $\hat{p}$ value is less than or equal to the optimal classification threshold or (ii) not successful when the first $\hat{p}$ value is greater than the optimal classification threshold; and optionally modifying the patient's therapeutic and/or prophylactic regimen based on the identification in step e; and further optionally:

f) measuring the level(s) of at least one of ST2 and Reg3α in a second blood sample collected from the subject more than eleven days after undergoing the transfusion or transplantation;

g) analyzing the level(s) in the second blood sample according to the algorithm $\log[-\log(1-\hat{p})]=-11.263+1.844(\log ST2)+0.577(\log REG3\alpha)$;

h) determining a second $\hat{p}$ value for the subject;

i) comparing the second $\hat{p}$ value obtained from the measurement analysis to the optimal classification threshold and to the first $\hat{p}$ value;

j) identifying the treatment and/or prophylaxis as (i) successful when the second $\hat{p}$ value is less than or equal to the optimal classification threshold and/or when the second $\hat{p}$ value is less than the first $\hat{p}$ value or (ii) not successful when the second $\hat{p}$ value is greater than or equal to the optimal classification threshold and/or when the second $\hat{p}$ value is greater than the first $\hat{p}$ value;

k) optionally modifying the patient's therapeutic or prophylactic regimen based on the identification in step j; and l) repeating steps f-j on subsequent days after the transfusion or transplantation as determined by a physician.

In an embodiment of the foregoing method, the patient may have GVHD that is resistant to treatment, such as for example and not limitation, steroid therapies, such as for example and not limitation, high dose systemic corticosteroid therapies. In another embodiment, the patient can be tested at multiple time points after receiving HCT to monitor development of GVHD or TA GVHD, such as for example and not limitation, patients who are determined to be at low risk for developing GVHD or TA GVHD at an early time point. In another embodiment of the foregoing method, the first blood sample is collected about 7 days after the patient underwent HCT, and the second blood sample is collected about 14 days after the patient underwent HCT.

In another aspect, the present invention provides a method for selecting a subject for a treatment and/or prophylaxis of severe or lethal TA GVHD, comprising the steps of:

a) measuring level(s) of at least one of ST2 and Reg3α in a first blood sample collected from the subject;

b) analyzing the level(s) according to the algorithm $\log[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) being suitable for the treatment and/or prophylaxis when the first $\hat{p}$ value is greater than or equal to the optimal classification threshold or (ii) not suitable for the treatment and/or prophylaxis when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In another aspect, the present invention provides a method for selecting a subject for a clinical trial for severe or lethal TA GVHD therapeutic and/or prophylactic compositions and/or methods, comprising the steps of:

a) measuring level(s) of at least one of ST2 and Reg3α in a first blood sample collected from the subject;

b) analyzing the level(s) according to the algorithm $\log[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) being suitable for the clinical trial when the first $\hat{p}$ value is greater than or equal to the optimal classification threshold or (ii) not suitable for the clinical trial when the first $\hat{p}$ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In another aspect, the present invention provides a method for treating and/or preventing severe or lethal TA GVHD in a subject who has recently undergone a transfusion or transplantation, comprising the steps of:

a) measuring level(s) of at least one of ST2 and Reg3α in a first blood sample collected from the subject;

b) analyzing the level(s) according to the algorithm $\log[-\log(1-\hat{p})]=-11.263+1.844(\log ST2)+0.577(\log REG3\alpha)$;

c) determining a first $\hat{p}$ value for the subject;

d) comparing the first $\hat{p}$ value obtained from the measurement analysis to an optimal classification threshold; and e) identifying the subject as (i) being suitable for treatment or prophylaxis when the first $\hat{p}$ value is greater than or equal to the optimal classification threshold or (ii) not being suitable for treatment or prophylaxis when the first $\hat{p}$ value is less than the optimal classification threshold;

f) utilizing appropriate therapeutic and/or prophylactic compositions and/or methods if the subject has severe or lethal TA GVHD as identified in step e).

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In another method, the present invention provides for a method of prognosis of severe or lethal TA GVHD in a subject who has recently undergone a transfusion or transplantation, comprising the steps of:

a) measuring level(s) of at least one of ST2 and Reg3α in a first blood sample collected from the subject;

b) analyzing the level(s) according to the algorithm $\log[-\log(1-\hat{p})]=-11.263+1.844(\log ST2)+0.577(\log REG3\alpha)$;

c) determining a first p̂ value for the subject;

d) comparing the first p̂ value obtained from the measurement analysis to an optimal classification threshold; and e) identifying the subject as (i) likely to develop severe or lethal TA GVHD when the first p̂ value is greater than or equal to the optimal classification threshold or (ii) not likely to develop severe or lethal TA GVHD when the first p̂ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In another method, the present invention provides for a method for differentiating between severe or lethal TA GVHD and mild to moderate TA GVHD in a subject who has recently undergone a transfusion or transplantation, comprising the steps of:

a) measuring level(s) of at least one of ST2 and Reg3α in a first blood sample collected from the subject;

b) analyzing the level(s) according to the algorithm log[−log(1−p̂)]=−11.263+1.844(log ST2)+0.577(log REG3α);

c) determining a first p̂ value for the subject;

d) comparing the first p̂ value obtained from the measurement analysis to the optimal classification threshold; and e) identifying the subject as (i) having severe or lethal TA GVHD when the first p̂ value is greater than or equal to the optimal classification threshold or (ii) having or likely to have mild to moderate TA GVHD when the p̂ value is less than the optimal classification threshold.

In an embodiment of the foregoing method, the patient may have GVHD that is resistant to treatment, such as for example and not limitation, steroid therapies, such as for example and not limitation, high dose systemic corticosteroid therapies. In another embodiment of the foregoing method, the first blood sample is collected about 7 days after the patient underwent HCT.

In any of the above methods, the patient has recently undergone a transfusion or transplantation involving the transfer of lymphocytes from a donor to the patient. In a preferred embodiment, the patient has recently undergone a directed blood transfusion, a small bowel transplantation, and/or a liver transplantation.

In any of the above methods, the optimal classification threshold is a p̂ value of greater than or equal to 0.12. In one embodiment, the optimal classification threshold is a p̂ value of greater than or equal to 0.13. In a preferred embodiment, the optimal classification threshold is a p̂ value of greater than or equal to 0.14. In a more preferred embodiment, the optimal classification threshold is a p̂ value of greater than or equal to 0.15. In a most preferred embodiment, the optimal classification threshold is a p̂ value of greater than or equal to 0.16.

In any of the above methods, the patient underwent the transfusion or transplantation at least four days before the first blood sample is collected. In any of the above methods, the patient underwent the transfusion or transplantation at most ten days before the first blood sample is collected. In any of the above methods, the patient underwent the transfusion or transplantation between four to ten days before the first blood sample is collected, including four days, five days, six days, seven days, eight days, nine days, and ten days. In a preferred embodiment of any of the above methods, the patient underwent the transfusion or transplantation seven days before the first blood sample is collected.

In any of the above methods comprising obtaining a subsequent blood sample(s) from the patient on day 11 or later after the transfusion or transplantation, the subsequent blood sample(s) may be obtained from the patient on day 11 through the resolution of TA GVHD symptoms, including the onset of clinical symptoms of TA GVHD. Preferably, the subsequent blood sample(s) is obtained between days 14 to 21 after the transfusion or transplantation.

In any of the above methods, particularly those comprising monitoring of treatment and/or prophylaxis of severe or lethal TA GVHD, at least one of the subsequent blood sample(s) may be obtained from the patient after the onset of clinical symptoms of TA GVHD. The subsequent p̂ value(s) obtained from the subsequent blood sample(s) may be compared to the patient's previous p̂ value(s) and/or the optimal classification threshold to determine efficacy of the treatment and/or prophylaxis. The treatment and/or prophylaxis may be modified accordingly.

In an embodiment of any of the foregoing methods, the patient may have GVHD that is resistant to treatment, such as for example and not limitation, steroid therapies, such as for example and not limitation, high dose systemic corticosteroid therapies. In another embodiment, the patient can be tested at multiple time points after receiving HCT to monitor development of GVHD or TA GVHD, such as for example and not limitation, patients who are determined to be at low risk for developing GVHD or TA GVHD at an early time point. In another embodiment of any of the foregoing methods, the first blood sample is collected about 7 days after the patient underwent HCT, and the second blood sample is collected about 14 days after the patient underwent HCT.

In any of the above methods, step (a) further comprises obtaining a blood sample from the patient and subsequently isolating at least one of ST2 and Reg3α. In one embodiment, the blood sample is a peripheral blood sample.

In any of the above methods, step (a) further comprises determining the levels of at least one of ST2 and Reg3α. In some embodiments, the levels of at least one of ST2 and Reg3α that are measured are expression levels of these markers. In some embodiments, the determination of the levels of at least one of ST2 and Reg3α further comprise isolating nucleic acid and/or protein from the sample. In some embodiments, the marker(s) is detected directly. In some of these embodiments, the marker detection comprises a method such as, for example and not limitation, Sanger sequencing, pyrosequencing, SOLID sequencing, massively parallel sequencing, barcoded DNA sequencing, PCR, real-time PCR, quantitative PCR, microarray analysis of the isolated nucleic acid with a gene chip, restriction fragment length polymorphism analysis, allele specific ligation, and comparative genomic hybridization. In other embodiments, the marker(s) is detected indirectly. In some of these embodiments, the marker detection comprises a method such as, for example and not limitation, microarray/microchip analysis of the isolated nucleic acid, DNA/RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, flow cytometry, bead-based flow-cytometry, immunohistochemistry, ELISA, RIA, Western blot, immunoaffinity chromatograpy, HPLC, mass spectrometry, mass spectroscopy, protein microarray/microchip analysis, PAGE analysis, isoelectric focusing, immunoturbidimetry, rapid immunodiffusion, laser nephelometry, visual agglutination, quantitative Western blot analysis, multiple reaction monitoring-mass spectrometry (MRM Proteomics), Lowry assay, Bradford assay, BCA assay, UV spectroscopic assays, and 2-D gel electrophoresis.

In any of the above methods, the onset of clinical symptoms of GVHD include nausea, vomiting, anorexia, secretory diarrhea and, in more severe cases, abdominal pain and/or hemorrhage. Diagnosis of GVHD may be confirmed by biopsy and the clinical stage of the GVHD can be subsequently assigned.

In any of the foregoing methods, steps (b) and/or (c) and/or (d) and/or (e) (and repetitions of such steps) are performed by a computer, as described further herein. In certain embodiments, it may be convenient to prepare a report of results of the patient's identification. Thus, certain embodiments of the methods of the disclosure comprise a further step of preparing a report containing results from the identification, wherein said report is written in a computer readable medium, printed on paper, or displayed on a visual display. In certain embodiments, it may be convenient to report results of susceptibility to severe GVHD to at least one entity selected from the group consisting of the subject, a guardian of the subject, a physician, a medical organization, and a medical insurer. In other embodiments, it may be convenient to report prognosis, results of monitoring, and/or efficacy of treatment and/or prophylactic methods to such entity.

In a particularly preferred embodiment of any of the above methods, the markers analyzed are REG3α and ST2.

Therapeutic and/or Prophylactic Methods

In any of the foregoing methods, the method may further comprise treatment and/or prophylaxis of patients determined to have, or be at risk for having, severe or lethal GHVD. Alternatively, the method of treatment and/or prophylaxis may comprise detection of the biomarkers and their use in the described algorithm to identify patients having or being at risk of having severe or lethal GVHD, and initiating treatment and/or prophylaxis based on the identification, or being suitable for undergoing such therapies.

In some embodiments, the treatment and/or prophylaxis comprises administration of appropriate therapeutically effective pharmaceutical compositions and/or use of appropriate therapeutically effective methods.

In an embodiment of any of the foregoing method, the patient may have GVHD that is resistant to treatment, such as for example and not limitation, steroid therapies, such as for example and not limitation, high dose systemic corticosteroid therapies.

In an embodiment of any of the foregoing methods, the patient can be tested at multiple time points after receiving HCT to monitor development of GVHD or TA GVHD, such as for example and not limitation, patients who are determined to be at low risk for developing GVHD or TA GVHD at an early time point. In another embodiment of any of the foregoing methods, the first blood sample is collected about 7 days after the patient underwent HCT, and the second blood sample is collected about 14 days after the patient underwent HCT.

Prophylactic compositions and methods include, for example and not limitation, immunosuppressive drugs, calcineurin inhibitors, high doses of steroids (e.g., corticosteroids such as for example and not limitation, prednisone, methylprednisolone, and the like), selective depletion of alloreactive T lymphocytes from the donor graft, the use of umbilical cord blood as a source of donor cells, and choosing more closely HLA-matched donors.

Severe GVHD is generally treated with high-dose steroids and/or immunosuppressive therapies, including treatment with high-dose steroids in combination with immunosuppressive therapies. Steroids suitable for treatment of severe GVHD comprise, for example and not limitation, corticosteroids (e.g., prednisone, prednisolone, methylprednisolone, and the like). Immunosuppressive therapy comprises, for example and not limitation, cyclosporine, tacrolimus (also known as FK-506 or Fujimycin), methotrexate, mycophenoate mofetil, antithymocyte globulin (ATG), monoclonal antibodies (e.g., anti-CD3, -CD5, and -IL-2 antibodies, anti-CD20 (rituximab), and alemtuzumab (Campath)), anti-TNF drugs (e.g., etanercept (Enbrel®), infliximab, adlimumab), lymphocyte immune globulin (Atgam®), sirolimus, ustekinumab, extracorporeal photophoresis (ECP), anti-CD3 drugs (e.g.,Visilizumab and OKT3), anti-CD5 drug and anti-IL-2 (CD25) drugs (inolimomab, basiliximab, daclizumab, and denileukin diftitox), anti-CD147 drugs (e.g., Alefacept), anti-IL1 R drugs, (e.g., Anakinra), anti-integrin drugs (e.g., α4β7 antagonist vedolizumab (Entyvio®), α4 antagonist natalizumab (Tysabri®), and β7 antagonist etrolizumab), mesenchymal stem cells, and regulatory T cells. The list of drugs provided herein above is not meant to be limiting as a person skilled in the art is aware of the many available treatment options for GVHD including severe or lethal GVHD. Additional methods of treatment for GVHD suitable for use in the present invention are discussed by Blazar et al. in Nature Reviews Immunology 12: 443-58, 2012.

The GVHD treatment and/or prophylaxis may be administered to the subject via any suitable route of administration. The effective amount or dose of GVHD treatment and/or prophylaxis administered should be sufficient to provide a therapeutic or prophylactic response in the subject over a reasonable time frame. For example, the dose of immunosuppressive drug should be sufficient to decrease symptoms of severe GVHD along with decreasing (i) the level of any of the biomarkers described herein as being associated with severe GVHD and/or (ii) a $\hat{p}$ value. The dose will be determined by the efficacy of the particular active agent and the condition of the subject (e.g., human), as well as the body weight of the subject (e.g., human) to be treated.

In any of the foregoing embodiments, the patient may have GVHD that is resistant to treatment, such as for example and not limitation, steroid therapies, such as for example and not limitation, high dose systemic corticosteroid therapies.

Kits of the Invention

The present invention also provides kits useful in the practice of the methods of the invention. In some embodiments, these kits comprise detection reagents that specifically bind the biomarkers of the present invention, such as for example and not limitation, at least one of ST2 and Reg3α. The kits typically include a probe that comprises an antibody or nucleic acid sequence that specifically binds to polypeptides or polynucleotides of the invention, such as for example and not limitation, at least one of ST2 and Reg3α as well as genes encoding these biomarkers, and a label for detecting the presence of the probe. The kits may include several antibodies specific for, or polynucleotide sequences encoding, the polypeptides of the invention. The kits may further comprise control probes for detection of a control nucleic acid or a control protein in order to provide a control level of the nucleic acid or protein, and/or other standards or controls. The probe is optionally detectably labeled.

The kit may contain in separate containers a nucleic acid or antibody (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions for carrying out the assay may also be included in the kit. The assay may, for example and not limitation, be in the form of a Northern hybridization, sandwich ELISA or protein antibody array.

Reagents for detecting biomarkers of the present invention can be immobilized on a solid matrix such as a porous strip to form at least one biomarker detection site. The measurement or detection region of the porous strip may include a plurality of sites containing an antibody or nucleic acid. A test strip may also contain sites for negative and/or positive controls. Alternatively, control sites can be located on a separate strip from the test strip. Optionally, the different detection sites may contain different amounts of immobilized antibodies or nucleic acids, e.g., a higher amount in the first detection site and lesser amounts in subsequent sites. Upon the addition of test sample, the number of sites displaying a detectable signal provides a quantitative indication of the amount of biomarker present in the sample. The detection sites may be configured in any suitably detectable shape and are typically in the shape of a bar or dot spanning the width of a test strip.

Alternatively, the kit contains a nucleic acid substrate array comprising one or more nucleic acid sequences. The nucleic acids on the array specifically identify one or more nucleic acid sequences adapted to bind a nucleic acid sequence encoding a biomarker in Table 1 or 2. The substrate array can be on, e.g., a solid substrate or "chip". Alternatively, the substrate array can be a solution array.

A kit of the invention can also provide reagents for primer extension and amplification reactions. For example, in some embodiments, the kit may further include one or more of the following components: a reverse transcriptase enzyme, a DNA polymerase enzyme (such as, e.g., a thermostable DNA polymerase), a polymerase chain reaction buffer, a reverse transcription buffer, and deoxynucleoside triphosphates (dNTPs).

Alternatively (or in addition), a kit can include reagents for performing a hybridization assay for nucleic acid(s) and/or proteins. The detecting agents can include nucleotide analogs and/or a labeling moiety, e.g., directly detectable moiety such as a fluorophore (fluorochrome) or a radioactive isotope, or indirectly detectable moiety, such as a member of a binding pair, such as biotin, or an enzyme capable of catalyzing a non-soluble colorimetric or luminometric reaction. In addition, the kit may further include at least one container containing reagents for detection of electrophoresed nucleic acids. Such reagents include those which directly detect nucleic acids, such as fluorescent intercalating agent or silver staining reagents, or those reagents directed at detecting labeled nucleic acids, such as, but not limited to, ECL reagents. A kit can further include DNA or RNA isolation or purification means as well as positive and negative controls. Alternatively, the kit may include at least one container containing reagents for detection of electrophoresed proteins. Such reagents include those which directly detect proteins, such as Coomassie blue or other staining reagents including fluorescent staining agents, or those reagents directed at detecting labeled proteins. A kit can further include protein isolation or purification means as well as positive and negative controls. A kit can also include a notice associated therewith in a form prescribed by a governmental agency regulating the manufacture, use or sale of diagnostic kits. Detailed instructions for use, storage and trouble-shooting may also be provided with the kit. A kit can also be optionally provided in a suitable housing that is preferably useful for robotic handling in a high throughput setting.

The components of the kit may be provided as dried powder(s). When reagents and/or components are provided as a dry powder, the powder can be reconstituted by the addition of a suitable solvent. It is envisioned that the solvent may also be provided in another container. The container will generally include at least one vial, test tube, flask, bottle, syringe, and/or other container means, into which the solvent is placed, optionally aliquoted. The kits may also comprise a second container means for containing a sterile, pharmaceutically acceptable buffer and/or other solvent.

Where there is more than one component in the kit, the kit also will generally contain a second, third, or other additional container into which the additional components may be separately placed. However, various combinations of components may be comprised in a container.

Such kits may also include components that preserve or maintain DNA or RNA, such as reagents that protect against nucleic acid degradation. Such components may be nuclease or RNase-free or protect against RNases, for example. Such kits may also include components that preserve or maintain proteins, such as reagents that protect against protein degradation. Any of the compositions or reagents described herein may be components in a kit.

In some embodiments, the kit further comprises an apparatus for collecting a blood sample from a subject. In other embodiments, the kit further comprises instructions for using the collection apparatus and/or the reagents comprising the kit.

Computer-Implemented Aspects

As understood by those of ordinary skill in the art, the methods and information described herein may be implemented, in all or in part, as computer executable instructions on known computer readable media. For example, the methods described herein may be implemented in hardware. Alternatively, the method may be implemented in software stored in, for example, one or more memories or other computer readable medium and implemented on one or more processors. As is known, the processors may be associated with one or more Controllers, calculation units and/or other units of a computer system, or implanted in firmware as desired. If implemented in software, the routines may be stored in any computer readable memory such as in RAM, ROM, flash memory, a magnetic disk, a laser disk, or other storage medium, as is also known. Likewise, this software may be delivered to a computing device via any known delivery method including, for example, over a communication channel such as a telephone line, the Internet, a wireless connection, etc., or via a transportable medium, such as a computer readable disk, flash drive, and the like.

More generally, and as understood by those of ordinary skill in the art, the various steps described above may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any known computer readable medium such as on a magnetic disk, an optical disk, or other storage medium, in a RAM or ROM or flash memory of a computer, processor, hard disk drive, optical disk drive, tape drive, etc. Likewise, the software may be delivered to a user or a computing system via any known delivery method including, for example, on a computer readable disk or other transportable computer storage mechanism.

Thus, another aspect of the disclosure is a system that is capable of carrying out a part or all of a method of the disclosure, or carrying out a variation of a method of the disclosure as described herein in greater detail. Exemplary systems include, as one or more components, computing systems, environments, and/or configurations that may be suitable for use with the methods and include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like. In some variations, a system of the disclosure includes one or more machines used for analysis of biological material (e.g., genetic material), as described herein. In some variations, this analysis of the biological material involves a chemical analysis and/or a nucleic acid amplification.

The computer may operate in a networked environment using logical connections to one or more remote computers, such as a remote computer via a network interface controller (NIC). The remote computer may be a personal computer, a server, a router, a network PC, a peer device or other common network node, and typically includes many or all of the elements described above relative to the computer. The logical connection between the NIC and the remote computer may include a local area network (LAN), a wide area network (WAN), or both, but may also include other networks. Such networking environments are commonplace in offices, enterprise-wide computer networks, intranets, and the Internet. The remote computer may also represent a web server supporting interactive sessions with the computer; or in the specific case of location-based applications may be a location server or an application server.

In some embodiments, the network interface may use a modem when a broadband connection is not available or is not used. It will be appreciated that the network connection shown is exemplary and other means of establishing a communications link between the computers may be used.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

Development of Model

Methods
Study Design and Oversight

Patients from 11 centers (Table 1) in the Mount Sinai Acute GVHD International Consortium (MAGIC) underwent first allogeneic HCT from January 2005 to June 2015 and provided blood samples for a biorepository 7±3 days after HCT (FIG. 1). The institutional review boards at each of the 11 participating centers approved this study. Patient samples from the two largest contributing centers, the University of Michigan, Ann Arbor, Mich., USA (n=642) and the University of Regensburg, Germany (n=287) were combined and were then randomly assigned to a training (n=620) and test (n=309) set, conditional to similar ratios of patients from each center, median HCT dates, and overall 6-month non-relapse mortality. An independent group of 358 patients from the nine other MAGIC centers constituted the validation set (Table 2).

TABLE 1

Patient Characteristics (n = 1287).

| Characteristic | Training set (N = 620) | Test set (N = 309) | Validation set (N = 358) |
|---|---|---|---|
| Median age - yr (range) | 52 (0-71) | 52 (0-73) | 54 (1-77) |
| Indication for HCT - no. (%) | | | |
| Acute leukemia | 331 (53.4) | 162 (52.4) | 189 (52.8) |
| MDS/MPN | 96 (15.5) | 44 (14.2) | 89 (24.9) |
| Lymphoma | 88 (14.2) | 40 (12.9) | 21 (5.9) |
| Other Malignant | 81 (13.1) | 47 (15.2) | 39 (10.9) |
| Non-Malignant | 24 (3.9) | 16 (5.2) | 20 (5.6) |
| Disease Status at HCT[a] - no. (%) | | | |
| Other/Low/Intermediate | 385 (62.1) | 194 (62.8) | 253 (70.7) |
| High | 182 (29.4) | 90 (29.1) | 101 (28.2) |
| Unknown | 53 (8.5) | 25 (8.1) | 4 (1.1) |
| Donor type - no. (%) | | | |
| Related | 246 (39.7) | 129 (41.7) | 142 (39.7) |
| Unrelated | 374 (60.3) | 180 (58.3) | 216 (60.3) |
| HLA-match - no. (%) | | | |
| Matched[b] | 513 (82.7) | 256 (82.8) | 290 (81.0) |
| Mismatched | 107 (17.3) | 53 (17.2) | 68 (19.0) |

TABLE 1-continued

Patient Characteristics (n = 1287).

| Characteristic | Training set (N = 620) | Test set (N = 309) | Validation set (N = 358) |
|---|---|---|---|
| Stem cell source - no. (%) | | | |
| Marrow | 79 (12.7) | 36 (11.7) | 62 (17.3) |
| Peripheral blood | 510 (82.3) | 257 (83.2) | 273 (76.3) |
| Cord blood | 31 (5.0) | 16 (5.2) | 23 (6.4) |
| Conditioning Regimen Intensity - no. (%) | | | |
| Full | 356 (57.4) | 173 (56.0) | 210 (58.7) |
| Reduced | 264 (42.6) | 136 (44.0) | 148 (41.3) |
| GVHD prophylaxis - no. (%) | | | |
| CNI/MTX ± other | 415 (66.9) | 211 (68.3) | 216 (60.3) |
| CNI/MMF ± other | 193 (31.1) | 85 (27.5) | 132 (36.9) |
| CNI/sirolimus | 7 (1.1) | 5 (1.6) | 1 (0.3) |
| Other | 5 (0.8) | 8 (2.6) | 9 (2.5) |
| GVHD serotherapy prophylaxis - no. (%) | | | |
| ATG | 167 (26.9) | 77 (24.9) | 131 (36.6) |
| No ATG | 453 (73.1) | 232 (75.1) | 227 (63.4) |

*There were no significant differences between the training set and test set. Significant differences between the training set and validation set included indication for HCT (p < 0.001), disease status at HCT (p < 0.001), GVHD prophylaxis (p = 0.015), and the inclusion of serotherapy in GVHD prophylaxis (p = 0.002). Significant differences between the test set and validation set included indication for HCT (p < 0.001), disease status at HCT (p < 0.001), GVHD prophylaxis (p = 0.024), and GVHD prophylaxis that included serotherapy (p = 0.001).
[a]Disease status according to 2014 ASBMT RFI classifications;
[b]Donor-patient pairs were considered matched if all 8 HLA-A, -B, -C and -DRB1 alleles matched for related and unrelated marrow or peripheral blood transplants and if 5 or 6/6 HLA-A, -B and -DRB1 alleles matched for cord blood transplants.
Table 1 Abbreviations:
MDS/MPD, myelodysplastic syndrome/myeloproliferative neoplasms;
CNI, calcineurin inhibitor;
MTX, methotrexate;
MMF, mycophenolic acid;
ATG, anti-thymocyte globulin.

TABLE 2

MAGIC Centers Represented in the Multicenter Validation Set.

| SET | CENTER | SAMPLES |
|---|---|---|
| Training (N = 620) | University of Michigan | 428 |
| | University of Regensburg | 192 |
| Test (N = 309) | University of Michigan | 214 |
| | University of Regensburg | 95 |
| Validation (N = 358) | Mayo Clinic | 100 |
| | University of Hamburg | 90 |
| | Ohio State University | 47 |
| | University of Pennsylvania | 29 |
| | King Chulalongkorn Memorial Hospital - Bangkok | 27 |
| | Emory University | 21 |
| | Icahn School of Medicine at Mount Sinai | 18 |
| | University of Wurzburg | 14 |
| | University Hospital Carl Gustav Carus Dresden | 12 |

Clinical Data, Blood Collection and Analysis

GVHD clinical staging was standardized using published guidelines,[13] and was prospectively reviewed during monthly data teleconferences starting in 2013 (n=600). Blood samples were collected prospectively 7±3 days post-HCT. Non-relapse deaths were considered related to GVHD if the patient died from either GVHD itself or from an infection that developed while receiving systemic steroids for the treatment of GVHD. Samples were shipped to a central laboratory where they were analyzed in batches for four GVHD biomarkers (ST2, REG3α, TNFR1, and IL-2Rα) by enzyme-linked immunosorbent assays as previously described.[14-16]

Statistical Analyses

Biomarker concentrations were normalized by log-transformation and all 13 possible combinations of 1 to 4 biomarkers were used to model 6-month NRM by competing risks regression, with relapse as the competing risk.[17] Models were compared using either Akaike's Information Criterion for non-nested comparisons or the Wald test for nested comparisons to determine the most accurate model.[18] The combination of ST2 and REG3α best predicted 6-month NRM, which was confirmed with Monte Carlo cross validation by randomly creating 75 different training sets and repeating the modeling process.[19] The combination of these two biomarkers is highly effective in determining risk of developing NRM and severe GVHD, with use of each biomarker individually or in combination with at least one other biomarker being less effective. 75/75 (100%) of the two biomarker models included ST2 and 68/75 (91%) included REG3α. A training set was then created at random and the entire process was repeated to generate a final model: $\log[-\log(1-\hat{p})]=-11.263+1.844(\log ST2)+0.577(\log REG3\alpha)$, where $\hat{p}$=predicted probability of 6-month NRM. The $\hat{p}$ was determined for each patient and rank ordered from lowest to highest. Multiple thresholds were observed that demarcated groups with a difference of at least 15% NRM, which was deemed clinically significant (Table 3). A threshold of $\hat{p}$=0.16 was chosen to maximize the size of the high risk (HR) patient group while maintaining a near maximum difference in NRM. Differences in cumulative incidence of NRM and relapse between high and low risk groups were calculated by Gray's test. Overall survival was estimated by the Kaplan-Meier method and differences between groups were calculated using the log-rank test.

TABLE 3

Representative Thresholds That Define Risk Groups. Table 3A, Training Set; Table 3B, Test Set; Table 3C, Validation Set.

Table 3A Training Set.

A. Training Set (N = 620)

| Thresholds | MAGIC Risk Group | Proportion | 6-month NRM | ΔNRM | p-value |
|---|---|---|---|---|---|
| 0.14 | High | 21% | 24% | 17% | <0.001 |
|  | Low | 79% | 7% |  |  |
| 0.15 | High | 19% | 26% | 19% | <0.001 |
|  | Low | 81% | 7% |  |  |
| 0.16 | High | 16% | 28% | 21% | <0.001 |
|  | Low | 84% | 7% |  |  |
| 0.17 | High | 15% | 29% | 22% | <0.001 |
|  | Low | 85% | 7% |  |  |
| 0.18 | High | 14% | 28% | 20% | <0.001 |
|  | Low | 86% | 8% |  |  |

Table 3B Test Set.

B. Test Set (N = 309)

| Thresholds | MAGIC Risk Group | Proportion | 6-month NRM | ΔNRM | p-value |
|---|---|---|---|---|---|
| 0.14 | High | 22% | 27% | 19% | <0.001 |
|  | Low | 78% | 8% |  |  |
| 0.15 | High | 19% | 30% | 22% | <0.001 |
|  | Low | 81% | 8% |  |  |
| 0.16 | High | 17% | 33% | 26% | <0.001 |
|  | Low | 83% | 7% |  |  |
| 0.17 | High | 15% | 33% | 25% | <0.001 |
|  | Low | 85% | 8% |  |  |
| 0.18 | High | 14% | 33% | 24% | <0.001 |
|  | Low | 86% | 9% |  |  |

Table 3C Validation Set.

C. Validation Set (N = 358)

| Thresholds | MAGIC Risk Group | Proportion | 6-month NRM | ΔNRM | p-value |
|---|---|---|---|---|---|
| 0.14 | High | 25% | 24% | 14% | <0.001 |
|  | Low | 75% | 10% |  |  |
| 0.15 | High | 24% | 26% | 16% | <0.001 |
|  | Low | 76% | 10% |  |  |
| 0.16 | High | 20% | 26% | 16% | <0.001 |
|  | Low | 80% | 10% |  |  |
| 0.17 | High | 19% | 25% | 14% | <0.001 |
|  | Low | 81% | 11% |  |  |
| 0.18 | High | 16% | 27% | 16% | <0.001 |
|  | Low | 84% | 11% |  |  |

Patient characteristics between training, test and validation sets were compared using chi-squared or Wilcoxon Rank Sum tests as appropriate. Differences in proportions for the cause of death analysis and GVHD incidence were calculated using chi-squared tests. Clinical risk factors that were statistically significant ($p<0.05$) predictors for NRM were identified by univariate analysis in the training set (Table 4). An algorithm to predict NRM that combined significant clinical risk factors and biomarkers was derived using the same training set used to derive the biomarkers-only algorithm. All analyses were performed using R statistical package version 3.2.3 (R Development Core Team 2015).

TABLE 4

Univariate Analysis of Clinical Risk Factors for NRM.

| | Training Set (n = 620) | |
|---|---|---|
| Variable | Hazard Ratio (95% CI) | p-value |
| Donor: unrelated vs. related | 3.07 (1.65-5.73) | <0.001 |
| HLA match: matched vs. mismatched | 1.89 (1.10-3.25) | 0.02 |
| Conditioning: reduced vs. full | 0.78 (0.47-1.29) | 0.34 |
| Age† | 1.12 (0.93-1.35) | 0.24 |

†Reflects 10-year increases in age.

Results

Patients

The clinical characteristics of all the patients are shown in Table 1. No significant differences between training and test sets were observed following randomization. An independent multicenter validation set (nine centers, three countries; n=358) differed significantly from the training and test sets with myelodysplastic syndrome as a more frequent indication for HCT (25% vs. 14%, p<0.001), fewer patients with unknown disease status at HCT (1% vs. 8%, p<0.001), less use of methotrexate containing GVHD prophylaxis (60% vs. 68%, p=0.024) and more use of anti-thymocyte globulin (37% vs. 25%, p=0.001). The overall incidence of 6-month NRM for the training, test, and validation sets were highly similar at 11%, 12%, and 13%, respectively. The median day of GVHD onset was 28 days in the training sets and 29 days in the test and validation sets (Table 5).

TABLE 5

Patient Outcomes by Set.

| Characteristic | Training set (N = 620) | Test set (N = 309) | Validation set (N = 358) |
|---|---|---|---|
| Overall 6-month NRM - no. (%) | 68 (11.0) | 37 (12.0) | 47 (13.1) |
| GVHD grade at maximum - no. (%) | | | |
| No GVHD | 274 (44.2) | 133 (43.0) | 180 (50.3) |
| I | 113 (182) | 40 (12.9) | 55 (15.4) |
| II | 138 (22.3) | 81 (26.2) | 70 (19.6) |
| III | 50 (8.1) | 32 (104) | 35 (9.8) |
| IV | 45 (7.3) | 23 (7.4) | 18 (5.0) |
| GVHD onset - median day (range) | 28 (7-175) | 29 (8-168) | 29 (10-177) |
| GVHD onset ≥14 days post HCT - no. (%) | 311 (90) | 158 (90) | 166 (93) |

Algorithm Development

Figure 5:
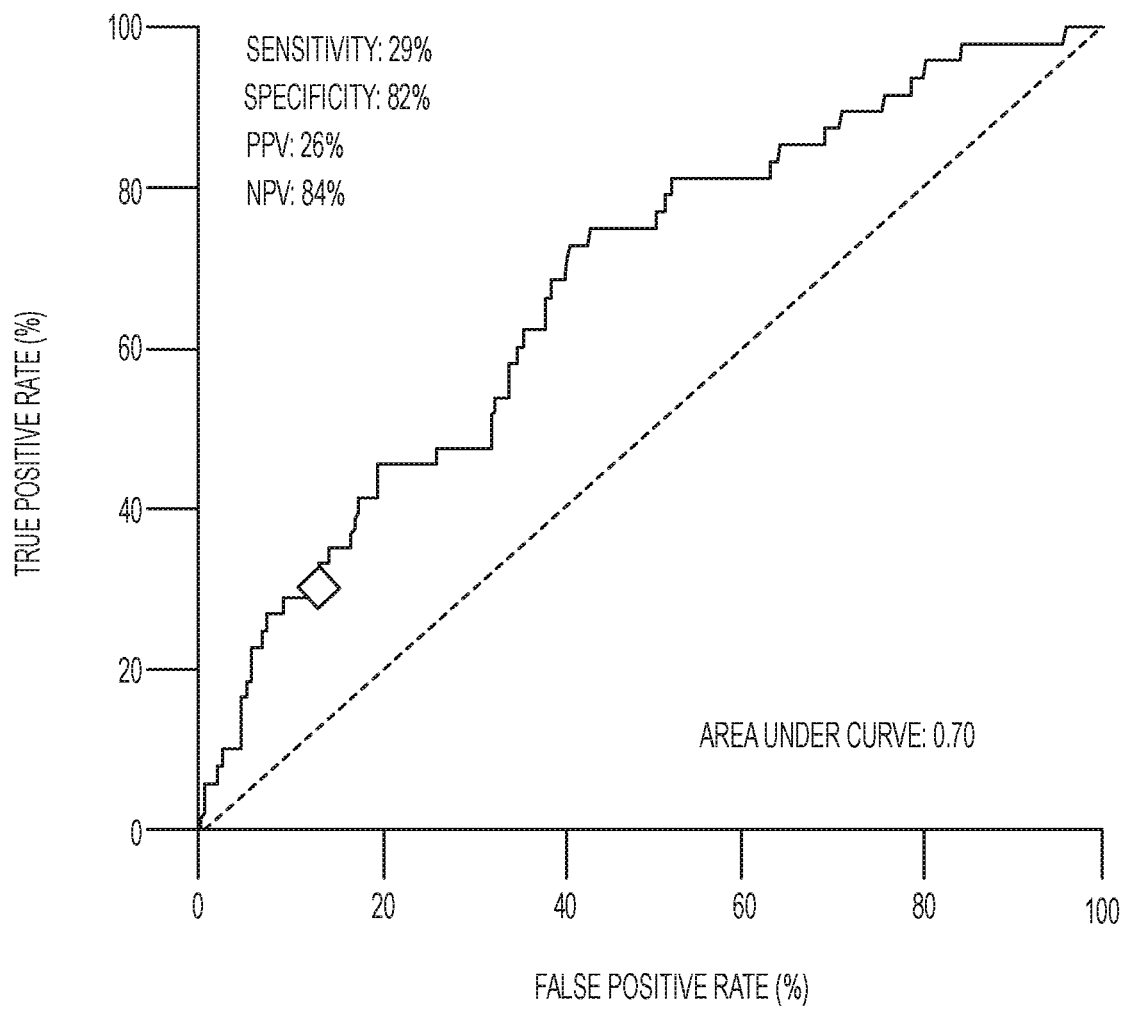
FIG. 5. Receiver Operator Characteristic Curve for Final Algorithm Applied to the Multicenter Validation Set. Receiver operating characteristic curve for the day +7 MAGIC algorithm for prediction of 6-month non-relapse mortality. The diamond indicates the threshold that defines low versus HR groups.

The inventors developed a predictive model using biomarker combinations in samples from the training set through a rigorous strategy to maximize reproducibility (see herein). One of the most accurate models included the concentrations of ST2 and REG3α and the area under the receiver operating characteristic curve is 0.70 (FIG. 5). A threshold of $\hat{p}=0.16$ separated high risk (HR) and low risk (LR) groups with a maximum number of HR patients with a near maximum difference in NRM.

Algorithm Performance

This final MAGIC algorithm identified a HR group in the training set whose NRM (28%) was significantly greater (p<0.001) than that of the LR group (7%) (FIG. 2A). Application of this algorithm to the test set produced similar, highly statistically significant differences between HR and LR groups (FIG. 2B). A second validation was performed in the multicenter set and again large differences were observed between groups, with a HR 6-month NRM of 26% versus the 10% in the LR group (p<0.001) (FIG. 2C). The proportion of patients in the HR group was similar in all three patient sets (16%-20%). Relapse rates were equivalent in both risk groups in all three sets (FIG. 2D-2F) with the result that HR patients experienced significantly worse overall survival (p<0.001) (FIG. 2G-2I).

Figure 6:
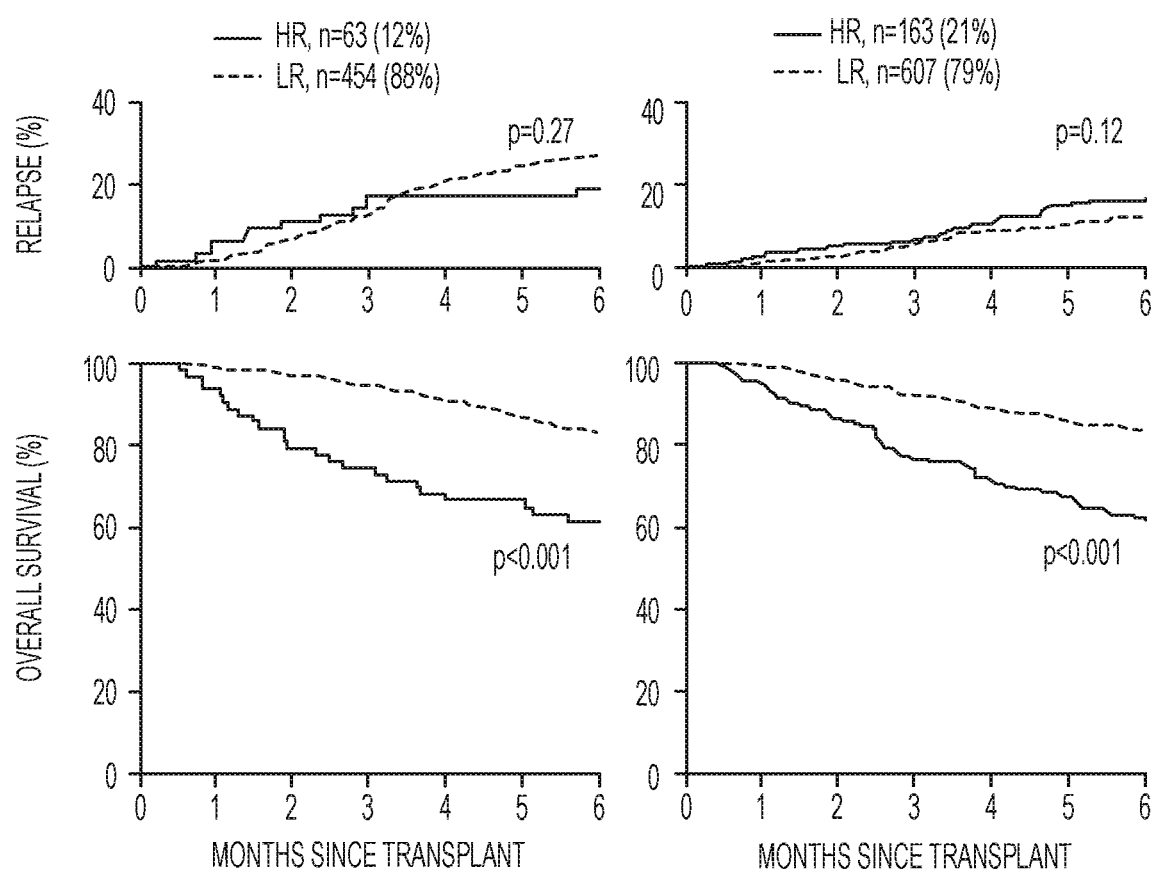
FIG. 6. Relapse and Overall Survival by Donor Type. 6-month relapse rates for all patients (n=1287) were as follows: Related donor: HR 19%; LR 27%; Unrelated donor: HR 17%; LR 23%. 6-month overall survival rates were as follows: Related donor: HR 62%; LR 83%; Unrelated donor: HR 62%; LR 84%.
Figure 7:
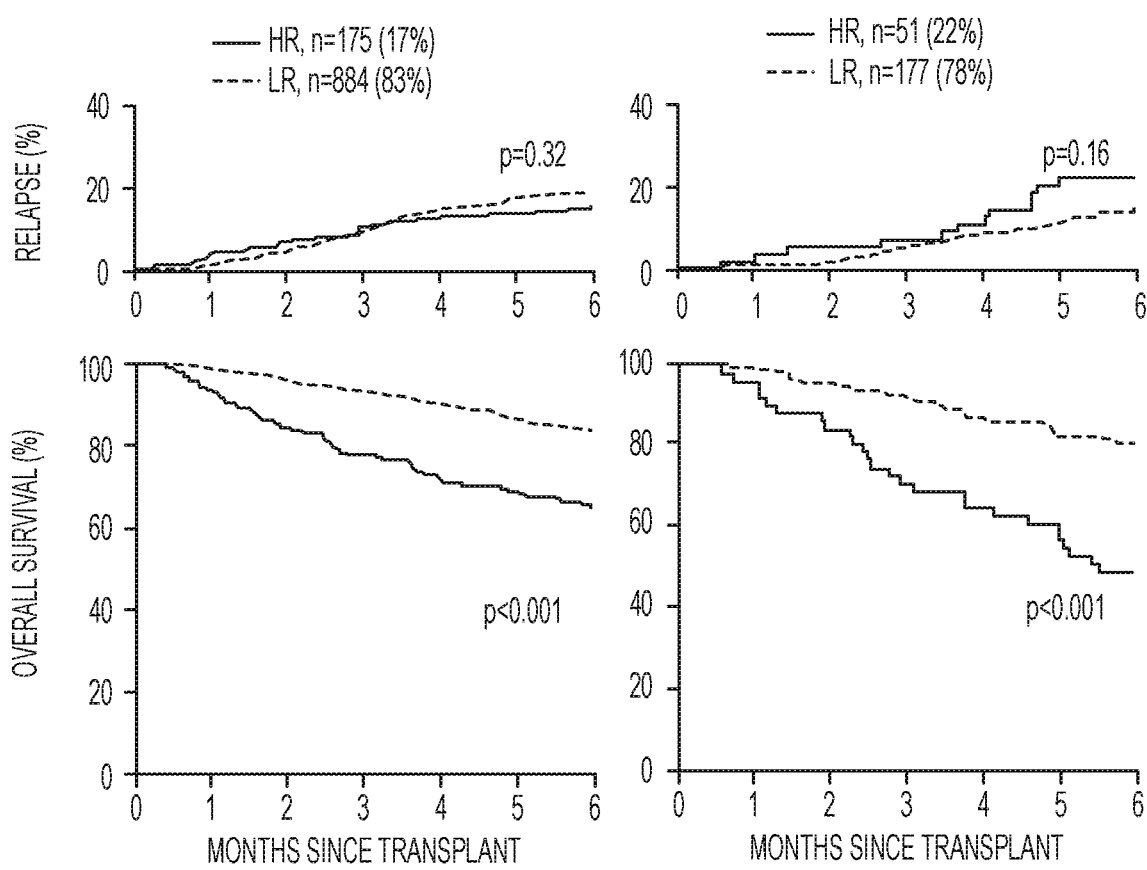
FIG. 7. Relapse and Overall Survival by HLA Histocompatibility. 6-month relapse rates for all patients (n=1287) were as follows: HLA-matched: HR 16%; LR 19%; HLA-mismatched: HR 24%; LR 15%. 6-month overall survival rates were as follows: HLA-matched: HR 65%; LR 84%; HLA-mismatched: HR 49%; LR 81%.
Figure 8:
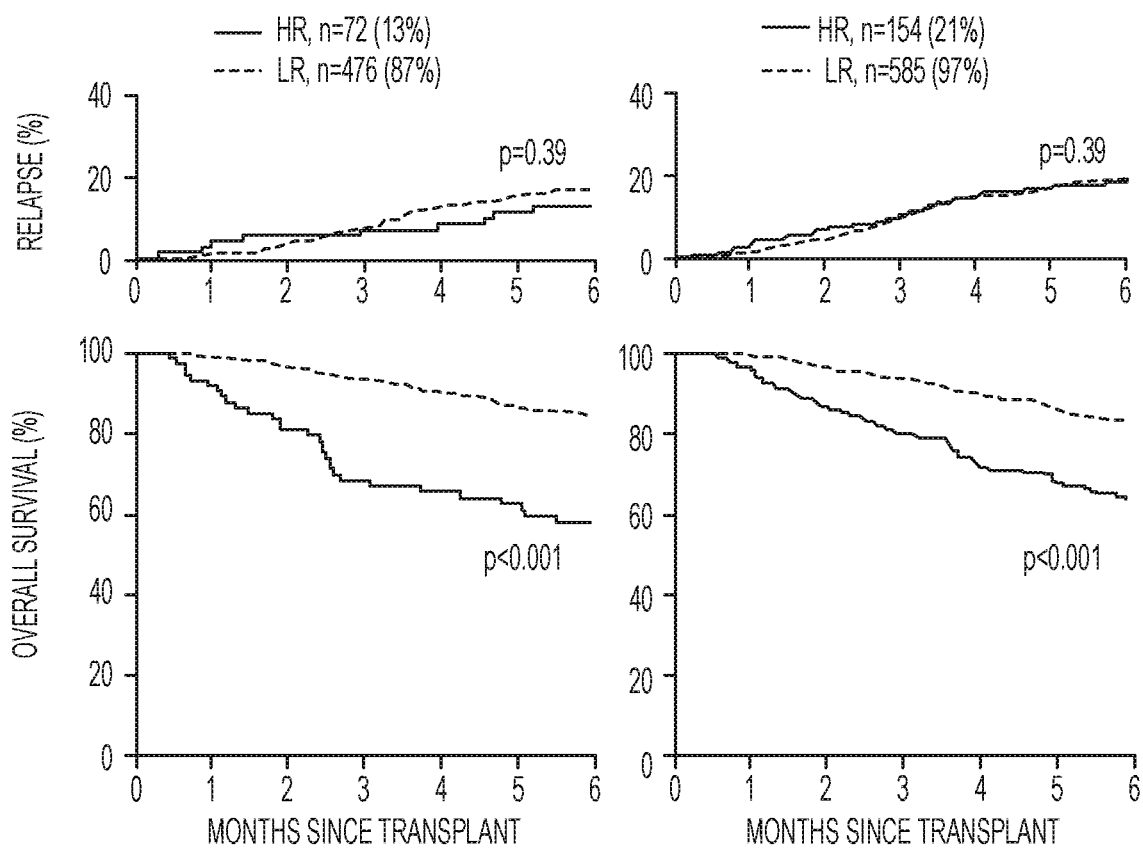
FIG. 8. Relapse and Overall Survival by Conditioning Regimen Intensity. 6-month relapse rates for all patients (n=1287) were as follows: Reduced-intensity conditioning: HR 13%; LR 17%; Full-intensity conditioning: HR 20%; LR 20%. 6-month overall survival rates were as follows: Reduced-intensity conditioning: HR 58%; LR 84%; Full-intensity conditioning: HR 64%; LR 83%.

Several pre-HCT clinical risk factors predict a higher risk of NRM, such as HLA-mismatch, non-family member donors, age of the recipient, and the intensity of the conditioning regimen.[6,20] Donor type and match were significant predictors of NRM in univariate analyses performed on the training set (Table 5). Yet the MAGIC algorithm still stratified patients into two distinct risk groups independently of the degree of HLA match between donor and recipient, the genetic relationship of the donor to the recipient, the intensity of the conditioning regimen and age (FIGS. 3A-3D). The differences between groups remained statistically significant in all three sets within each clinical risk factor except for pediatric patients in sets where the total number of patients was exceptionally small (Table 6). Again, relapse rates were equivalent within all subgroups of clinical risk factors, resulting in a decrease of at least 20% in overall survival for HR patients (FIGS. 6, 7, 8).

TABLE 6

Non-Relapse Mortality for Risk Groups Stratified by Individual Sets.
Table 6A. Training Set, Table 6B. Test Set, Table 6C. Validation Set.

Table 6A Training Set.

| MAGIC Risk Group | | Sample Size | 6-Month NRM (%) | 95% CI (%) | p-value |
|---|---|---|---|---|---|
| Training Set (N = 620) | | | | | |
| Donor Type | | | | | |
| Related | Low | 217 | 3 | 1-6 | p = 0.001 |
| | High | 29 | 18 | 6-34 | |
| Unrelated | Low | 303 | 10 | 7-14 | p < 0.001 |
| | High | 71 | 33 | 22-44 | |
| HLA | | | | | |
| Matched | Low | 431 | 6 | 4-9 | p < 0.001 |
| | High | 82 | 26 | 17-36 | |
| Mismatched | Low | 89 | 12 | 7-20 | p = 0.005 |
| | High | 18 | 39 | 16-61 | |
| Conditioning Intensity | | | | | |
| Reduced | Low | 234 | 6 | 3-10 | p < 0.001 |
| | High | 30 | 35 | 18-53 | |
| Full | Low | 286 | 8 | 5-12 | p < 0.001 |
| | High | 70 | 26 | 16-36 | |
| Age | | | | | |
| ≤21 | Low | 62 | 5 | 1-12 | p < 0.001 |
| | High | 7 | 57 | 13-86 | |
| >21 | Low | 458 | 7 | 5-10 | p < 0.001 |
| | High | 93 | 26 | 18-36 | |

TABLE 6-continued

Non-Relapse Mortality for Risk Groups Stratified by Individual Sets.
Table 6A. Training Set, Table 6B. Test Set, Table 6C. Validation Set.

Table 6B Test Set.

| MAGIC Risk Group | | Sample Size | 6-Month NRM (%) | 95% CI (%) | p-value |
|---|---|---|---|---|---|
| Test Set (N = 309) | | | | | |
| Donor Type | | | | | |
| Related | Low | 112 | 4 | 1-8 | p < 0.001 |
| | High | 17 | 35 | 14-58 | |
| Unrelated | Low | 143 | 11 | 6-16 | p = 0.001 |
| | High | 37 | 32 | 18-48 | |
| HLA | | | | | |
| Matched | Low | 219 | 6 | 4-10 | p < 0.001 |
| | High | 37 | 30 | 16-45 | |
| Mismatched | Low | 36 | 14 | 5-27 | p = 0.036 |
| | High | 17 | 41 | 18-64 | |
| Conditioning Intensity | | | | | |
| Reduced | Low | 120 | 11 | 6-17 | p = 0.001 |
| | High | 16 | 44 | 19-67 | |
| Full | Low | 135 | 4 | 2-9 | p < 0.001 |
| | High | 38 | 29 | 15-44 | |
| Age | | | | | |
| ≤21 | Low | 23 | 9 | 1-25 | p = 0.470 |
| | High | 12 | 17 | 2-43 | |
| >21 | Low | 232 | 7 | 4-11 | p < 0.001 |
| | High | 42 | 38 | 23-53 | |

Table 6C Validation Set.

| MAGIC Risk Group | | Sample Size | 6-Month NRM (%) | 95% CI (%) | p-value |
|---|---|---|---|---|---|
| Validation Set (N = 358) | | | | | |
| Donor Type | | | | | |
| Related | Low | 125 | 10 | 5-16 | p = 0.013 |
| | High | 17 | 29 | 10-52 | |
| Unrelated | Low | 161 | 11 | 6-16 | p = 0.006 |
| | High | 55 | 26 | 15-38 | |
| HLA | | | | | |
| Matched | Low | 234 | 9 | 6-14 | p = 0.004 |
| | High | 56 | 23 | 13-35 | |
| Mismatched | Low | 52 | 13 | 6-24 | p = 0.026 |
| | High | 16 | 38 | 15-61 | |
| Conditioning Intensity | | | | | |
| Reduced | Low | 122 | 11 | 6-17 | p = 0.001 |
| | High | 26 | 35 | 17-53 | |
| Full | Low | 164 | 10 | 6-15 | p = 0.028 |
| | High | 46 | 22 | 11-35 | |
| Age | | | | | |
| ≤21 | Low | 33 | 6 | 1-18 | NA |
| | High | 3 | NA | NA | |
| >21 | Low | 253 | 11 | 7-15 | p < 0.001 |
| | High | 69 | 28 | 18-38 | |

TABLE 7

Causes of Non-Relapse Mortality by Risk Group (N = 1287).

| Cause - no. (%) | Low Risk (N = 1061) | High Risk (N = 226) |
|---|---|---|
| Acute GVHD | 47 (4.43) | 41 (18.14) |
| Chronic GVHD | 3 (0.28) | 2 (0.88) |
| Infection unrelated to GVHD | 15 (1.41) | 7 (3.10) |
| Graft failure | 2 (0.19) | 2 (0.88) |
| Pulmonary events* | 10 (0.94) | 3 (1.33) |
| Cardiac events | 2 (0.19) | 2 (0.88) |
| Neurologic events | 1 (0.09) | 3 (1.33) |
| New malignancy** | 3 (0.28) | 0 |
| VOD/SOS | 0 | 2 (0.88) |
| Other | 0 | 2 (0.88) |
| Total | 83 (7.82) | 64 (28.32) |

*Includes diffuse alveolar hemorrhage, idiopathic pneumonia syndrome, and respiratory failure not otherwise specified.
**Includes 2 post-transplant lymphoproliferative disorder, 1 metastatic gastric adenocarcinoma.

Causes of Non-Relapse Mortality

Figure 4A:
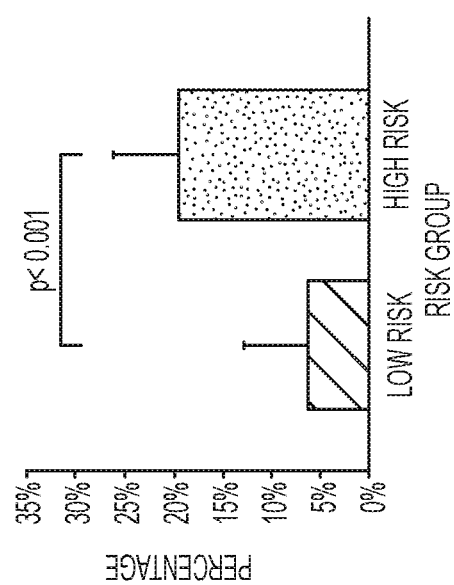
FIG. 4A-4C. GVHD-Related Mortality by MAGIC Risk Stratification. GVHD-related mortality was assessed for HR and LR patients in each patient set.
Figure 4B:
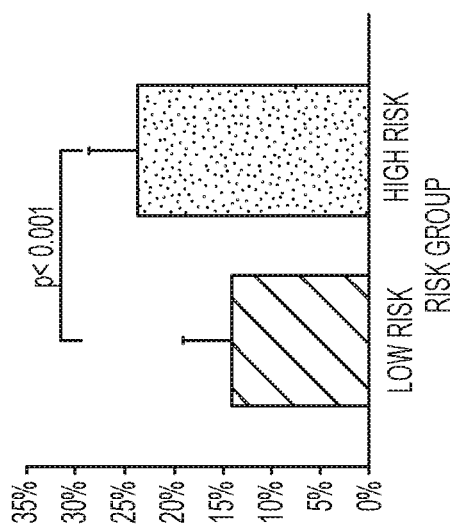
Figure 4C:
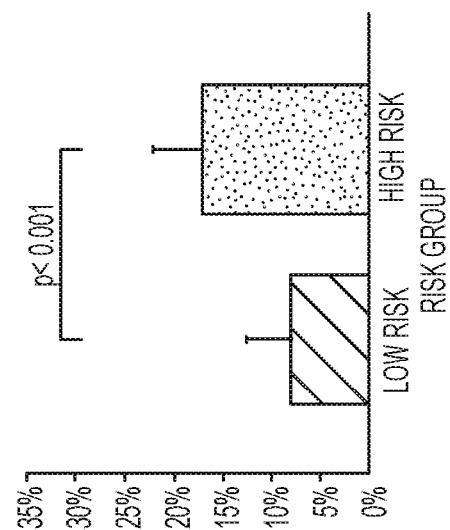

The inventors next analyzed the contribution of GVHD to NRM. HR patients were four times more likely to die from GVHD than LR patients when all 1287 patients were considered (HR, 18% vs LR, 4%, p<0.001) and the difference was statistically significant within each set (FIG. 4). GVHD related deaths reflect the efficacy of treatments that varied according to the standard of care at each center, but the majority of patients with grade II-IV acute GVHD received high dose systemic steroids. Because the GI tract is the GVHD target organ that is most resistant to treatment and represents a major cause of NRM,[11,21] the inventors evaluated severe (stage 3 and 4) GI GVHD in all patient sets and observed nearly twice as much severe GI GVHD in HR patients as in LR patients (17% vs 8%, p<0.001). All causes of non-relapse mortality are shown in Table 8.

TABLE 8

Comparison of Algorithms with and without Clinical Risk Factors*.
Table 8A. Training Set, Table 8B. Test Set, Table 8C. Validation Set.

Table 8A Training Set.

| MAGIC | | A. Training set (N = 620) | | | |
|---|---|---|---|---|---|
| | Risk Group | Proportion | 6-month NRM | ΔNRM | p-value |
| Biomarkers without clinical risk factors | High | 16% | 28% | 21% | <0.001 |
| | Low | 84% | 7% | | |
| Biomarkers with clinical risk factors | High | 19% | 30% | 24% | <0.001 |
| | Low | 81% | 6% | | |

Table 8B Test Set.

| MAGIC | | B. Test set (N = 309) | | | |
|---|---|---|---|---|---|
| | Risk Group | Proportion | 6-month NRM | ΔNRM | p-value |
| Biomarkers without clinical risk factors | High | 17% | 33% | 26% | <0.001 |
| | Low | 83% | 7% | | |
| Biomarkers with clinical risk factors | High | 16% | 26% | 21% | <0.001 |
| | Low | 82% | 7% | | |

TABLE 8-continued

Comparison of Algorithms with and without Clinical Risk Factors*.
Table 8A. Training Set, Table 8B. Test Set, Table 8C. Validation Set.

Table 8C Validation Set.

| MAGIC | | C. Validation set (N = 358) | | | |
|---|---|---|---|---|---|
| | Risk Group | Proportion | 6-month NRM | ΔNRM | p-value |
| Biomarkers without clinical risk factors | High | 20% | 26% | 16% | <0.001 |
| | Low | 80% | 10% | | |
| Biomarkers with clinical risk factors | High | 24% | 24% | 14% | <0.001 |
| | Low | 76% | 10% | | |

*Clinical risk factors included based on univariate analyses (Table 4) were donor type and HLA-match.

Discussion

A long sought goal in hematopoietic cell transplantation is the identification of individual patients at high risk (HR) for severe GVHD. The day +7±3 (post-HCT) MAGIC algorithm developed here identifies a significant number of such patients. The algorithm's reproducibility among multiple transplant centers may be attributed to several elements of the study design. First, the acquisition rate of samples was very high (93%), ensuring a broad representation of patients. Second, the clinical data practices were standardized and monitored among all centers, thereby increasing the accuracy of the data. Third, the final algorithm was the result of a vigorous cross-validation strategy in a large number of patients that tested performance in 75 different combinations of the training set prior to the development of the final model and its validation in two independent sets.

Importantly, the fidelity of risk assignment by the MAGIC algorithm transcends known clinical risk factors for GVHD, such as conditioning regimen, age, HLA mismatch, or relatedness of the donor. These latter two risk factors directly reflect the histocompatibility antigens in the host to which donor T cells respond within days of graft infusion and were significant predictors of NRM in univariate analysis in the training set, but their incorporation into the algorithm did not appreciably improve its performance (Table 8). The GVH reaction is already in progress by approximately day +7 (post-HCT) and has led to increased biomarker concentrations, even though clinical symptoms may not occur until days or weeks later. The same may be said for the conditioning regimen intensity, which correlates with the inflammation that amplifies donor T cell responses to host alloantigens.[22] The MAGIC algorithm's fidelity across these variables derives from assigning a greater percentage of patients with an adverse characteristic to the HR group. For example, 163/770 (21%) of unrelated donors are assigned to the HR group compared to 63/517 (12%) of related donors (p<0.001). The overall incidence of severe GI GVHD in this study (9.6%) was similar to that of other reports (7.9%),[21] and the GI tract is affected in 86% of severe cases, proving key to overall GVHD severity.[12] It is thus worth noting that the algorithm allocated twice as many patients to the HR group (17% versus 8%) who would eventually develop severe GI GVHD. It is hypothesized that the blood biomarker concentrations on day +7 reflect subclinical GI pathology, a notion that is reinforced by the fact that ST2 and REG3α, the two biomarkers that performed the best in the models, are closely associated with GI GVHD.[14,23,24]

This large study confirms earlier studies in which 50% of GVHD occurs after day 28 and 90% occurs after day 14 (Table 5).[11,12] Thus, the use of the MAGIC algorithm disclosed herein could facilitate preemptive intervention for GVHD prior to the onset of clinical disease in a substantial number of patients. One attractive strategy that avoids global immunosuppression and thus minimizes increased risk for relapse is to interrupt traffic of GVHD effector cells to the GI tract. Blockade of the α4β7 integrin expressed on donor T cells that home to the intestinal mucosa can abrogate experimental GVHD[25-27] and α4β7 is expressed on greater percentages of T cells in patients who later develop intestinal acute GVHD.[28] The safety and efficacy of monoclonal antibodies such as vedolizumab (α4β7 antagonist), natalizumab (α4 antagonist), and etrolizumab (β7 antagonist) to treat inflammatory bowel disease is established,[29-31] making them prime candidates for such intervention. Two clinical trials of such strategies in GVHD prophylaxis or treatment are currently ongoing (clinicaltrials.gov #NCT02133924 and #NCT02728895).

The biomarkers for HR disease may identify additional pathways that could be therapeutically targeted. ST2, the soluble interleukin 33 receptor (IL-33), is shed from activated T cells as GVHD progresses and soluble ST2 administration has been shown to reduce experimental GVHD.[23,24] Additional strategies may target IL-33 itself, which is released from dying GI epithelial cells during GVHD. REG3α is produced by GI epithelium, in particular Paneth cells, whose numbers decrease significantly during GVHD.[32,33] Thus REG3α production decreases during GVHD even as its concentration increases in the bloodstream as a result of damaged epithelial mucosa.[14] Interleukin 22 (IL-22) induces REG3α, and lower numbers of circulating, IL-22 secreting innate lymphoid cells after transplant are associated with a higher risk for GVHD.[34,35] Administration of IL-22 restores REG3α homeostasis and accelerates repair of the epithelial mucosa, preventing GVHD in preclinical models.[35,36] This appealing approach avoids further immunosuppression altogether and in fact enhances the reconstitution of the innate immune system of the GI tract. A recombinant version of IL-22 has been approved for human use and is currently being tested in a clinical trial to treat GVHD (clinicaltrials.gov #NCT02406651).

Regardless of the nature of preemptive interventions, the MAGIC algorithm should prove a useful tool in clinical research of GVHD therapy because it identifies patients at high risk for severe disease. The exact nature of the intervention, including its inherent risks as well as potential benefits, will largely determine the enthusiasm of patients and physicians for any particular approach. Future improvements to the algorithm might include the incorporation of additional biomarkers or repeating the test at a later time point to increase sensitivity. Nevertheless, the MAGIC algorithm described herein represents an important advance toward precision medicine for HCT patients.

Example 2

Multiple Timepoints Improve Accuracy of Model

The inventors next determined whether repeat testing of biomarkers on day +14 post-bone marrow transplant could increase the sensitivity of the algorithm for lethal GVHD described herein.

Graft-versus-host disease (GVHD) is the leading cause of non-relapse mortality (NRM) in allogeneic bone marrow transplant (BMT) patients. The median onset of GVHD is 28 days after BMT. As demonstrated herein, the inventors have developed and validated an algorithm using two serum biomarkers (ST2 and REG3α) to stratify patients on day +7 after BMT into low risk (LR) and high risk (HR) groups for 6 month NRM. Identification of high risk patients by this blood test prior to the development of symptoms could allow for intervention with known and/or novel therapies designed to pre-empt lethal GVHD.

It was hypothesized that repeating the test one week closer to the development of GVHD (day +14) in patients initially categorized as low risk (LR) would identify substantially more HR patients as candidates for novel pre-emptive therapy.

Results and Discussion

Figure 9:
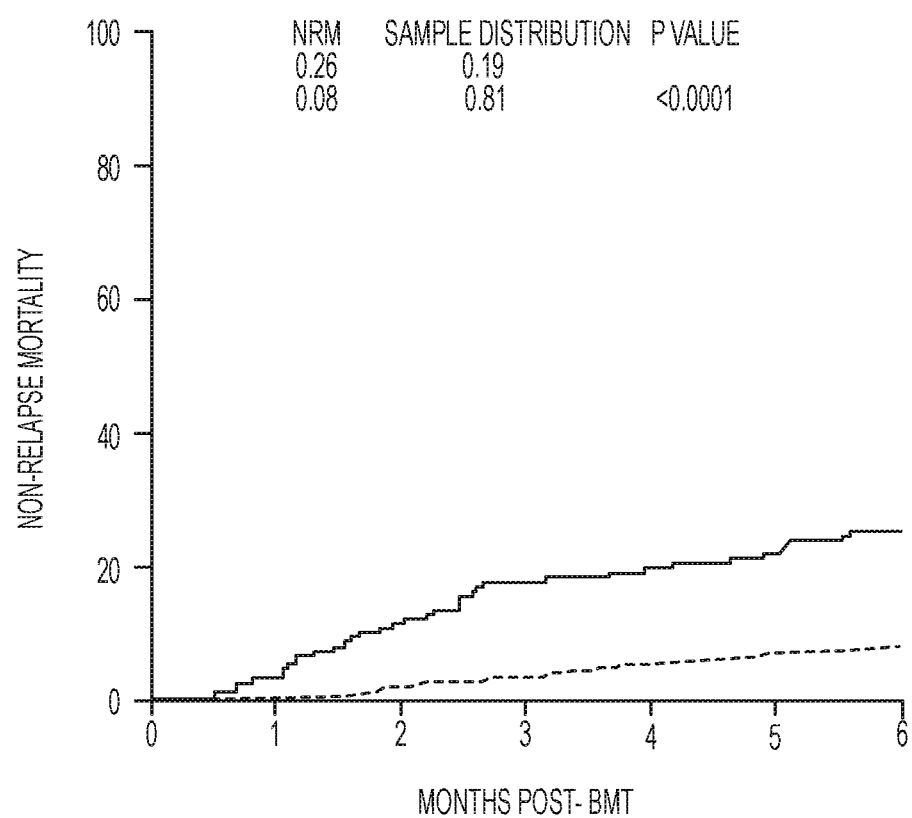
FIG. 9. Day +7 algorithm stratifies patients into high and low risk. Testing patients on day +7 after bone marrow transplant (BMT) can categorize patients into high risk of developing GVHD and low risk of developing GVHD.

The algorithm and methods described herein stratified patients for six-month NRM (HR 19%, LR 81%) on day +7 post-BMT. HR patients have higher NRM (26% for HR vs. 8% for LR, p<0.0001) (FIG. 9).

Figure 10:
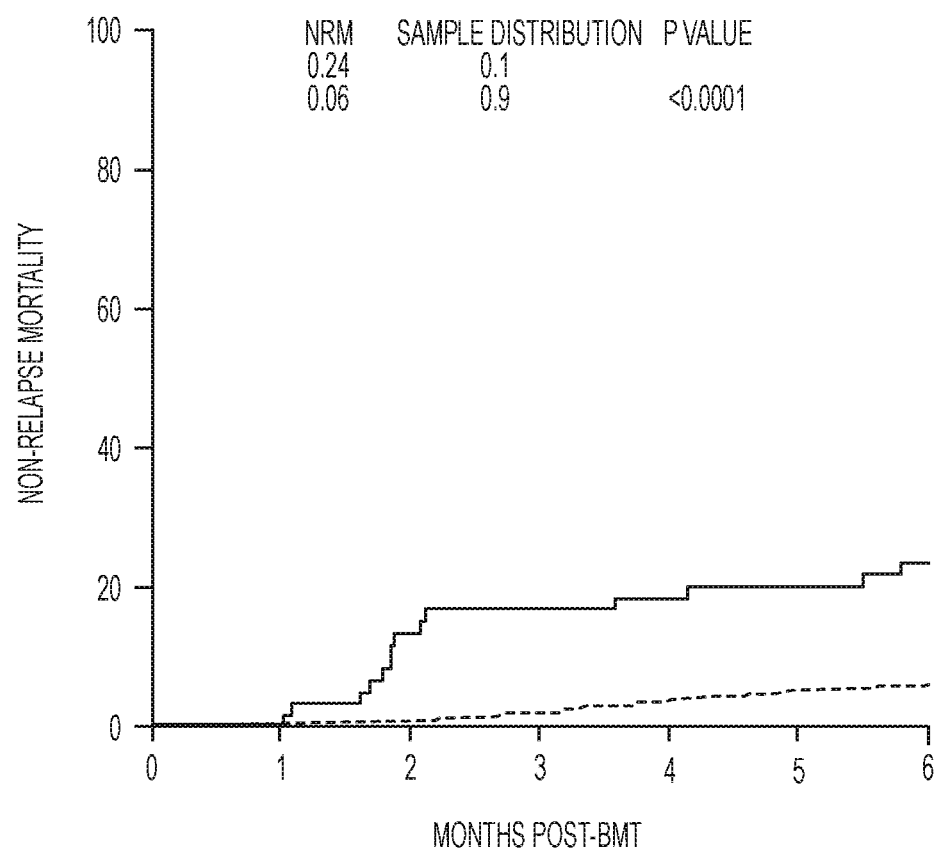
FIG. 10. Low risk patients on day +7 can be stratified on day +14 into high and low risk. Repeated testing of patients who were classified as low risk on day +7 after BMT can provide better risk assessment of risk of developing GVHD.

Patients who were LR on day +7 after BMT were retested on day +14. The algorithm and methods described herein identified additional patients at HR (HR 10%, LR 90%) for NRM. HR patients have higher NRM (24% vs 6%, p<0.0001) (FIG. 10).

Figure 11:
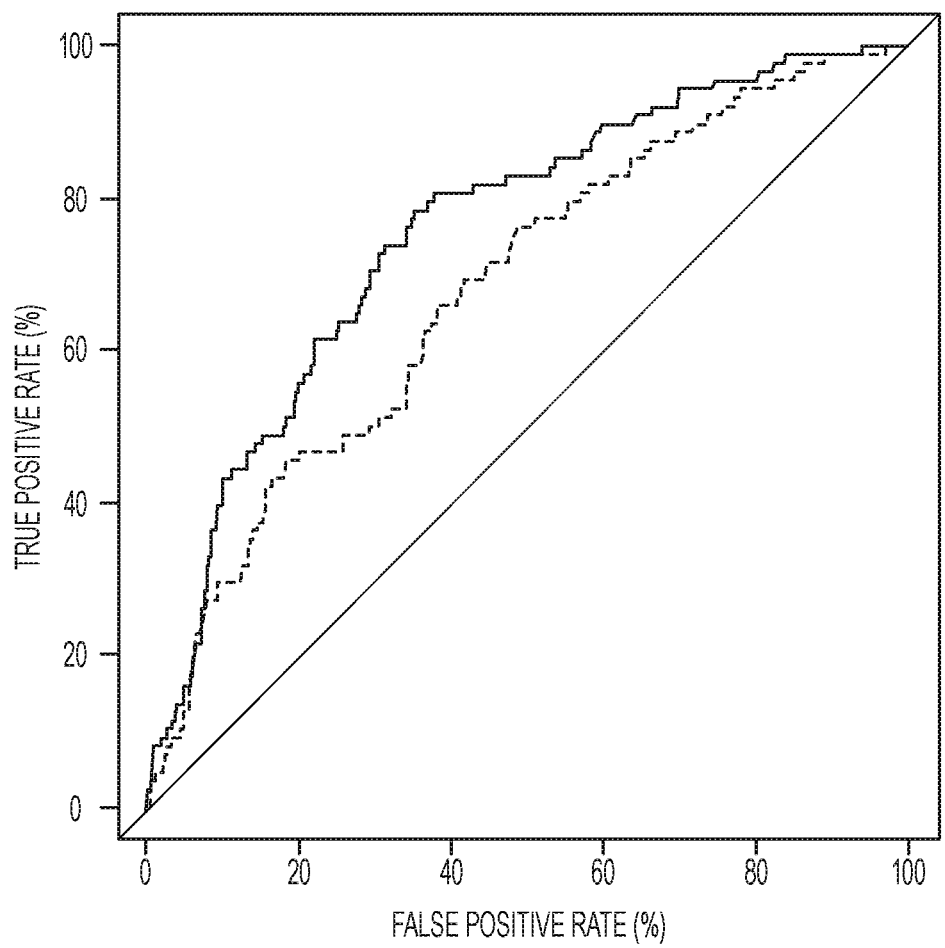
FIG. 11. The AUC of the ROC curve is significantly increased when patients are re-tested on day +14. Re-testing of patients classified as low risk on day +7 after BMT provided improved results when patients were tested on day +14 after BMT.

Repeat testing on day +14 after BMT improves the accuracy of the algorithm (FIG. 11). The sensitivity of the classification substantially improved from 0.41 to 0.59 with acceptable decrease in specificity (0.85 to 0.79).

Figure 12:
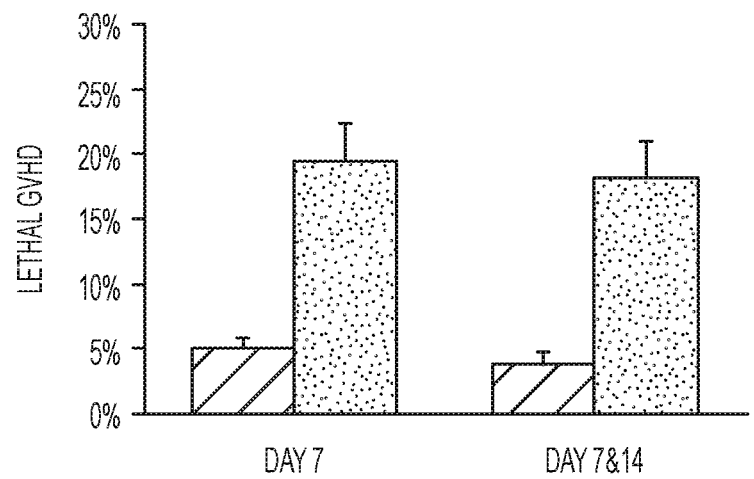
FIG. 12. High risk patients are significantly more likely to develop lethal GVHD at both testing time points. Patients classified as high risk at both day +7 and day +14 after BMT are more likely to develop lethal GVHD. Testing at both time points thus provided a good indication of which patients may require prophylaxis and/or treatment specific for lethal GVHD.

Patients identified as HR on day +7 or on day +14 after BMT are significantly more likely to develop lethal GVHD than LR patients (FIG. 12).

The sensitivity of a biomarker algorithm that predicts lethal GVHD on day +7 after BMT or HCT can be improved by repeat testing one week later on day +14. The majority of GVHD (90%) develops after day +14. Therefore, the algorithm and methods described herein can be used to identify patients at high risk for developing severe or lethal GVHD after undergoing BMT or HCT with sufficient time to intervene pre-emptively.

Materials and Methods

Serum samples were collected from 768 patients at 7 and 14 days after BMT at ten MAGIC (Mount Sinai Acute GVHD International Consortium) centers, as well as their clinical data (dates of GVHD onset, relapse, death, etc).

Concentrations of the two GVHD biomarkers (REG3α and ST2) were measured using enzyme-linked immunosorbent assays (ELISAs) as described herein.

Patients who would not be candidates for pre-emptive therapy based on day 14 results were not re-tested. These included two categories of patients. First, patients who identified as high risk on day +7 (n=145) would already be receiving pre-emptive therapy by day 14. Second, patients who developed GVHD between days 7 and 14 (n=20) would already be receiving treatment for GVHD and thus not candidates for pre-emptive treatment.

Example 3

Testing the Model in Treatment Resistant Patients

Acute graft versus host disease (GVHD) is generally treated with systemic corticosteroid immunosuppression. Clinical response after one week of therapy often guides further treatment decisions, but long-term outcomes can vary widely between centers and more accurate predictive methods tests to predict long-term outcomes are urgently needed.

The inventors analyzed clinical data and blood samples taken after one week of systemic treatment for GVHD from 507 patients in the Mount Sinai Acute GVHD International Consortium (MAGIC), dividing them into test (n=236) and two validation cohorts separated in time (n=142 and 129, respectively).

Initial response to systemic steroids correlated with response at four weeks, one-year non-relapse mortality (NRM) and overall survival (OS). As shown herein, the described algorithm using two biomarkers (ST2 and REG3α) consistently separated patients steroid resistant patients into two groups with dramatically different NRM and OS (p<0.001 for all three cohorts). High biomarker probability, resistance to steroids and GVHD severity (Minnesota risk staging) were all significant predictors of NRM in multivariate analysis. A direct comparison of receiver operating curves showed the area under the curve for biomarker probability (0.82) was significantly greater than that for steroid response (0.68) and for Minnesota high risk (0.65), p<0.004.

Patients who do not respond early to systemic steroids have a generally poor prognosis, but results are inconsistent among transplant centers and biomarkers that accurately predict long term outcomes in this highly immunosuppressed population are urgently needed.

The Mount Sinai Acute GVHD International Consortium (MAGIC) was established to provide consistent multi-center monitoring of acute GVHD severity during treatment as well as to obtain samples that could be interrogated for potential predictive biomarkers.

As described herein, the inventors have developed methods incorporating an algorithm that uses the serum concentrations of GVHD biomarkers suppressor of tumorigencity-2 (ST2) and regenerating islet-derived protein 3-α (REG3α) that generates a probability for NRM and predicts resistance to treatment.

The inventors next decided to determine the extent to which early clinical responses to steroid treatment could predict long-term outcome of patients with acute GVHD, based on biomarkers obtained at the time of the clinical evaluation. It was hypothesized that the probabilities would predict long term outcomes even when the biomarkers are measured at a time the initial response to treatment was already known.

Methods.

Study Design.

Patients from 11 centers in the Mount Sinai Acute GVHD International Consortium (MAGIC) underwent first allogeneic HCT from May 2001 to December 2016 and provided blood samples for a biorepository 7 days after initiation of corticosteroid treatment for newly diagnosed acute GVHD. All patients consented to participation on an institutional review board approved protocol at each MAGIC participating center (Table 10). Patients transplanted before 2016 whose data and GVHD onset samples had previously contributed to the development of the initial algorithm formed the test cohort (n=236)[11,42] whereas patients not previously analyzed formed the validation cohort (n=142). Patients transplanted in 2016 (n=129) formed the second validation cohort.

GVHD clinical staging was standardized using published guidelines.[13] Non-relapse deaths were considered related to GVHD only if the patient died from either GVHD itself or from an infection that developed while receiving systemic steroids (at least 10 mg prednisone daily or equivalent) for the treatment of GVHD. Clinical response to treatment was determined at 1 and 4 weeks after start of treatment according to published criteria.[12] Complete response (CR) was defined as the complete resolution of acute GVHD manifestations in all organs. Partial response (PR) was defined as improvement but not complete resolution of GVHD in all initially affected organs without new target organ involvement. Non-response was defined as all other responses or death before response assessment. Relapse risk was assessed according to published criteria.[43]

Biomarker Determination and Statistical Analyses.

Samples were shipped to a central laboratory where they were analyzed in batches for ST2 and REG3α by ELISA as previously described.[14,15] The inventors then created a competing risks model, with relapse as the competing risk, that predicted six month NRM after one week of systemic GVHD treatment using the concentrations of ST2 and REG3α. The performance of this model was compared to the previously published MAGIC prediction model by calculating the area under the curve of the receiver operating characteristic curve of each model in the validation cohort. The AUC was the same for both models (0.82, p=0.977) and we therefore used the previously published MAGIC prediction model $\log[-\log(1-\hat{p})]=-11.263+1.844(\log ST2)+0.577 (\log REG3\alpha)$ to calculate the probability value ($\hat{p}$) for each patient. An unsupervised learning algorithm, K-medoids clustering that maximized the differences between groups while minimizing the differences in probabilities within each group, was used to identify the threshold that best separated test cohort patients into two groups.[44]

Clinical characteristics of patients between cohorts were compared using chi-squared or Wilcoxon rank-sum tests as appropriate. Competing risks regression with relapse as the competing risk was used to model one-year NRM with early treatment response, clinical risk at onset (Minnesota classification) and biomarkers as predictors. Logistic regression was used to model week 4 resistance to treatment. Differences in cumulative incidence of NRM and relapse between groups were calculated by Gray's test. Overall survival was estimated by the Kaplan-Meier method and differences between groups were calculated using the log-rank test. Areas under the receiver operating characteristic curves were compared using the Delong method.[45] Univariate analyses for NRM were performed on the combined validation cohort patients and included pre-transplant characteristics that are important risk factors for GVHD (Table 9), clinical severity at start of treatment, initial response to treatment, and either biomarker concentrations or the categorical variable of the probability group. Multivariate analyses included all variables that are risk factors for GVHD and that were statistically significant on univariate analysis. All analyses were performed using R statistical package version 3.4.0 (R Development Core Team 2017). Error bars represent the standard error of proportion in all figure parts where error bars are shown.

TABLE 9

Patient Characteristics.

| Characteristic | Test Cohort (n = 236) | Validation Cohort (n = 142) | P value |
|---|---|---|---|
| Median age - yr (range) | 51 (1-73) | 49.5 (1-74) | 0.61 |
| Indication for HCT - no. (%) | | | 0.52 |
| Acute leukemia | 121 (51.3%) | 73 (51.4%) | |
| MDS/MPN | 48 (20.3%) | 24 (16.9%) | |
| Lymphoma | 38 (16.1%) | 19 (13.4%) | |
| Other Malignant | 22 (9.3%) | 20 (14.1%) | |

TABLE 9-continued

Patient Characteristics.

| Characteristic | Test Cohort (n = 236) | Validation Cohort (n = 142) | P value |
|---|---|---|---|
| Non-Malignant | 7 (3.0%) | 6 (4.2%) | |
| Disease Risk Index at HCT - no. (%) | | | 0.67 |
| Low | 16 (6.8%) | 7 (4.9%) | |
| Intermediate | 120 (50.8%) | 78 (54.9%) | |
| High | 61 (25.8%) | 38 (26.8%) | |
| Very high | 20 (8.5%) | 7 (4.9%) | |
| Unknown | 19 (8.1%) | 12 (8.5%) | |
| Donor type - no. (%) | | | 0.48 |
| Related | 67 (28.4%) | 46 (32.4%) | |
| Unrelated | 169 (71.6%) | 96 (67.6%) | |
| HLA-match - no. (%) | | | 1.0 |
| Matched | 159 (67.4%) | 95 (66.9%) | |
| Mismatched | 77 (32.6%) | 47 (33.1%) | |
| Stem cell source - no. (%) | | | 0.21 |
| Marrow | 36 (15.3%) | 30 (21.1%) | |
| Peripheral blood | 179 (75.8%) | 104 (73.2%) | |
| Cord blood | 21 (8.9%) | 8 (5.6%) | |
| Conditioning Regimen Intensity - no. (%) | | | 0.05 |
| Full | 194 (82.2%) | 104 (73.2%) | |
| Reduced | 42 (17.8%) | 38 (26.8%) | |
| GVHD prophylaxis - no. (%) | | | 0.72 |
| CNI/MTX ± other | 144 (61.0%) | 84 (59.2%) | |
| CNI/MMF ± other | 83 (35.2%) | 50 (35.2%) | |
| CNI/sirolimus | 1 (0.4%) | 0 (0%) | |
| Other | 8 (3.4%) | 8 (5.6%) | |
| Onset GVHD: median day (range) | 26 (9-275) | 31 (7-204) | <0.001 |
| Onset GVHD: organ distribution | | | 0.76 |
| Isolated skin | 116 (49.2%) | 67 (47.2%) | |
| Isolated GI (UGI and/or LGI) | 63 (26.7%) | 39 (27.5%) | |
| Isolated liver | 2 (0.8%) | 3 (2.1%) | |
| ≥2 organs involved | 55 (23.3%) | 33 (23.2%) | |
| Onset GVHD grade - no (%) | | | 0.70 |
| I | 73 (30.9%) | 39 (27.5%) | |
| II | 105 (44.5%) | 64 (45.1%) | |
| III | 50 (21.2%) | 31 (21.8%) | |
| IV | 8 (3.4%) | 8 (5.6%) | |
| Week 1 response - no (%) | | | 0.44 |
| Complete or partial response | 114 (48.3%) | 62 (43.7%) | |
| Non-response | 122 (51.7%) | 80 (56.3%) | |
| One-year non-relapse mortality, % | 31.3% | 28.9% | 0.73 |
| One-year relapse rate, % | 20.3% | 16.3% | 0.35 |
| One-year overall survival, % | 56.9% | 59.8% | 0.70 |

Abbreviations:
MDS/MPN, myelodysplastic syndrome/myeloproliferative neoplasia;
CNI, calcineurin inhibitor;
MTX, methotrexate;
MMF, mycophenolic acid;
GI, gastrointestinal;
UGI, upper GI;
LGI, lower GI.

TABLE 10

Patient numbers from each center.

| PARTICIPATING MAGIC CENTERS | TEST COHORT | VALIDATION COHORT | VALIDATION COHORT 2 |
|---|---|---|---|
| Emory University, Atlanta, GA | 4 | 3 | 11 |
| Icahn School of Medicine at Mount Sinai, New York, NY | 1 | 2 | 17 |
| King Chulalongkorn Memorial Hospital, Bangkok, Thailand | 5 | — | — |
| Mayo Clinic, Rochester, MN | 6 | 3 | 7 |
| Ohio State University, Columbus, OH | 8 | 7 | 1 |
| University Hospital Carl Gustav Carus, Dresden, Germany | 3 | 2 | — |
| University of Hamburg, Hamburg, Germany | 23 | 17 | 26 |
| University of Michigan, Ann Arbor, MI | 139 | 101 | — |
| University of Pennsylvania, Philadelphia, PA | 4 | 3 | 9 |
| University of Regensburg, Regensburg, Germany | 25 | 3 | 21 |
| University of Würzburg, Würzburg, Germany | 8 | 1 | 8 |
| Children's Hospital of LA, Los Angeles, CA | — | — | 4 |
| City of Hope Comprehensive Cancer Center, Duarte, CA | — | — | 2 |
| Columbia University, New York, NY | — | — | 3 |
| Massachusetts General, Boston, MA | — | — | 5 |
| University of Erlangen, Erlangen, Germany | — | — | 6 |
| Vanderbilt University, Nashville, TN | — | — | 9 |

Results.
Patient Characteristics.

Clinical data and samples were available from 507 patients with acute GVHD who were treated with systemic corticosteroids. Patients were divided into a test cohort (N=236) and two validation cohorts (N=142 and 129, respectively). The median starting dose of steroids was 2.0 mg/kg/day for patients with grade II-IV disease and 1.0 mg/kg/day for grade I disease. All GVHD treatments are listed in Table 11.

TABLE 11

GVHD treatment.

| PRIMARY THERAPY FOR GVHD | TEST COHORT (n =236) | | VALIDATION COHORT (n = 142) | | VALIDATION COHORT 2 (n = 129) | |
|---|---|---|---|---|---|---|
| | Early Treatment Resistant (n = 122) | Early Treatment Sensitive (n = 114) | Early Treatment Resistant (n = 80) | Early Treatment Sensitive (n = 62) | Early Treatment Resistant (n = 68) | Early Treatment Sensitive (n = 61) |
| Steroids only | 77 | 92 | 47 | 48 | 60 | 58 |
| Steroids plus[1]: | | | | | | |
| Etanercept | 25 | 10 | 24 | 9 | 2 | 0 |
| ECP | 5 | 0 | 0 | 1 | 0 | 0 |
| Other[2] | 5 | 1 | 0 | 0 | 6 | 3 |
| Unknown[3] | 10 | 11 | 9 | 4 | 0 | 0 |

Abbreviations: ECP, extra corporeal photopheresis.
[1]:Primary therapy included agents in addition to steroids either as part of a clinical trial or according to center practice.
[2]Other agents included infliximab, everolimus, tocilizumab, ruxolitinib, etanercept + ECP, mycophenolate mofetil, sirolimus, UVB therapy.
[3]Unknown—data regarding agents in addition to steroids not reported.

Clinical Response After One Week of Treatment Predicts Outcomes.

Figure 13A:
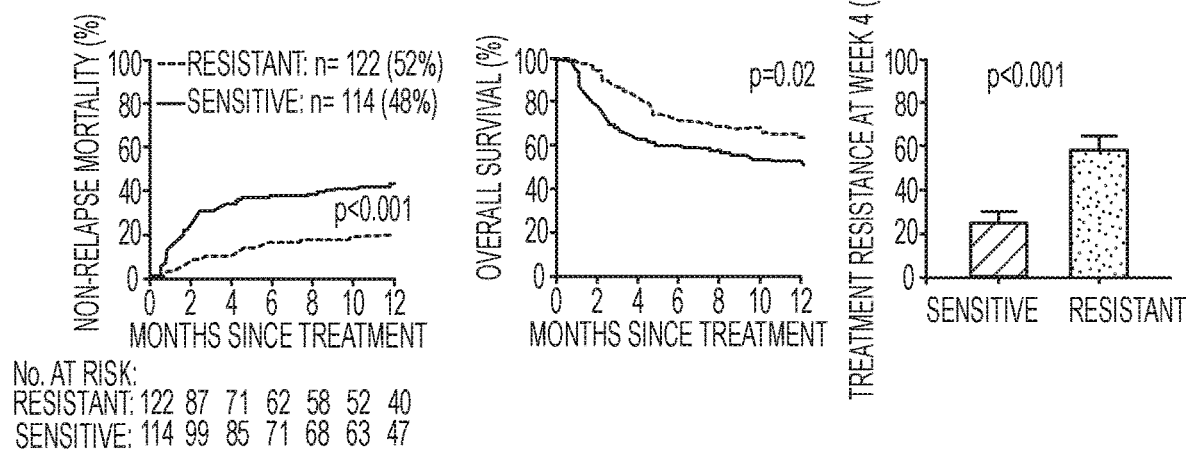
FIG. 13A-13C. Long-term outcomes by clinical response to one week of treatment in all patients. Patients were divided into two groups based on response to treatment: Early treatment sensitive (ETS, dotted line) and early treatment resistant (ETR, solid line).
Figure 13B:
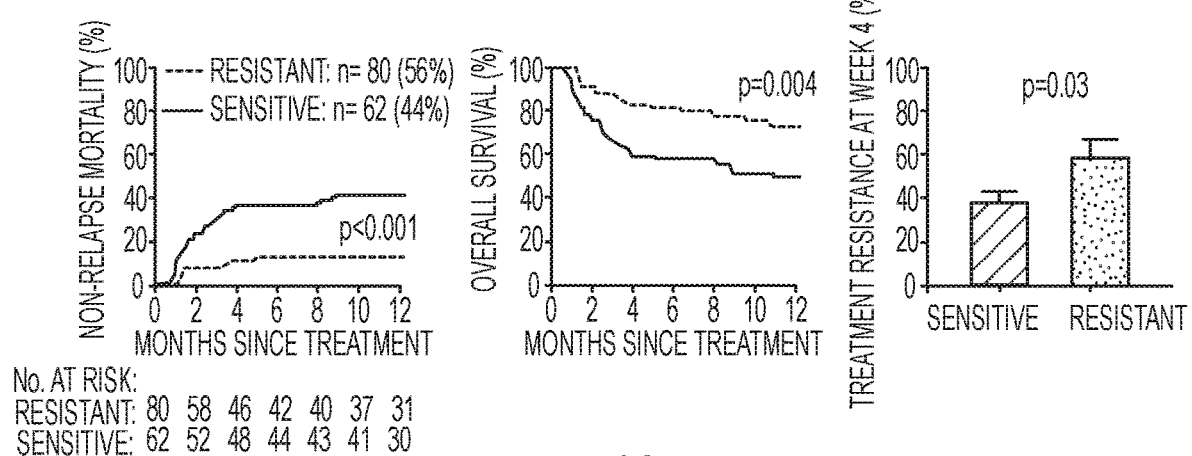
Figure 13C:
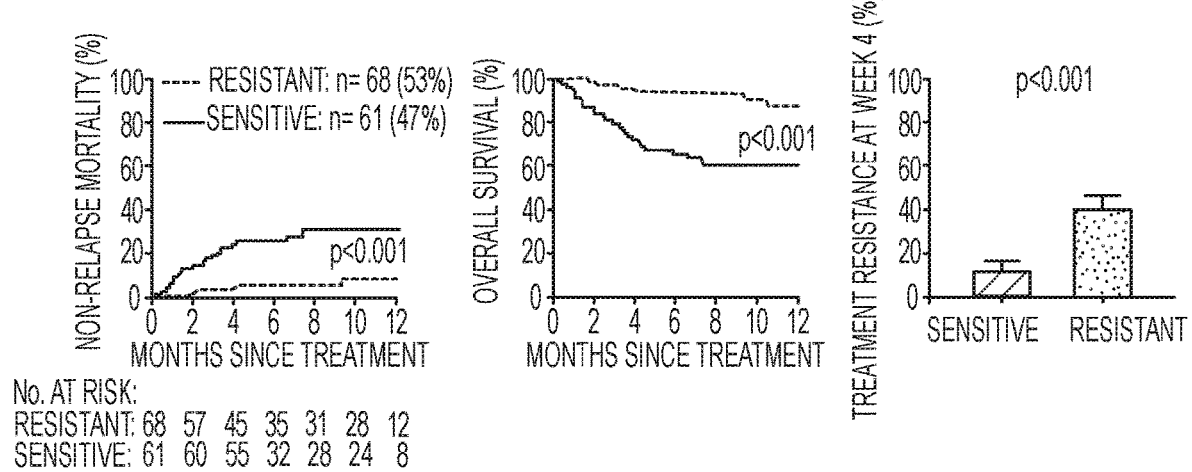
Figure 17:
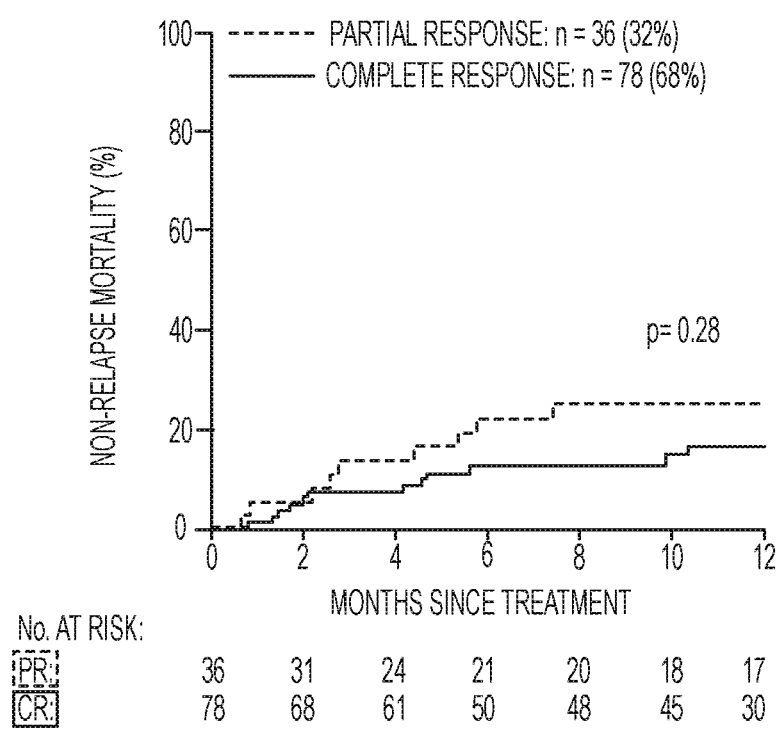
FIG. 17. Cumulative incidence of one-year NRM by complete or partial response after 7 days of systemic treatment. 114 patients in the test cohort responded to the first seven days of treatment with either a complete response (n=78) or a partial response (n=36). The cumulative incidence of 1 year NRM was not statistically different between complete and partial responders (17% vs 25%, p=0.28).

Because the clinical response after one week of systemic steroid treatment often guides further treatment[12,45] the inventors first determined whether clinical response alone could predict NRM at one year. Patients with complete and partial responses in the test cohort had similar NRM (FIG. 17), and these patients were categorized as early treatment sensitive whereas all other patients were categorized as early treatment resistant. NRM at one year was significantly higher in patients with early treatment resistance (FIG. 13A). Relapse did not consistently correlate with response (Table 12) with the result that the early resistance to treatment group experienced significantly worse overall survival (FIG. 13A). Some early treatment resistant patients eventually showed responses to treatment by four weeks, an important surrogate endpoint for long term outcomes[39,40,46], but most early treatment resistant patients remained resistant at four weeks. Similarly, a significant minority of early treatment sensitive patients became resistant to treatment at four weeks. Results were the same in both validation cohorts demonstrating that response to systemic steroids at one week can reliably predict long term outcomes (FIG. 13B, 13C).

TABLE 12

One year cumulative incidence of relapse.

All Patients With Malignancy (N = 488)*

| | Test Cohort (N = 229) | | | Validation Cohort (N = 136) | | | Validation Cohort 2 (N = 123) | | |
|---|---|---|---|---|---|---|---|---|---|
| | Treatment Sensitive (N = 109) | Treatment Resistant (N = 120) | P Value | Treatment Sensitive (N = 58) | Treatment Resistant (N = 78) | P Value | Treatment Sensitive (N = 58) | Treatment Resistant (N = 65) | P value |
| Relapse | 28% | 14% | 0.01 | 23% | 13% | 0.14 | 10% | 9% | 0.702 |

TABLE 12-continued

One year cumulative incidence of relapse.

TREATMENT RESISTANT (N = 263)*

| | Test Cohort (N = 120) | | | Validation Cohort (N = 78) | | | Validation Cohort 2 (N = 65) | | |
|---|---|---|---|---|---|---|---|---|---|
| | Low probability (N = 61) | High probability (N = 59) | P value | Low probability (N = 42) | High probability (N = 36) | P value | Low probability (N = 48) | High probability (N = 17) | P value |
| Relapse | 22% | 7% | 0.02 | 19% | 7% | 0.11 | 8% | 11% | 0.772 |

TREATMENT SENSITIVE (N = 225)*

| | Test Cohort (N = 109) | | | Validation Cohort (N = 58) | | | Validation Cohort 2 (N = 58) | | |
|---|---|---|---|---|---|---|---|---|---|
| | Low probability (N = 78) | High probability (N = 31) | P value | Low probability (N = 45) | High probability (N = 13) | P value | Low probability (N = 51) | High probability (N = 7) | P value |
| Relapse | 30% | 23% | 0.46 | 25% | 15% | 0.49 | 12% | 0% | 0.408 |

*Patients transplanted for non-malignant diseases were excluded from these analyses.

Biomarker Stratification.

Figure 18A:
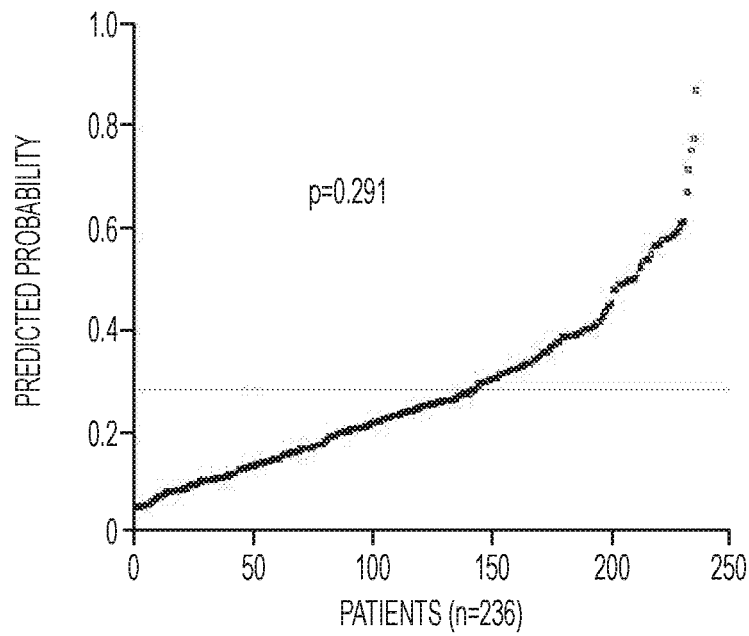
FIG. 18A-18B. Determination of two NRM probability groups by K-medoid clustering. Patients in the test cohort (n=236) were assigned a probability value, $\hat{p}$, generated by the algorithm described herein.
Figure 18B:
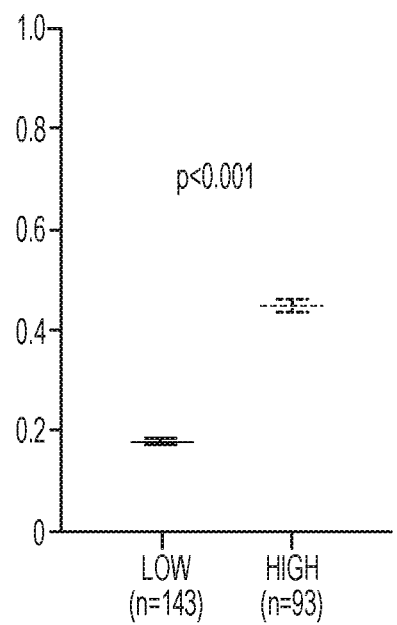

Herein it is demonstrated that serum biomarker concentrations can be used to predict long term outcomes of patients at the onset of GVHD. The inventors hypothesized that an algorithm of the same two biomarkers, ST2 and REG3α, would predict long term outcomes when measured in patients after one week of treatment, when the clinical response was already known. Because the accuracy of the newly derived algorithm was the same as the previously validated algorithm (see Methods herein), the inventors used the original algorithm in all of our analyses. The inventors first determined whether patients could be segregated into two groups (low and high) based only on the predicted probabilities of NRM generated by the biomarker algorithm and without reference to any known clinical characteristics or outcomes (see Methods). A threshold of $\hat{p} \leq 0.291$ best separated patients into groups with low probability (n=143, 61%) and high probability (n=93, 39%) (FIG. 18).

Biomarkers Predict NRM within Response Groups.

The inventors evaluated the long term outcomes of early treatment resistant patients by their probability status. The algorithm analysis identified an unexpectedly large proportion (30-50%) of the early treatment resistant patients in both test and validation cohorts as low probability that and that group experienced strikingly less NRM than the high probability group in all three cohorts (FIG. 14A-14C). Relapse was not consistently different between probability groups (Table 12) resulting in dramatically better OS in the low probability group that was similar to that of steroid sensitive patients. Low probability patients were also significantly less likely to remain resistant to treatment at week four than high probability patients. As expected, GVHD was the leading cause of death in early treatment resistant patients (Table 13).

TABLE 13

Causes of death.
ALL PATIENT DEATHS

| | | TEST COHORT (N = 103) | | VALIDATION COHORT (N = 58) | | VALIDATION COHORT 2 (N = 32) | |
|---|---|---|---|---|---|---|---|
| Cause - no (%) | TOTAL (N = 193) | TREATMENT RESISTANT (N = 62) | TREATMENT SENSITIVE (N = 41) | TREATMENT RESISTANT (N = 40) | TREATMENT SENSITIVE (N = 18) | TREATMENT RESISTANT (N = 26) | TREATMENT SENSITIVE (N = 6) |
| Acute GVHD | 106 (54.9%) | 43 (69.4%) | 16 (39.0%) | 26 (65.0%) | 7 (38.9%) | 13 (50.0%) | 1 (16.6%) |
| Chronic GVHD | 16 (8.3%) | 6 (9.7%) | 3 (7.4%) | 4 (10.0%) | 1 (5.6%) | 1 (3.8%) | 1 (16.6%) |
| Other: | 18 (9.3%) | 3 (4.8%) | 4 (9.7%) | 3 (7.5%) | — | 6 (23.1%) | 2 (33.4%) |
| Infection unrelated to GVHD | 9 | 1 | 2 | 2 | — | 3 | 1 |
| Cardiac event | 2 | 1 | 1 | — | — | — | — |
| Pulmonary event | 3 | — | 1 | — | — | 1 | 1 |
| Multiorgan failure | 1 | 1 | — | — | — | — | — |
| Late graft failure | 2 | — | — | 1 | — | 1 | — |
| New Malignancy | 1 | — | — | — | — | 1 | — |
| Relapse | 53 (27.5%) | 10 (16.1%) | 18 (43.9%) | 7 (17.5%) | 10 (55.5%) | 6 (23.1%) | 2 (33.4%) |

The inventors then evaluated biomarker stratification for patients whose GVHD was sensitive to the first week of systemic treatment. The biomarker algorithm described herein again separated patients into two groups with different outcomes in both the test and first validation cohorts but not in the second validation cohort where the NRM of the early response group was only 8% (FIG. 15A-15C). Relapse rates were again not different between groups (Table 12). A similar pattern was seen for prediction of resistance to treatment at week 4. Thus, the biomarker algorithm did not reliably segregate patients into distinct risk groups when the NRM of the overall group was very low.

Biomarker Probability Scores Predict Outcomes Better than Initial Response to Treatment or Minnesota Clinical Risk.

Figure 16A:
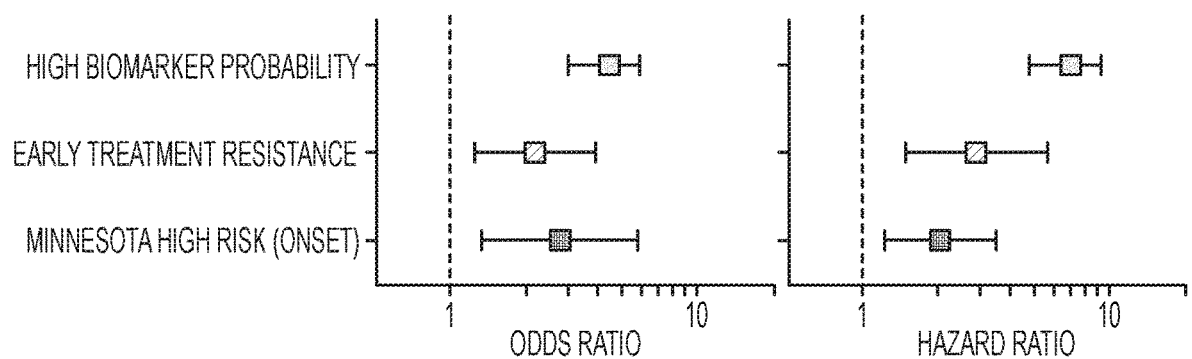
FIG. 16A-16B. Prediction of long term outcomes by early clinical response and biomarker probability status.
Figure 16B:
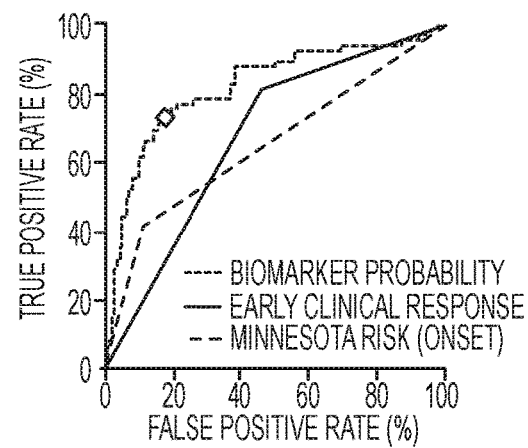

Univariate analyses of important pre-transplant and GVHD clinical variables showed that biomarker probability, both early response to treatment and clinical risk at onset of GVHD (Minnesota classification) each significantly predicted response to treatment at four weeks and one-year NRM (Table 14). When biomarker probabilities were applied to Minnesota risk categories, they further separated each clinical category into two groups with dramatically different long-term outcomes. When these three variables were included in multivariate analysis of long term outcomes, the biomarker risk ratios provided the highest risk ratios, but all three remained significant when controlled for the two other predictors (FIG. 16A). The inventors then directly compared the ability of each variable to predict NRM by creating receiver operating characteristic curves (FIG. 16B). The area under the curve (AUC) for the biomarker probabilities was 0.82, significantly higher than 0.68 for early clinical response and 0.65 for Minnesota clinical risk (p=0.004). The sensitivity, specificity, positive predictive value and negative predictive values for one-year NRM at the threshold used were 74%, 83%, 58% and 91%, respectively. A separate algorithm that included the concentrations of ST2 and REG3α, early treatment response, and Minnesota risk to predict one-year NRM produced an AUC of 0.84 that was not significantly better than the 0.82 for the biomarkers only algorithm.

TABLE 14

Univariate analyses (validation cohort).

| Variable | HR | 95% Confidence Interval | P value |
|---|---|---|---|
| Univariate Analyses to Predict Treatment Resistance at Week 4 | | | |
| Minnesota high risk | 4.55 | 2.39-8.99 | <0.0001 |
| Early non-response | 2.93 | 1.75-4.97 | <0.0001 |
| REG3α at week 1** | 2.53 | 1.65-3.96 | <0.0001 |
| ST2 at week 1** | 10.47 | 4.78-24.24 | <0.0001 |

TABLE 14-continued

Univariate analyses (validation cohort).

| Variable | HR | 95% Confidence Interval | P value |
|---|---|---|---|
| Univariate Analyses to Predict NRM at 1 Year | | | |
| Age* | 1.10 | 0.96-1.22 | 0.16 |
| Unrelated donor | 0.80 | 0.48-1.33 | 0.38 |
| HLA-mismatched | 1.18 | 0.71-1.96 | 0.52 |
| Stem cell source: peripheral blood | 1.75 | 0.85-3.62 | 0.13 |
| Stem cell source: cord blood | 1.49 | 0.48-4.64 | 0.49 |
| Conditioning regimen: reduced | 0.86 | 0.51-1.46 | 0.58 |
| GVHD prophylaxis: other | 0.95 | 0.38-2.34 | 0.91 |
| ATG: yes | 0.56 | 0.31-1.01 | 0.06 |
| Minnesota high risk | 4.18 | 2.54-6.86 | <0.0001 |
| Early non-response | 4.24 | 2.28-7.88 | <0.0001 |
| REG3α at week 1** | 1.04 | 1.03-1.06 | <0.0001 |
| ST2 at week 1** | 1.15 | 1.10-1.19 | <0.0001 |

Reference group for stem cell source is marrow; for GVHD prophylaxis is calcineurin-inhibitor containing prophylaxis.
*The associated increase in hazard for a ten year increase in age.
**The associated increase in hazard with 10% increase in biomarker concentration.

TABLE 15

Incidence of stage 2-4 GI GVHD after four weeks of treatment.

| | ALL PATIENTS (n = 507) | | | | | |
|---|---|---|---|---|---|---|
| | EARLY TREATMENT RESISTANT (n = 270) | | | EARLY TREATMENT SENSITIVE (n = 237) | | |
| GI GVHD* | Low probability (N = 148) | High probability (N = 122) | P value | Low probability (N = 183) | High probability (N = 54) | P value |
| State 2-4 | 9 (6.1%) | 52 (42.6%) | <0.0001 | 3 (1.6%) | 5 (9.3%) | 0.006 |

*GI GVHD was assessed at week 4 or death, whichever came earlier.

TABLE 16

Distribution of probability scores according to presence of lower GI symptoms at week 1.

| | Low probability | High probability |
|---|---|---|
| Lower GI tract symptoms present (n = 145) | 48 (33%) | 97 (67%) |
| Lower GI tract symptoms absent (n = 362) | 283 (78%) | 79 (22%) |
| All patients (n = 507) | 331 (65%) | 176 (35%) |

Discussion.

Little progress has been made during the last several decades in validating new treatments for GVHD for several reasons. The immune systems of all BMT patients have been largely eradicated by the pre-transplant conditioning regimens to prevent rejection the stem cell graft, and half of GVHD develops within the first month of transplant when immunologic reconstitution from the new graft is in its earliest phases.[6,47] All strategies to treat acute GVHD suppress multiple elements of the immune system, further diminishing the immunologic competence of the patient. Even successful treatment minimally requires a month of additional immunosuppression, increasing vulnerability to potentially fatal opportunistic infections. Thus treatment of GVHD leads to severe infections that are directly related to the cumulative steroid dose.[48,49] Additionally, acute GVHD symptom severity can fluctuate widely on a day-to-day basis, introducing significant uncertainty into assessments of response to treatment.[13] GVHD can progress rapidly if not adequately treated however, and thus clinicians often react quickly to worsening symptom severity even though these might resolve without further intervention. Accurate prediction of durable responses and long-term outcomes is thus key to both escalation and de-escalation of immunosuppressive therapy.

Previous studies have found that early clinical response to GVHD treatment correlates poorly with both later clinical response and long-term survival.[40,50] As described herein, although early clinical responses continued to evolve, overall response at one week continued to have a significant predictive value for long-term outcomes in multivariate analysis (FIG. 16A, 16B). Measurement of the algorithm using serum concentrations of two MAGIC biomarkers (ST2 and REG3α) that were measured at the same time as clinical response segregated patients with steroid resistant GVHD into two groups with highly divergent outcomes in all three independent patient cohorts. Patients with a low probability score who have not yet responded to treatment may be slow responders and may not require escalation of immunosuppression despite the appearance of steroid resistance. Given the serious infectious risks of further immunosuppression, clinicians might adopt a stance of watchful waiting for such patients, an approach that could be addressed in a carefully controlled clinical trial.

It is possible that the accuracy of biomarker probabilities reflect the ability of serum concentrations of ST2 and REG3α to measure immunologically mediated changes in tissue more accurately than the clinical appearance of steroid resistance. Both ST2 and REG3α reflect damage to lower gastrointestinal mucosa, particularly in the crypts,[14,24] and patients with high probabilities eventually experience much more GI GVHD (p=0.0X, Table 15). At the time the biomarkers are measured, however, lower GI symptoms also do not predict outcome very accurately because 33% of patients with such symptoms are in the low probability group and 22% of patients without such symptoms are in the high probability group (Table 16). The limited predictive accuracy of steroid resistance may also be attributed to the number of processes that can simultaneously contribute to clinical GVHD symptoms. For example, diarrhea worsened by a concomitant viral gastroenteritis may be treated as GVHD with systemic steroids that in fact may prolong or intensify the viral disease; but infection does not increase the serum concentration of REG3α and thus would not raise the biomarker probability.[44] In pediatric patients, increased levels of ST2 correlate with transplant associated thrombotic microangiopathy (TA-TMA) as well as six month NRM.[51] TA-TMA and damage to the endothelium have been associated with acute GVHD[52,53] but whether such an association also exists in the data presented herein cannot be determined due to lack of relevant data.

Previous studies have found prognostic value for combinations of different biomarkers after two weeks of systemic steroid treatment, but none have determined the prognostic utility of biomarkers obtained earlier than fourteen days into treatment.[54,46] In one single center study of 165 patients, the clinical status after two weeks of systemic steroid treatment for GVHD was a slightly worse predictor for one year NRM than two biomarkers (TIM3 and TNFR1) measured at the same time (AUC of 0.81 and 0.85, respectively). It is perhaps not surprising that the clinical status after two weeks of therapy better reflects long term outcomes than after one week, but such a significant delay to generate actionable information is likely to be of modest clinical utility. Thus, an important strength of the data presented herein is the time of analysis at one week after therapy when information is more likely to be actionable. A second strength is the fact that the patients contributing data and samples from multiple centers were treated without prescriptive directives and therefore reflect the heterogeneity of "real life" GVHD treatment practices, including a second multicenter validation cohort that represents contemporary practice. A third strength of this study is that although biomarkers were measured only at a single time point, the same algorithm that generated the probability score following treatment can also predict outcomes when used prior to and at the onset of GVHD symptoms.[42] The use of the same algorithm should enable the comparisons of probabilities generated serially at multiple time points following HCT, facilitating the incorporation of biomarker measurements into clinical practice. It is important to note, however, that this study has not demonstrated that therapeutic decisions based on biomarker probabilities can change outcome for patients with GVHD. But such probabilities should prove valuable clinical research tools because even relatively large clinical trials for acute GVHD generally do not enroll more than a few hundred patients.[50,55] As a result, experimental therapies need to demonstrate a large benefit in order to prove beneficial, an outcome that has proved elusive over the past 40 years. The inclusion of patients who are likely to respond to standard therapy in a placebo controlled trial reduces the likelihood of detecting a difference between arms; stratification of treatments by biomarker probability will avoid such a pitfall.

Thus, the ability of the biomarker probability algorithms as described herein to categorize predict long term GVHD risk for patients who are not responding to systemic therapy should prove useful in clinical trial design and ultimately may help tailor GVHD treatment to the risks and benefits for individual patients. The data presented herein suggests that biomarker probabilities obtained during treatment should be useful as eligibility criteria for clinical trials testing new therapeutic approaches to GVHD. The ability to identify high and low risk populations in patients with steroid refractory GVHD should prove useful in determining the efficacy of experimental treatments.

REFERENCES

1. Ferrara J L, Levine J E, Reddy P, and Holler E. Graft-versus-host disease. Lancet. 2009; 373(9674):1550-61.
2. Anasetti C, Logan B R, Lee S J, et al. Peripheral-blood stem cells versus bone marrow from unrelated donors. N Engl J Med. 2012; 367(16):1487-96.
3. Gooley T A, Chien J W, Pergam S A, et al. Reduced mortality after allogeneic hematopoietic-cell transplantation. N Engl J Med. 2010; 363(22):2091-101.
4. Socie G, Ritz J, and Martin P J. Current challenges in chronic graft-versus-host disease. Biol Blood Marrow Transplant. 2010; 16(1 Suppl):S146-51.
5. Harris A C, Ferrara J L, and Levine J E. Advances in predicting acute GVHD. Br J Haematol. 2013; 160(3):288-302.
6. Jagasia M, Arora M, Flowers M E, et al. Risk factors for acute GVHD and survival after hematopoietic cell transplantation. Blood. 2012; 119(1):296-307.
7. Finke J, Bethge W A, Schmoor C, et al. Standard graft-versus-host disease prophylaxis with or without anti-T-cell globulin in haematopoietic cell transplantation from matched unrelated donors: a randomised, open-label, multicentre phase 3 trial. Lancet Oncol. 2009; 10(9):855-64.

8. Nucci M, Andrade F, Vigorito A, et al. Infectious complications in patients randomized to receive allogeneic bone marrow or peripheral blood transplantation. Transpl Infect Dis. 2003; 5(4):167-73.
9. Tomblyn M, Chiller T, Einsele H, et al. Guidelines for preventing infectious complications among hematopoietic cell transplantation recipients: a global perspective. Biol Blood Marrow Transplant. 2009; 15(10):1143-238.
10. Majhail N S, Chitphakdithai P, Logan B, et al. Significant improvement in survival after unrelated donor hematopoietic cell transplantation in the recent era. Biol Blood Marrow Transplant. 2015; 21(1):142-50.
11. Levine J E, Braun T M, Harris A C, et al. A prognostic score for acute graft-versus-host disease based on biomarkers: a multicentre study. Lancet Haematol. 2015; 2(1):e21-9.
12. MacMillan M L, Robin M, Harris A C, et al. A refined risk score for acute graft-versus-host disease that predicts response to initial therapy, survival, and transplant-related mortality. Biol Blood Marrow Transplant. 2015; 21(4):761-7.
13. Harris A C, Young R, Devine S, et al. International, Multicenter Standardization of Acute Graft-versus-Host Disease Clinical Data Collection: A Report from the Mount Sinai Acute GVHD International Consortium. Biol Blood Marrow Transplant. 2016; 22(1):4-10.
14. Ferrara J L, Harris A C, Greenson J K, et al. Regenerating islet-derived 3-alpha is a biomarker of gastrointestinal graft-versus-host disease. Blood. 2011; 118(25):6702-8.
15. Vander Lugt M T, Braun T M, Hanash S, et al. ST2 as a Marker for Risk of Therapy-Resistant Graft-versus-Host Disease and Death. New England Journal of Medicine. 2013; 369(6):529-39.
16. Paczesny S, Krijanovski O I, Braun T M, et al. A biomarker panel for acute graft-versus-host disease. Blood. 2009; 113(2):273-8.
17. Fine J P, and Gray R J. A Proportional Hazards Model for the Subdistribution of a Competing Risk. Journal of the American Statistical Association. 1999; 94(446):496-509.
18. Akaike H. A new look at the statistical model identification. IEEE Transactions on Automatic Control. 1974; 19(6):716-23.
19. Xu Q-S, and Liang Y-Z. Monte Carlo cross validation. Chemometrics and Intelligent Laboratory Systems. 2001; 56(1):1-11.
20. Kollman C, Spellman S R, Zhang M J, et al. The effect of donor characteristics on survival after unrelated donor transplantation for hematologic malignancy. Blood. 2016; 127(2):260-7.
21. Castilla-Llorente C, Martin P J, McDonald G B, et al. Prognostic factors and outcomes of severe gastrointestinal GVHD after allogeneic hematopoietic cell transplantation. Bone Marrow Transplant. 2014; 49(7):966-71.
22. Hill G R, Crawford J M, Cooke K R, Brinson Y S, Pan L, and Ferrara J L. Total body irradiation and acute graft-versus-host disease: the role of gastrointestinal damage and inflammatory cytokines. Blood. 1997; 90(8):3204-13.
23. Reichenbach D K, Schwarze V, Matta B M, et al. The IL-33/ST2 axis augments effector T-cell responses during acute GVHD. Blood. 2015; 125(20):3183-92.
24. Zhang J, Ramadan A M, Griesenauer B, et al. ST2 blockade reduces sST2-producing T cells while maintaining protective mST2-expressing T cells during graft-versus-host disease. Sci Transl Med. 2015; 7(308):308ra160.
25. Ueha S, Murai M, Yoneyama H, et al. Intervention of MAdCAM-1 or fractalkine alleviates graft-versus-host reaction associated intestinal injury while preserving graft-versus-tumor effects. J Leukoc Biol. 2007; 81(1):176-85.
26. Waldman E, Lu S X, Hubbard V M, et al. Absence of beta7 integrin results in less graft-versus-host disease because of decreased homing of alloreactive T cells to intestine. Blood. 2006; 107(4):1703-11.
27. Murai M, Yoneyama H, Ezaki T, et al. Peyer's patch is the essential site in initiating murine acute and lethal graft-versus-host reaction. Nat Immunol. 2003; 4(2):154-60.
28. Chen Y B, Kim H T, McDonough S, et al. Up-Regulation of alpha4beta7 integrin on peripheral T cell subsets correlates with the development of acute intestinal graft-versus-host disease following allogeneic stem cell transplantation. Biol Blood Marrow Transplant. 2009; 15(9):1066-76.
29. Targan S R, Feagan B G, Fedorak R N, et al. Natalizumab for the treatment of active Crohn's disease: results of the ENCORE Trial. Gastroenterology. 2007; 132(5):1672-83.
30. Sandborn W J, Feagan B G, Rutgeerts P, et al. Vedolizumab as induction and maintenance therapy for Crohn's disease. N Engl J Med. 2013; 369(8):711-21.
31. Vermeire S, O'Byrne S, Keir M, et al. Etrolizumab as induction therapy for ulcerative colitis: a randomised, controlled, phase 2 trial. Lancet. 2014; 384(9940):309-18.
32. Ogawa H, Fukushima K, Naito H, et al. Increased expression of HIP/PAP and regenerating gene III in human inflammatory bowel disease and a murine bacterial reconstitution model. Inflamm Bowel Dis. 2003; 9(3):162-70.
33. Levine J E, Huber E, Hammer S T, et al. Low Paneth cell numbers at onset of gastrointestinal graft-versus-host disease identify patients at high risk for nonrelapse mortality. Blood. 2013; 122(8): 1505-9.
34. Munneke J M, Bjorklund A T, Mjosberg J M, et al. Activated innate lymphoid cells are associated with a reduced susceptibility to graft-versus-host disease. Blood. 2014; 124(5):812-21.
35. Sanos S L, Vonarbourg C, Mortha A, and Diefenbach A. Control of epithelial cell function by interleukin-22-producing RORgammat+innate lymphoid cells. Immunology. 2011; 132(4):453-65.
36. Lindemans C A, Calafiore M, Mertelsmann A M, et al. Interleukin-22 promotes intestinal-stem-cell-mediated epithelial regeneration. Nature. 2015; 528(7583):560-4.
37. Sullivan K. Graft-vs.-host disease. In: Blume K G, F S, Appelbaum F R, editors. Thomas' Hematopoietic Cell Transplantation. 3rd ed. Oxford, U.K.: Blackwell Publishing; 2004. pp. 635-64.
38. Deeg H J. How I treat refractory acute GVHD. Blood 2007; 109:4119-26.
39. MacMillan M L, DeFor T E, Weisdorf D J. The best endpoint for acute GVHD treatment trials. Blood 2010; 115:5412-7.
40. Saliba R M, Couriel D R, Giralt S, et al. Prognostic value of response after upfront therapy for acute GVHD. Bone Marrow Transplant 2012; 47:125-31.
41. Hahn T, Sucheston-Campbell L E, Preus L, et al. Establishment of definitions and review process for consistent adjudication of cause-specific mortality after allogeneic unrelated-donor hematopoietic cell transplantation. Biol Blood Marrow Transplant 2015; 21:1679-86.
42. Hartwell M J, Ozbek U, Holler E, et al. An early biomarker algorithm predicts lethal graft-versus-host disease and survival. JCI Insight 2017; 2:e89798.
43. Armand P, Kim H T, Logan B R, et al. Validation and refinement of the disease risk index for allogeneic stem cell transplantation. Blood 2014; 123:3664-71.
44. Reynolds A P, Richards G, de la Iglesia B, Rayward-Smith V J. Clustering rules: A comparison of partitioning and hierarchical clustering algorithms. J Math Model Algor 2006; 5:475-504.
45. Martin P J, Rizzo J D, Wingard J R, et al. First- and second-line systemic treatment of acute graft-versus-host disease: recommendations of the American Society of Blood and Marrow Transplantation. Biol Blood Marrow Transplant 2012; 18:1150-63.
46. Levine J E, Logan B, Wu J, et al. Graft-versus-host disease treatment: predictors of survival. Biol Blood Marrow Transplant 2010; 16:1693-9.
47. Mehta R S, Rezvani K. Immune reconstitution post allogeneic transplant and the impact of immune recovery on the risk of infection. Virulence 2016; 7:901-16.
48. Matsumura-Kimoto Y, Inamoto Y, Tajima K, et al. Association of cumulative steroid dose with risk of infection after treatment for severe acute graft-versus-host disease. Biol Blood Marrow Transplant 2016; 22:1102-7.
49. Miller H K, Braun T M, Stillwell T, et al. Infectious risk after allogeneic hematopoietic cell transplantation complicated by acute graft-versus-host disease. Biol Blood Marrow Transplant 2017; 23:522-8.
50. Bolanos-Meade J, Logan B R, Alousi A M, et al. Phase 3 clinical trial of steroids/mycophenolate mofetil vs steroids/placebo as therapy for acute GVHD: BMT CTN 0802. Blood 2014; 124:3221-7.
51. Rotz S J, Dandoy C E, Davies S M. ST2 and endothelial injury as a link between GVHD and microangiopathy. N Engl J Med 2017; 376:1189-90.
52. Dietrich S, Falk C S, Benner A, et al. Endothelial vulnerability and endothelial damage are associated with risk of graft-versus-host disease and response to steroid treatment. Biol Blood Marrow Transplant 2013; 19:22-7.
53. Penack O, Socie G, van den Brink M R. The importance of neovascularization and its inhibition for allogeneic hematopoietic stem cell transplantation. Blood 2011; 117: 4181-9.
54. McDonald G B, Tabellini L, Storer B E, et al. Predictive value of clinical findings and plasma biomarkers after fourteen days of prednisone treatment for acute graft-versus-host disease. Biol Blood Marrow Transplant 2017; 23:1257-63.
55. Hockenbery D M, Cruickshank S, Rodell T C, et al. A randomized, placebo-controlled trial of oral beclomethasone dipropionate as a prednisone-sparing therapy for gastrointestinal graft-versus-host disease. Blood 2007; 109:4557-63.

While several possible embodiments are disclosed above, embodiments of the present invention are not so limited. These exemplary embodiments are not intended to be exhaustive or to unnecessarily limit the scope of the invention, but instead were chosen and described in order to explain the principles of the present invention so that others skilled in the art may practice the invention. Indeed, various modifications of the invention in addition to those described herein will become apparent to those skilled in the art from the foregoing description. Such modifications are intended to fall within the scope of the appended claims. Further, the terminology employed herein is used for the purpose of describing exemplary embodiments only and the terminology is not intended to be limiting since the scope of the various embodiments of the present invention will be limited only by the appended claims and equivalents thereof. The scope of the invention is therefore indicated by the following claims, rather than the foregoing description and above-discussed embodiments, and all changes that come within the meaning and range of equivalents thereof are intended to be embraced therein.

All patents, applications, publications, test methods, literature, and other materials cited herein are hereby incorporated by reference in their entirety as if physically present in this specification.

What is claimed is:

1. A method for determining the risk of developing severe acute graft versus host disease (GVHD) in a patient who has recently undergone hematopoietic cellular transplantation (HCT), consisting of the steps of:
   a) measuring level(s) of at least one of suppression of tumorigenicity 2 protein (ST2) and regenerating islet-derived 3-alpha (Reg3α) in a first blood sample collected from the patient;
   b) analyzing the level(s) according to the algorithm $\log[-\log(1-\hat{p})] = -11.263 + 1.844(\log ST2) + 0.577(\log REG3\alpha)$;
   c) determining a first $\hat{p}$ value for the patient;
   d) comparing the first $\hat{p}$ value obtained from the measurement analysis to an optimal classification threshold, wherein the optimal classification threshold is a $\hat{p}$ value of greater than or equal to 0.16;
   e) identifying the patient as (i) being at risk for developing severe acute GVHD when the first $\hat{p}$ value is greater than or equal to the optimal classification threshold or (ii) not being at risk for developing severe acute GVHD when the first $\hat{p}$ value is less than the optimal classification threshold; and
   (f) treating the patient determined to have, or be at risk for, severe acute GVHD,
   wherein the treatment comprises one of:
   (i) administration of appropriate prophylactically effective pharmaceutical compositions and/or use of appropriate prophylactically effective methods, or
   (ii) administration of appropriate therapeutically effective pharmaceutical compositions and/or use of appropriate therapeutically effective methods.

2. The method as described in claim 1, wherein the patient is suffering from a high risk hematologic malignancy.

3. The method as described in claim 1, wherein the patient is suffering from leukemia, lymphoma, multiple myeloma, acute leukemia, acute myeloid leukemia, dysplastic condition, and/or acute lymphocytic leukemia (ALL).

4. The method as described in claim 1, wherein the patient has received HCT at least four days before the first blood sample is collected.

5. The method as described in claim 1, wherein the patient has received HCT at most ten days before the first blood sample is collected.

6. The method as described in claim 1, wherein the patient has received HCT between four to ten days before the first blood sample is collected.

7. The method as described in claim 1, wherein the patient has received HCT seven days before the first blood sample is collected.

8. The method as described in claim 1, wherein step (a) further comprises obtaining a blood sample from the patient and subsequently isolating at least one of ST2 and Reg3α.

9. The method as described in claim 1, wherein step (a) further comprises determining the levels of both of ST2 and Reg3α.

10. The method as described in claim 9, wherein determination of the levels of at least one of ST2 and Reg3α further comprises isolating nucleic acid and/or protein from the sample.

11. The method as described in claim 1, wherein the patient is tested at multiple time points after receiving HCT to monitor development of GVHD or transfusion associated GVHD (TA GVHD).

12. The method of claim 1, wherein the first blood sample is taken from the patient about 7 days after receiving HCT, and a second blood sample is taken from the patient about 14 days after receiving HCT.

13. A method for predicting severe acute graft versus host disease (GVHD) in a patient who has recently undergone hematopoietic cellular transplantation (HCT), consisting of the steps of:
   a) measuring level(s) of at least one of suppression of tumorigenicity 2 protein (ST2) and regenerating islet-derived 3-alpha (Reg3α) in a first blood sample collected from the patient;
   b) analyzing the level(s) according to the algorithm $\log[-\log(1-\hat{p})] = -11.263 + 1.844(\log ST2) + 0.577(\log REG3α)$;
   c) determining a first $\hat{p}$ value for the patient;
   d) comparing the first $\hat{p}$ value obtained from the measurement analysis to an optimal classification threshold, wherein the optimal classification threshold is a $\hat{p}$ value of greater than or equal to 0.16;
   e) identifying the patient as (i) being at risk for developing severe acute GVHD when the first $\hat{p}$ value is greater than or equal to the optimal classification threshold or (ii) not being at risk for developing severe acute GVHD when the first $\hat{p}$ value is less than the optimal classification threshold; and
   (f) treating the patient determined to have, or be at risk for, severe acute GVHD,
   wherein the treatment comprises one of:
   (i) administration of appropriate prophylactically effective pharmaceutical compositions and/or use of appropriate prophylactically effective methods, or
   (ii) administration of appropriate therapeutically effective pharmaceutical compositions and/or use of appropriate therapeutically effective methods.

14. A method for monitoring the potential to develop severe acute graft versus host disease (GVHD) in a patient who has recently undergone hematopoietic cellular transplantation (HCT), consisting of the steps of:
   a) measuring level(s) of at least one of suppression of tumorigenicity 2 protein (ST2) and regenerating islet-derived 3-alpha (Reg3α) in a first blood sample collected from the patient;
   b) analyzing the level(s) according to the algorithm $\log[-\log(1-\hat{p})] = -11.263 + 1.844(\log ST2) + 0.577(\log REG3α)$;
   c) determining a first $\hat{p}$ value for the patient;
   d) comparing the first $\hat{p}$ value obtained from the measurement analysis to an optimal classification threshold, wherein the optimal classification threshold is a $\hat{p}$ value of greater than or equal to 0.16;
   e) identifying the patient as (i) having or being at risk for severe acute GVHD when the first $\hat{p}$ value is greater than or equal to the optimal classification threshold or (ii) not having or being at risk for severe acute GVHD when the first $\hat{p}$ value is less than the optimal classification threshold;
   f) measuring the level(s) of at least one of ST2 and Reg3α in a second blood sample collected from the patient more than eleven days after undergoing HCT;
   g) analyzing the level(s) in the second blood sample according to the algorithm $\log[-\log(1-\hat{p})] = -11.263 + 1.844(\log ST2) + 0.577(\log REG3α)$;
   h) determining a second $\hat{p}$ value for the patient;
   i) comparing the second $\hat{p}$ value obtained from the measurement analysis to the optimal classification threshold and to the first $\hat{p}$ value;
   j) identifying the patient as (i) continuing to have or be at risk for severe acute GVHD when the second $\hat{p}$ value is greater than or equal to the optimal classification threshold and/or when the second $\hat{p}$ value is the same as or greater than the first $\hat{p}$ value or (ii) not continuing to have or not continuing to be at risk of having severe acute GVHD when the first $\hat{p}$ value is less than the optimal classification threshold;
   k) optionally modifying the patient's therapeutic or prophylactic regimen based on the identification in step j;
   l) repeating steps f-j on subsequent days after HCT as determined by a physician; and
   m) treating the patient determined to have, or be at risk for, severe acute GVHD, wherein the treatment comprises one of:
   (i) administration of appropriate prophylactically effective pharmaceutical compositions and/or use of appropriate prophylactically effective methods, or
   (ii) administration of appropriate therapeutically effective pharmaceutical compositions and/or use of appropriate therapeutically effective methods.

* * * * *